US012808869B2

(12) United States Patent
Samavati

(10) Patent No.: US 12,808,869 B2
(45) Date of Patent: Nov. 24, 2026

(54) **TRANSKETOLASE EPITOPES, METHODS, AND DEVICES FOR IGG-BASED *TUBERCULOSIS* SERODIAGNOSIS**

(71) Applicant: Wayne State University, Detroit, MI (US)

(72) Inventor: Lobelia Samavati, Beverly Hills, MI (US)

(73) Assignee: Wayne State University, Detroit, MI (US)

( * ) Notice: Subject to any disclaimer, the term of this patent is extended or adjusted under 35 U.S.C. 154(b) by 264 days.

(21) Appl. No.: 18/400,897

(22) Filed: Dec. 29, 2023

(65) Prior Publication Data

US 2024/0219384 A1 Jul. 4, 2024

Related U.S. Application Data

(60) Provisional application No. 63/478,080, filed on Dec. 30, 2022.

(51) Int. Cl.

| | |
|---|---|
| ***G01N 33/569*** | (2006.01) |
| ***G01N 21/25*** | (2006.01) |
| ***G01N 33/543*** | (2006.01) |
| ***G01N 33/68*** | (2006.01) |

(52) U.S. Cl.

CPC ......... *G01N 33/5695* (2013.01); *G01N 21/25* (2013.01); *G01N 33/543* (2013.01); *G01N 33/6854* (2013.01); *G01N 2333/35* (2013.01); *G01N 2333/9104* (2013.01); *G01N 2800/26* (2013.01)

(58) Field of Classification Search

CPC .. G01N 33/5695; G01N 21/25; G01N 33/543; G01N 33/6854; G01N 2333/35; G01N 2333/9104; G01N 2800/26

See application file for complete search history.

(56) References Cited

U.S. PATENT DOCUMENTS

2019/0055602 A1* 2/2019 Samavati ............. C12Q 1/6883

OTHER PUBLICATIONS

Cox KL, Devanarayan V, Kriauciunas A, et al. Immunoassay Methods. May 1, 2012 [Updated Jul. 8, 2019]. In: Markossian S, Grossman A, Baskir H, et al., editors. Assay Guidance Manual [Internet]. https://www.ncbi.nlm.nih.gov/books/NBK92434/ (Year: 2019).*

* cited by examiner

*Primary Examiner* — Anne M. Gussow
*Assistant Examiner* — Amelia Stephens
(74) *Attorney, Agent, or Firm* — Lee & Hayes, P.C.

(57) ABSTRACT

The present disclosure relates generally to compositions, methods, devices, and systems for the diagnosis of tuberculosis in a subject. Also described is the development of direct ELISA systems for detecting IgG against specific sequences, such as SEQ ID NO: 1, SEQ ID NO: 12 (TKTμ; DLSSEVATHQPIIACLP), SEQ ID NO: 3 (TKT1; GEDGPTHQPIEHLSA), or SEQ ID NO: 5 (TKT3; HDSIGLGEDGPTHQPIEHLS).

13 Claims, 49 Drawing Sheets
(18 of 49 Drawing Sheet(s) Filed in Color)

Specification includes a Sequence Listing.

FIG. 2A (part 1 of 3)
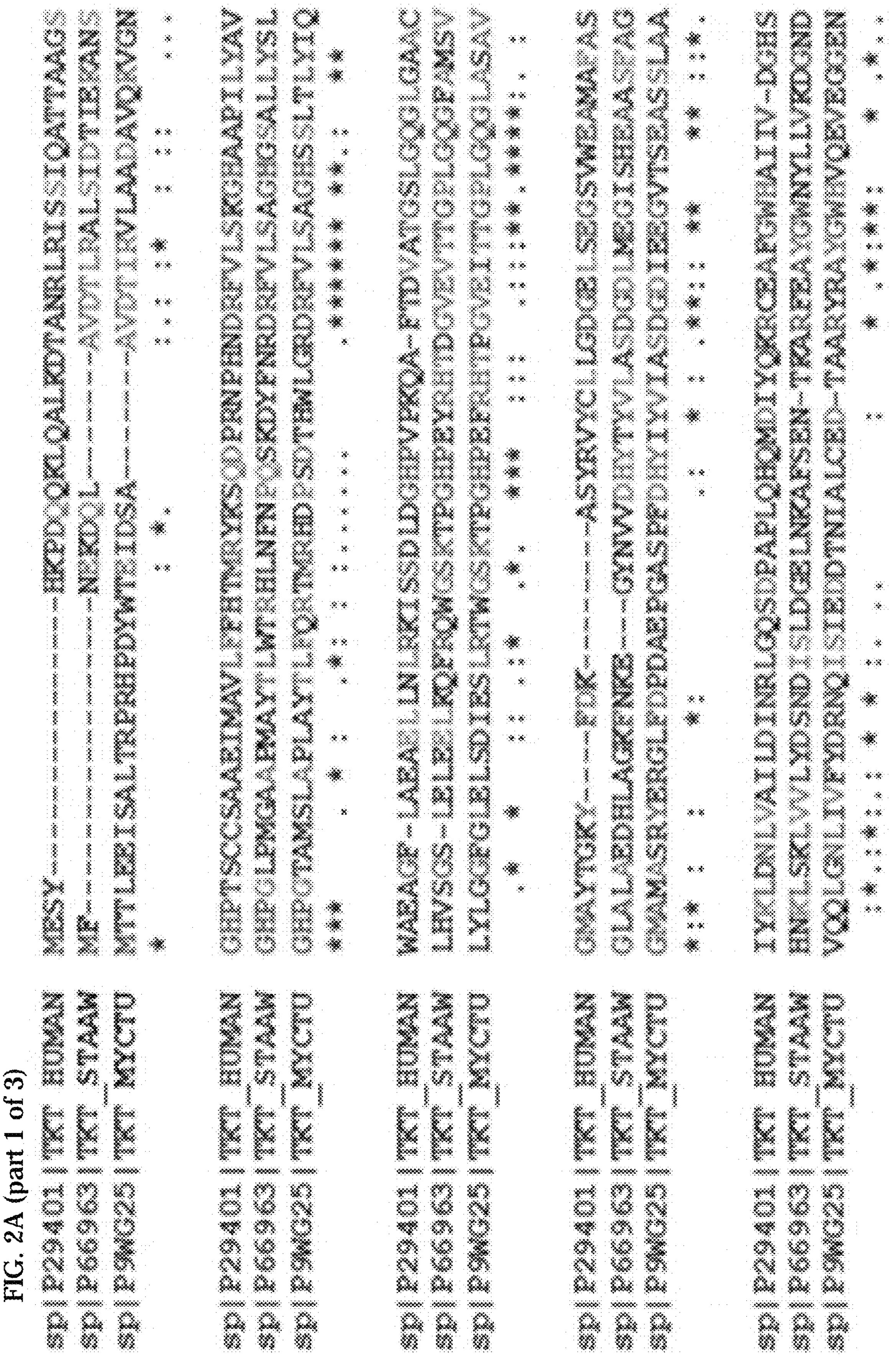

FIG. 2A (part 2 of 3)

```
sp|P29401|TKT_HUMAN  VEELCKAFGQAK---HQPTAIIAKTFKGRGITGVEDKESWHGKPLPKNMA
sp|P66963|TKT_STAAW  LEEIDKAITTAKS-QEGPTIIEVKTTIGFGSPNKAGTNGVHGAPLGEVER
sp|P9WG25|TKT_MYCTU  VVGIEEAIANAQAVTDRPSFIALRTVIGYPAPNLMDTGKAHGAALGDDEV

sp|P29401|TKT_HUMAN  EQ-------------IIQEIYS----------------QIQSKK-KILAT
sp|P66963|TKT_STAAW  KLTFENYGLDPEKRFNVSEEVYEIFQNTMLKRANEDESQWNSLLEKYAET
sp|P9WG25|TKT_MYCTU  AAVKKIVGFDPDKTFQVREDVLTHT-RGLVARGKQAHERWQLEFDAWARR

sp|P29401|TKT_HUMAN  PFQED-----APSVDIANIRMPSLPSYKVGDK-IATRKAYGQALAKLGHA
sp|P66963|TKT_STAAW  YPELAEEFKLAISGKLPKNYKDELPRFELGHN-GASRADSGTVIQAISKT
sp|P9WG25|TKT_MYCTU  EPERKALLDRLLAQKLPDGWDADLPHWEPGSKALATRAASGAVLSALGPK

sp|P29401|TKT_HUMAN  SDRIIALDGDTKNSTFSEI---------------FKKEH-PDRFIECYIA
sp|P66963|TKT_STAAW  VPSFFGGSADLAGSNKSNVNDATD----------YSSETPEGKNVWFGVR
sp|P9WG25|TKT_MYCTU  LPELWGGSADLAGSNNTTIKGADSFGPPSISTKEYTAHW-YGRTLHFGVR

sp|P29401|TKT_HUMAN  EQNMVSIAVGCATRNRTVPFCSTFAAFFTRAFDQIRMAAISESNINLCGS
sp|P66963|TKT_STAAW  EFAMGAAVNGMAAHGGLHPYGATFFVFSDYLKPALRLSSIMGLNATFIFT
sp|P9WG25|TKT_MYCTU  EHAMGAILSGIVLHGPTRAYGGTFLQFSDYMRPAVRLAALMDIDTIYVWT
```

FIG. 2A (part 3 of 3)

```
sp|P29401|TKT_HUMAN   HCGVSIGEDGPSQMALEDLAMFRSVPTSTVFYPSDGVATEKAVELAA--N
sp|P66963|TKT_STAAW   HDSIAVGEDGPTHEPIEQLAGLRAIPNMNVIRPADGNETRVAWEVAL--E
sp|P9WG25|TKT_MYCTU   HDSIGLGEDGPTHQPIEHLSALRAIPRLSVVRPADANETAYAWRTILARR
                      * .:.:*****:: .:*.*: :*::*  .*. *:*.  *  * .     .

sp|P29401|TKT_HUMAN   TK----GICFIRTSRPENAIIYNNNED-FQVGQAKV-----VLKSKDDQV
sp|P66963|TKT_STAAW   SESTPTSLVLTRQNLPVLDVPEDVVEEGVRKGAYTV-----YGSEETPEF
sp|P9WG25|TKT_MYCTU   NGSGPVGLILTRQGVPVLDGT---DAEGVARGGYVLSDAGGLQPGEEPDV
                      .     .: : * . *          : .  *   :         :  :.

sp|P29401|TKT_HUMAN   TVIGAGVTLHEALAAAELLKKEKINIRVLDP-----FTIKPLDRK-LILD
sp|P66963|TKT_STAAW   LLLASGSEVSLAVEAAKDLEKQGKSVRVVSMPNWNAFEQQSEEYKESVIP
sp|P9WG25|TKT_MYCTU   ILIATGSEVQLAVAAQTLLADNDILARVVSMPCLEWFEAQPYEYRDAVLP
                       ::.:*  :  *: *   *  .:    **:.      *  :. : :  ::

sp|P29401|TKT_HUMAN   S---ARATKGRILTVEDHYYEGGIGEAVSSAVVGEPGITVTHLAVNRVPR
sp|P66963|TKT_STAAW   SSVTKRVAIEMASPLGWHKYVGTAGK---------------VIAIDGFGA
sp|P9WG25|TKT_MYCTU   PTVSARVAVEAGVAQCWHQLVGDTGE---------------IVSIEHYGE
                      .    *.:     .   *   *  *:                ::::

sp|P29401|TKT_HUMAN   SGKPAELLKMFGIDRDAIAQAVRGLITKA
sp|P66963|TKT_STAAW   SAPGDLVVEKYGFTKENILNQVMSL----
sp|P9WG25|TKT_MYCTU   SADHKTLFREYGFTAEAVAAAAERALDN-
                      *.    :.. :*:  : :   .
```

```
sp|P29401|TKT_HUMAN   HCGVSIGEDGPSQMALEDLAMFRSVPTSTVFYPSDGVATEKAVELAA--N
sp|P66963|TKT_STAAW   HDSIAVGEDGPTHEPIEQLAGLRAIPNMNVIRPADGNETRVAWEVAL--E
sp|P9WG25|TKT_MYCTU   HDSIGLGEDGPTHQPIEHLSALRAIPRLSVVRPADANETAYAWRTILARR
                      * .:.:*****:: .:*.*: :*::*  .*. *:*.   *  * .    .
```

TKTμ: DLSSEVATHQPIIACLP (17aa)

M.tbTKT1: GEDGPTHQPIEHLSA (15 aa)

M.tbTKT2: DGPTHQPIEHLSALRAIPRLSV (22 aa)

M.tbTKT3: HDSIGLGEDGPTHQPIEHLS (20 aa)

FIG. 2B

FIG. 16A (part 1 of 3)

```
sp|P9WG25|TKT_MYCTU      MTTLEEISALTRPRHPDYWTEIDSAAVDTIRVLAADAVQKVGNGHPGTAM
tr|X8B9T3|X8B9T3_MYCAV   MTTLEEISALTQPHLPDDWSELDSAAVDTIRVLAADAVQKVGNGHPGTAM
                         ***********:*: ** *:*:****************************

sp|P9WG25|TKT_MYCTU      SLAPLAYTLFQRTMRHDPSDTHWLGRDRFVLSAGHSSLTLYIQLYLGGFG
tr|X8B9T3|X8B9T3_MYCAV   SLAPLAYTLFQRVMRHDPSDTHWLGRDRFVLSAGHSSLTLYLQLYLGGFG
                         ************.****************************:********

sp|P9WG25|TKT_MYCTU      LELSDIESLRTWGSKTPGHPEFRHTPGVEITTGPLGQGLASAVGMAMASR
tr|X8B9T3|X8B9T3_MYCAV   LELSDIESLRTWGSKTPGHPEFRHTKGVEITTGPLGQGLASAVGMAMASR
                         ************************ *************************

sp|P9WG25|TKT_MYCTU      YERGLFDPDAEPGASPFDHYIYVIASDGDIEEGVTSEASSLAAVQQLGNL
tr|X8B9T3|X8B9T3_MYCAV   YERGLFDPDAAAGTSPFDHFIYVIASDGDIEEGVTSEASSLAAVQQLGNL
                         **********  *.*****:******************************

sp|P9WG25|TKT_MYCTU      IVFYDRNQISIEDDTNIALCEDTAARYRAYGWHVQEVEGGENVVGIEEAI
tr|X8B9T3|X8B9T3_MYCAV   IVFYDHNQISIEDDTNIALCEDTAARYEAYGWHVQRVEGGENVVAIEEAI
                         *****:*********************.*******.********.*****
```

FIG. 16A (part 2 of 3)

```
sp|P9WG25|TKT_MYCTU      ANAQAVTDRPSFIALRTVIGYPAPNLMDTGKAHGAALGDDEVAAVKKIVG
tr|X8B9T3|X8B9T3_MYCAV   AAAKAVTDRPSFIELRTIIGYPAPNAMNTGKAHGAALGEEEVAAVKKILG
                         * *:********* ***:******* *:**********::********:*

sp|P9WG25|TKT_MYCTU      FDPDKTFQVREDVLTHTRGLVARGKQAHERWQLEFDAWARREPERKALLD
tr|X8B9T3|X8B9T3_MYCAV   FDPDKTFQVRDKVIAHTRKLVDRGREAHQKWQTDFDAWAQREPERKALLE
                         **********:.*: *** ** **::**::** :*****:*********:

sp|P9WG25|TKT_MYCTU      RLLAQKLPDGWDADLPHWEPGSKALATRAASGAVLSALGPKLPELWGGSA
tr|X8B9T3|X8B9T3_MYCAV   RLTAEKLPDGWDADLPHWEPGSDAIATRKASGAVLNAVAPKLPELWGGSA
                         ** *:*****************.*:*** ******.*:.***********

sp|P9WG25|TKT_MYCTU      DLAGSNNTTIKGADSFGPPSISTKEYTAHWYGRTLHFGVREHAMGAILSG
tr|X8B9T3|X8B9T3_MYCAV   DLAESNLTTINNADSFGPPSISTKEFTASWYGRVLHFGVREHAMGAILSG
                         *** ** ***:.*************:** ****.****************

sp|P9WG25|TKT_MYCTU      IVLHGPTRAYGGTFLQFSDYMRPAVRLAALMDIDTIYVWTHDSIGLGEDG
tr|X8B9T3|X8B9T3_MYCAV   IVLHGPTRAYGGTFLQFSDYMRPAVRLASLMDIDTIYVWTHDSIGLGEDG
                         ****************************:*********************
```

FIG. 16A (part 3 of 3)

```
sp|P9WG25|TKT_MYCTU       PTHQPIEHLSALRAIPRLSVVRPADANETAYAWRTILARRNGSGPVGLIL
tr|X8B9T3|X8B9T3_MYCAV    PTHQPIEHLAALRAIPKLSVVRPADANETAYAWRTILARGNGSGPVGLVL
                          *********:******:********************** ********:*

sp|P9WG25|TKT_MYCTU       TRQGVPVLDGTDAEGVARGGYVLSDAGGLQPGEEPDVILIATGSEVQLAV
tr|X8B9T3|X8B9T3_MYCAV    TRQGLPVLEGTDADGVARGGYILGS-DGEEAGQEPDVILIATGSEVQLAV
                          ****:***:****:*******:*..  *   *:*****************

sp|P9WG25|TKT_MYCTU       AAQTLLADNDILARVVSMPCLEWFEAQPYEYRDAVLPPTVSARVAVEAGV
tr|X8B9T3|X8B9T3_MYCAV    EAQKLLADKDIVARVVSMPCVEWFESQPDDYRDSVLPPSVSARVAVEAGV
                           **.****:**:********:****:** :***:****:***********

sp|P9WG25|TKT_MYCTU       AQCWHQLVGDTGEIVSIEHYGESADHKTLFREYGFTAEAVAAAAERALDN
tr|X8B9T3|X8B9T3_MYCAV    AQSWHKLVGDTGKIISIEHYGESADYKTLFREFGFTAEAVAAAAEEVVDN
                          **.**:******:*:**********:******:************..:**
```

FIG. 16B (part 1 of 3)

```
sp|P9WG25|TKT_MYCTU      MTTLEEISALTRPRHPDYWTEIDSAAVDTI-RVLAADAV---QKVGNGHP
tr|A0R0M3|A0R0M3_MYCS2   MNES--------------NDRIDTTLVGRLARQLRADAIRASTAAGSGHP

sp|P9WG25|TKT_MYCTU      GTAMSLAPLAYTLFQRTMRHDPSDTHWLGRDRFVLSAGHSSLTLYIQLYL
tr|A0R0M3|A0R0M3_MYCS2   TSSMSAADLTAVLLARHLSYDWERPDHPDNDHFILSKGHASPLLYAAFKA

sp|P9WG25|TKT_MYCTU      GGFGLELSDIESLRTWGSKTPGHPEFRHTPGVEITTGPLGQGLASAVGMA
tr|A0R0M3|A0R0M3_MYCS2   VGVITDTELMTGYRRFGSRLQGHPT-PVLPWVDVASGSLGQGIAIGVGVA

sp|P9WG25|TKT_MYCTU      MASRYE-RGLFDPDAEPGASPFDHYIYVIASDGDIEEGVTSEASSLAAVQ
tr|A0R0M3|A0R0M3_MYCS2   LAGKFLDRSGF-------------HVWTLCGDSEMAEGSVWEALDKAGYY

sp|P9WG25|TKT_MYCTU      QLGNLIVFYDRNQISIEDDTNIALC-EDTAARYRAYGWHVQEVEGGENVV
tr|A0R0M3|A0R0M3_MYCS2   GLSNFTVIVDVNRLGQRGPTEFGWDLETYAKRVEAFGARAISVDG-HRLE
```

FIG. 16B (part 2 of 3)

```
sp|P9WG25|TKT_MYCTU       GIEEAIANAQAVTDRPSFIALRTVIGYPAPNLMDTGKAHGAALGDDEVAA
tr|A0R0M3|A0R0M3_MYCS2    AIDQALTAARN-TTQPTVILARTVKGRGFSEVEDREGWHGKAFPP-----

sp|P9WG25|TKT_MYCTU       VKKIVGFDPDKTFQVREDVLTHTRGLVARGKQAHERWQLEFDAWARREPE
tr|A0R0M3|A0R0M3_MYCS2    ---------EMARRAL-AELGEVEGL----------------TVAGPKPA

sp|P9WG25|TKT_MYCTU       RKALLDRLLAQKLPDGWDADLPHWEPGSKALATRAASGAVLSALGPKLPE
tr|A0R0M3|A0R0M3_MYCS2    SRSGQSSAPGAGNPDGF-SDRPRYAPGEK-VATRAAYGAAVAALGAV---

sp|P9WG25|TKT_MYCTU       LWGGSADLAGSNNTTIKGADSFGPPSISTKEYTAHWYGRTLHFGVREHAM
tr|A0R0M3|A0R0M3_MYCS2    ------------NRRVVALDGEVSNSTGAAEFTEHHPERYFEMFIAEQQL

sp|P9WG25|TKT_MYCTU       GAILSGIVLHGP-TRAYGGTFLQFSDYMRPAVRLAALMDIDTIYVWTHDS
tr|A0R0M3|A0R0M3_MYCS2    VASSVGL--HVRHYIPFASTFAAFLTRAHDFIRMAAVSQANICLIGSHAG
```

FIG. 16B (part 3 of 3)

```
sp|P9WG25|TKT_MYCTU       IGLGEDGPTHQPIEHLSALRAIPRLSVVRPADANETAYAWRTILARRNGS
tr|A0R0M3|A0R0M3_MYCS2    VEIGADGPSQMALEDLAMMRSVHGATVLYPSDATSTV-ALVDLMADAD--
                          : :* ***:: .:*.*: :*::   :*: *:**..*. *   ::*  :

sp|P9WG25|TKT_MYCTU       GPVGLILTRQGVPVLDGTDAEGVARGGYVLSDAGGLQPGEEPDVILIATG
tr|A0R0M3|A0R0M3_MYCS2    GVRYLRTTRGAYPVLYEPATVFT------IGGSHTLRSSSADDVTLIGAG
                          *   *  ** . ***  . :  .      :..:  *:...  ** **.:*

sp|P9WG25|TKT_MYCTU       SEVQLAVAAQTLLADNDILARVVSMPCLEWFEAQPYEYRDAVLPPTV--S
tr|A0R0M3|A0R0M3_MYCS2    VTVHQCLAAAESLHRDGIAARVIDVY-----SVKPID-RDTLLEAVRDTG
                            *: .:**   *  :.* ***:.:       ..:* : **::* ..   .

sp|P9WG25|TKT_MYCTU       ARV-----------------------------------------------
tr|A0R0M3|A0R0M3_MYCS2    ARLVIAEDHHPEGGLGSAVLEAISGAETPRLKLMHLAVRAMPGSGTPAEL
                          **:

sp|P9WG25|TKT_MYCTU       ----AVEAG--VAQCWHQLVGDTGEIVSIEHYGESADHKTLFREYGFTAE
tr|A0R0M3|A0R0M3_MYCS2    LADAAIDAASIDKAARHLLQADDGR----SDDGRSDDDETLTA-------
                              *::*.     . * * .* *.    .. *.* *.:**

sp|P9WG25|TKT_MYCTU       AVAAAAERALDN
tr|A0R0M3|A0R0M3_MYCS2    ------------
```

FIG. 16C (part 1 of 3)

```
sp|P9WG25|TKT_MYCTU      MTTL--------EEISALTRPRHPDYWTEIDSAAVDTIRVLAADAVQKVG
tr|B1MC67|B1MC67_MYCA9   MTAISRELAEVPTDIPTLTRVDHPDDWTELDSRAVDTVRVLAADAVQKVG
                         **::         :*.:***  *** ***:** ****:************

sp|P9WG25|TKT_MYCTU      NGHPGTAMSLAPLAYTLFQRTMRHDPSDTHWLGRDRFVLSAGHSSLTLYI
tr|B1MC67|B1MC67_MYCA9   NGHPGTAMSLAPVAYTLFQRQLRHDPSDTTWIGRDRFVLSCGHSSLTLYL
                         ************:******* :******* *:********.********:

sp|P9WG25|TKT_MYCTU      QLYLGGFGLELSDIESLRTWGSKTPGHPEFRHTPGVEITTGPLGQGLASA
tr|B1MC67|B1MC67_MYCA9   QLYLGGFGLELSDIEALRTWGSLTPGHPEYHHTKGVEITTGPLGQGLASA
                         ***************:****** ******::** ****************

sp|P9WG25|TKT_MYCTU      VGMAMASRYERGLFDPDAEPGASPFDHYIYVIASDGDIEEGVTSEASSLA
tr|B1MC67|B1MC67_MYCA9   VGMAMASRYERGLFDPDAAPGTSPFDHFIYVIASDGDIEEGVTSEASSLA
                         ****************** **:*****:**********************

sp|P9WG25|TKT_MYCTU      AVQQLGNLIVFYDRNQISIEDDTNIALCEDTAARYRAYGWHVQEVEGGEN
tr|B1MC67|B1MC67_MYCA9   GTQQLGNLIVIWDDNEISIEHDTKIALSEDTPARYEAYGWHVQTVVSGEN
                         ..********::* *:****.**:***.***.***.******* * .***
```

FIG. 16C (part 2 of 3)

```
sp|P9WG25|TKT_MYCTU      VVGIEEAIANAQAVTDRPSFIALRTVIGYPAPNLMDTGKAHGAALGDDEV
tr|B1MC67|B1MC67_MYCA9   VTGLEEALANARAVTDRPSFIALRTIIGYPAPTKMNTGGVHGSALGADEV
                         *.*:***:***:*************:******. *:** .**:*** ***

sp|P9WG25|TKT_MYCTU      AAVKKIVGFDPDKTFQVREDVLTHTRGLVARGKQAHERWQLEFDAWARRE
tr|B1MC67|B1MC67_MYCA9   AATKKILGFDPDKSFEVAPEVIAHTRELVTRGKQAHAEWDKSFEAWAARE
                         **.***:******:*:*   :*::*** **:****** .*: .*:*** **

sp|P9WG25|TKT_MYCTU      PERKALLDRLLAQKLPDGWDADLPHWEPGSKALATRAASGAVLSALGPKL
tr|B1MC67|B1MC67_MYCA9   PERKALLDRLQARALPQGWDAGLPSWEPGSKAVATRAASGDTLSALGAKL
                         ********** *: **:****.** *******:******* .*****.**

sp|P9WG25|TKT_MYCTU      PELWGGSADLAGSNNTTIKGADSFGPPSISTKEYTAHWYGRTLHFGVREH
tr|B1MC67|B1MC67_MYCA9   PELWGGSADLAGSNNTTIKGADSFGPTSIATSDWNAQPYGRTLHFGIREH
                         **************************.**:*.::.*: ********:***

sp|P9WG25|TKT_MYCTU      AMGAILSGIVLHGPTRAYGGTFLQFSDYMRPAVRLAALMDIDTIYVWTHD
tr|B1MC67|B1MC67_MYCA9   AMGSILSGIVLHGPTRAYGGTFLQFADYMRPAVRLAALMNIDPIYVWTHD
                         ***:*********************:*************:**.*******
```

FIG. 16C (part 3 of 3)

```
sp|P9WG25|TKT_MYCTU        SIGLGEDGPTHQPIEHLSALRAIPRLSVVRPADANETAYAWRTILARRNG
tr|B1MC67|B1MC67_MYCA9     SIGLGEDGPTHQPVEHLAALRAIPNLSVVRPGDANETAYAWATVLERQSS
                           *************:***:******.******.********* *:* *:..

sp|P9WG25|TKT_MYCTU        SGPVGLILTRQGVPVLDGTDAEGVARGGYVLSDAGGLQPGEEPDVILIAT
tr|B1MC67|B1MC67_MYCA9     TGPVGLALTRQGVPILEGTSREGVAKGGYVLE-AASDNPADAPDVILIGT
                           :***** *******:*:**. ****:*****. *.. :*.: ******.*

sp|P9WG25|TKT_MYCTU        GSEVQLAVAAQTLLADNDILARVVSMPCLEWFEAQPYEYRDAVLPPTVSA
tr|B1MC67|B1MC67_MYCA9     GSELQLAVEAKKILAAKGIAASVVSLPCVEWFESQPQEYRDSVLPPSVRA
                           ***:**** *:.:** :.* * ***:**:****:** ****:****:* *

sp|P9WG25|TKT_MYCTU        RVAVEAGVAQCWHQLVGDTGEIVSIEHYGESADHKTLFREYGFTAEAVAA
tr|B1MC67|B1MC67_MYCA9     RVVVEAGIAQGWYKFVGDAGQIVSLEHFGASADDKTLFREFGFTPDAVAA
                           **.****:** *:::***.*:***:**:* ***.******:*** .:****

sp|P9WG25|TKT_MYCTU        AAERALDN--
tr|B1MC67|B1MC67_MYCA9     AAERSIAAAQ
                           ****::
```

TRANSKETOLASE EPITOPES, METHODS, AND DEVICES FOR IGG-BASED *TUBERCULOSIS* SERODIAGNOSIS

CROSS-REFERENCE TO RELATED APPLICATION

This application claims priority to and the benefit of the earlier filing of U.S. Provisional Application No. 63/478,080, filed on Dec. 30, 2022, which is incorporated by reference herein in its entirety.

STATEMENT REGARDING FEDERALLY SPONSORED RESEARCH OR DEVELOPMENT

This invention was made with government support under contracts R01HL113508, R01 HL150474, and R21 HL148089, each awarded by the National Institutes of Health. The government has certain rights in the invention.

INCORPORATION BY REFERENCE OF SEQUENCE LISTING

A computer readable text file, entitled "W063-0093US Sequence Listing_ST26.XML" created on or about Dec. 29, 2023, with a file size of 22,458 bytes, contains the sequence listing for this application and is hereby incorporated by reference in its entirety.

FIELD OF THE DISCLOSURE

The present disclosure relates generally to methods and systems for diagnosis, and more specifically ELISA-based serodiagnostic methods and devices for tuberculosis.

BACKGROUND OF THE DISCLOSURE

Active *Mycobacterial tuberculosis* infection (TB) remains a global health threat with 10 million new cases and 1.7 million deaths annually (Lawn et al., *Lancet,* 378(9785): 57-72, 2011; Nahid et al., *Am. J. Respir. Crit.,* 184(8): 972-9, 2011). One third of the world's population is infected with TB but not all are considered to have latent TB infection (LTBI) (Nahid et al., *Am. J. Respir. Crit.,* 184(8): 972-9, 2011). Pulmonary TB is contagious and can be lethal and LTBI can evolve into active TB (Lawn et al., *Lancet,* 378(9785): 57-72, 2011). The discovery of specific biomarkers in form of antibodies distinguishing the immunity in active TB and LTBI could be the key to understanding the humoral responses against mycobacterial pathogens. Current commercially available antibody-based TB tests show poor sensitivity and specificity, and none can distinguish active TB from LTBI (Steingart et al., *PLOS Med,* 4(6): e202, 2007).

Serological diagnosis of tuberculosis has been challenging, partly due to large M.tb proteome and even larger antigenic epitopes (Denkinger et al., *J Infect Dis,* 220:S91-S8, 2019), and heterogeneity across humans in immunoglobulin G (IgG) response to tuberculosis (Achkar et al., *Cell Host Microbe,* 13:250-62, 2013). Most tuberculosis serological tests use purified M.tb proteins, a single or small number of antigens, predominantly derived from membrane proteins of M.tb (Steingart et al., *PLOS Med,* 4(6): e202, 2007).

Current non-sputum based POCs either detect various M.tb antigens, including lipoarabinomannan (LAM), culture filtrate proteins (CFPs), and ESAT-6, or detect host antibody responses to M.tb (Hong et al., Sci Transl Med, 14:eabj4124, 2022; Peter et al., *Lancet,* 387:1187-97, 2016). Sensitivities and specificities of antigen-based POCs are lower than the ideal and variable based on the patient population, including hospitalized patients versus outpatient or HIV status (Hong et al., Sci Transl Med, 14:eabj4124, 2022; World Health Organization, Lateral flow urine lipoarabinomannan assay (LF-LAM) for the diagnosis of active tuberculosis in people living with HIV: policy update (2019): evidence to decision tables. 2019). Among these tests, WHO endorsed lateral flow urine LAM assay to aid TB disease diagnosis in HIV-positive patients (World Health Organization, Lateral flow urine lipoarabinomannan assay (LF-LAM) for the diagnosis of active tuberculosis in people living with HIV: policy update (2019): evidence to decision tables. 2019). LAM is a ubiquitous mycobacterial component, has low specificity for distinguishing M.tb from nontuberculous mycobacteria (NTM) that is important in HIV infected subjects (Liu et al., Int J Infect Dis, 118:65-70, 2022). There are few serological tests available that quantitate the TB specific antibodies in the serum. The InBios Active Tb Detect IgG ELISA assay that uses pool of M.tb antigens was found to be sensitive to detect active TB (Omrani et al., Pak J Biol Sci. 12(4):373-377, 2009; Welch et al., Clin Vaccine Immunol, 19(4): 522-526, 2012). Other available tests for TB serodiagnosis utilizing various components of M.tb, including, Ag60 complex (Grubek-Jaworska et al., Int J Tuberc Lung Dis, 1(6): 556-562, 1997; Alifano et al., Thorax 53(5): 377-80, 1998), PPD (Zeiss et al., Rev Respir Dis, 130(5): 845-848, 1984) or a pool of membrane and secreted antigens from M.tb H37Rv (Målen et al., Scand J Immunol, 67(3): 245-52, 2008). Most these tests utilized either a single specific antigen or a pool of membrane or secreted M.tb antigens containing various potential epitopes. Only a few studies included LTBI to assess specificity and sensitivity (Wang et al., Int J Infect Dis, 70:1-9, 2018).

There are also challenges for the development of effective serological tests include the need to differentiate active pulmonary TB from other pulmonary diseases, including pneumonia or other granulomatous disease such as pulmonary sarcoidosis, a non-infectious systemic granulomatous disease with remarkable similarity to TB in clinical, immune responses, and in gene expression signatures (Maertzdorf et al., *Genes Immun,* 12:15-22, 2011; Maertzdorf et al., *Proc Natl Acad Sci USA,* 109:7853-7858, 2012; Oswald-Richter et al., *J Clin Immunol,* 30:157-166, 2010; Blankley et al., *PloS One,* 11:e0162220, 2016).

SUMMARY OF ASPECTS OF THE DISCLOSURE

Described herein is the discovery of a peptide sequence with homology to Mycobacterial tuberculosis' transketolase (M.tb TKT), and that serum IgGs of active TB patients differentially bind to this antigen-clones. Through sequence alignment and in silico analysis, designed two additional peptides (M.tb-TKT1 and M.tb-TKT3) were with antigenicity corresponding to M.tb-specific transketolase epitopes. Also described is the development of direct ELISA systems to detect IgG against specific TKT antigen clones (TKTμ, M.tb-TKT1 and M.tb-TKT3).

Also described is an ELISA system, and its testing against a large set of subjects with positive and negative controls—the results described herein show the ELISA system has high sensitivity, specificity, and accuracy.

An exemplary embodiment is a method of detecting antibodies that specifically bind a *Mycobacterium tubercu-*

*losis* (M.tb) peptide in a sample of a subject suspected of having an M.tb infection, the method including detecting in the sample the presence of an antibody that reacts with (specifically binds to) a peptide including (or having) the sequence of SEQ ID NO: 1, SEQ ID NO: 12 (TKTμ; DLSSEVATHQPIIACLP), SEQ ID NO: 3 (TKT1; GEDGPTHQPIEHLSA), or SEQ ID NO: 5 (TKT3; HDSIGLGEDGPTHQPIEHLS). Such detection can include performing an enzyme-linked immunoassay (such as an enzyme-linked immunosorbent assay (ELISA)), a radioimmunoassay, an immunoprecipitation, a fluorescence immunoassay, a chemiluminescent assay, an immunoblot assay, a lateral flow assay, a flow cytometry assay, a multi-plex particle-based suspension array assay, a mass spectrometry assay, or a particulate-based assay. In examples, the sample is serum, and the serum is diluted more than 1:50, 1:250 to 1:16000, 1:400-1:1000, or 1:500, serum to dilution agent.

Also provided are methods for aiding in the diagnosis of active *Mycobacterium tuberculosis* (M.tb) infection in a subject, the methods including: contacting a sample from the subject with a peptide including the sequence of SEQ ID NO: 1, 12, 3, or 5 under conditions suitable for an anti-transketolase (TKT) antibody in the sample to form a complex with the peptide; detecting a level of formation of the complex using an enzyme-linked immunosorbent (ELISA) assay including a detecting antibody, wherein the detecting antibody is a horseradish peroxidase (HRP) conjugated anti-human IgG antibody, and a substrate to detect HRP, thereby determining the level of the anti-transketolase antibody in the sample; and comparing the level of antibody in the sample to a control level, wherein the difference in the level of antibody in the sample relative to the control level is indicative of an increased likelihood of the subject having active M.tb infection.

Also provided are immunoassay kit embodiments, which kits are useful for selectively detecting anti-transketolase antibody in a biological sample. Such kits include, as capture reagent, a peptide including (or alternatively, consisting of) the sequence of SEQ ID NO: 1, 12, 3 or 5, wherein the peptide forms a complex with an anti-transketolase antibody in the biological sample; and as detection reagent, a detectable anti-human IgG antibody, wherein the detectable anti-human IgG antibody binds to anti-transketolase antibody in the complex. Optionally, kit embodiments may further include a solid support for the capture reagent.

Additional embodiments are disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) TKTμ-specific IgGs were measured via standardized direct TKT peptide ELISA. OD value at 450 nm was a measure of TKTμ-specific IgGs in the sera from all study group; healthy controls (n=66), sarcoid (n=76), smear positive TB subjects (n=101) and LTBI (n=49) via ELISA. TB patients showed significantly higher OD values for as compared to healthy controls (p=4.26e-19), sarcoidosis (p=1.63e-18) and LTBI (p=4.26e-19). (FIG. 1B) Polyclonal anti-TKTμ IgGs were generated by immunizing the rabbits with TKTμ peptide and was used to obtain a standard curve for TKTμ peptide ELISA. Anti-TKTμ IgG standard curve showing OD at 450 nm versus anti-TKTμ IgG concentration (ng/ml). (FIG. 1C) Anti-TKTμ IgG concentration (ng/ml) in all study groups; TB patients displayed significantly higher levels of serum TKTμ IgGs (10.8±7.25) as compared to control (2.7±1.32), sarcoid (2.9±1.77) and LTBI (2.7±0.821). After the correction of p value for multiple comparison the TKTμ IgGs levels in TB sera were significantly difference as compared to control (p=1.63e-18), sarcoid (p=1.63e-18) or LTBI (p=4.26e-19).

FIGS. 2A-2B. Sequence alignment of TKT from *Mycobacterium tuberculosis, Staphylococcus aureus*, and *Homo sapiens*. The amino acid sequences of TKT for all three species were obtained from UniProtKB: P9WG25 (TKT_MYCTU; SEQ ID NO: 8), A0A0B4J1R6 (TKT_HUMAN; SEQ ID NO: 6), Q6G9L6 (TKT_STAAW; SEQ ID NO: 7). The sequence alignment and homology of TKT was done by using T-Coffee Multiple Sequence Alignment program. (FIG. 2A; in three parts) CLUSTALW (1.83) multiple sequence alignment. Identical residues in all three species are indicated by red, identical residues in M.tb and *S. aureus* are indicated by green. (FIG. 2B) Sequence of TKTμ (SEQ ID NOs: 9, 10, and 11 in top-to-bottom order) and designed peptides, M.tb TKT1 (SEQ ID NO: 3), M.tb TKT2 (SEQ ID NO: 4) and M.tb TKT3 (SEQ ID NO: 5), corresponding to M.tb TKT epitopes. Discovered TKTμ peptide (17aa) shows a sequence similarity of THQPI AAs with M.tb TKT.

(FIG. 4A) OD for IgGs against M.tb TKT1 shown as (Mean±SD). TB sera (0.6±0.39), healthy controls (0.2±0.11), Sarcoidosis (0.2±0.08) and LTBI (0.4±0.24). As shown TB sera display significantly higher ODs as compared to controls (p=8.8e-16), sarcoid (p=5.58e-16) and LTBI (p=1.35e-5). (FIG. 4B) OD for IgGs against M.tb TKT3 shown as (Mean±SD). TB sera (0.6±0.35), healthy controls (0.2±0.07), Sarcoidosis (0.2±0.05) and LTBI (0.3±0.18). TB sera exhibited significantly higher ODs of IgGs against M.tb TKT3 as compared to controls (adj p=2.76e-22), sarcoid (adj p=2.76e-22) and LTBI (adj p=1.44e-10).

(FIGS. 5B-5D) The model from training set was validated on the test set (40% of samples) by applying the thresholds in term of sensitivity, specificity, positive predictive value, negative predictive value, and accuracy. Panels shows the performance of TKTμ (FIG. 5B) M.tb TKT3 (FIG. 5C), and M.tb TKT1 (FIG. 5D) values on the test set indicating the area under the curve (AUC) for each ROCs. The red dot on each ROC curve (FIGS. 5B-5D) and its coordinates in the parentheses represent the optimal OD cut-off points, which is the point on the ROC curve closest to (0,1) in term of 1-specificity and sensitivity. The OD value corresponding to this cut point is considered as the threshold to determine a TB infected sample, i.e. a sample is classified as TB infection if its serum value is greater than or equal to this the corresponding threshold.

(FIG. 11A) TKTμ-specific IgGs were measured via standardized direct TKT peptide ELISA in the sera from all study group; healthy controls (n=122), sarcoidosis (n=98), LTBI (n=50), LC (n=30), TB (n=148) and NTM (n=62) subjects via ELISA. OD value at 450 nm was a measure of TKTμ-specific IgGs. TB patients showed significantly higher OD values for as compared to healthy controls (p=2.76e-42), sarcoidosis (p=2.57e-37), LTBI (p=1.72e-24), LC (p=4.65e-17) and NTM (p=1.61e-24). (FIG. 11B) Anti-TKTμ IgG concentration was determined using Anti-TKTμ IgG standard curve. TB patients displayed significantly higher levels of serum TKTμ IgGs, mean±1 SD, (12.84±5.65 μg/mL) as compared to control (2.78±1.65), sarcoidosis (2.82±1.77 μg/mL), LC (3.96±1.21 μg/mL), LTBI (2.93±2.05 μg/mL) and NTM (4.77±2.07 μg/mL). (FIG. 11C) The TKT1 specific IgGs were measured via standardized direct TKT1 peptide ELISA. TB patients showed significantly higher OD values for TKT1 IgGs as compared to healthy controls (p=3.39e-30), sarcoidosis (p=6.50e-27), LTBI (p=6.66e-11), LC (p=6.68e-11) and NTM (p=3.63e-09). (FIG. 11D) The TKT3 specific IgGs were measured via standardized direct TKT3 peptide ELISA. TB patients showed significantly higher OD values for TKT3 IgGs as compared to healthy controls (p=4.13e-38), sarcoidosis (p=3.79e-35), LTBI (p=1.38e-14), LC (p=1.93e-14) and NTM (p=1.40e-10).

(FIG. 12A) ROC curves for anti-TKTμ IgG were generated by using 10-fold cross validation (CV). CV models were obtained from the entire dataset. (FIG. 12A) TKTμ ROC curve yielded an area under curve (AUC) of 0.983, 0.970, 0.985, 0.983, 0.956, 0.991, 0.984, 0.975, 0.963, and 0.994. DTs for TKTμ with data excluding NTM (FIG. 12B) DT first trained with 75% of the data (FIG. 12C) Pruned DT for TKTμ based on misclassification or deviance. The best model that had a higher accuracy and/or predicted TB and NTM was selected. DTs for TKTμ with data including NTM (FIG. 12D) DT first trained with 75% of the data (FIG. 12E) Pruned DT for TKTμ based on misclassification or deviance. The best model that had a higher accuracy and/or predicted TB and NTM was selected.

(FIG. 13A) ROC curves for anti-TKT1 IgG were generated by using 10-fold cross validation (CV). CV models were obtained from the entire dataset. (FIG. 13A) TKT1 ROC curve yielded an area under curve (AUC) of 0.852, 0.822, 0.951, 0.831, 0.867, 0.844, 0.988, 0.813, 0.768, and 0.903. DTs for TKT1 with data excluding NTM (FIG. 13B) DT first trained with 75% of the data (FIG. 13C) Pruned DT for TKT1 based on misclassification or deviance. DTs for TKT1 with data including NTM (FIG. 13D) DT first trained with 75% of the data (FIG. 13E) Pruned DT for TKT1 based on misclassification or deviance. The best model that had a higher accuracy and/or predicted TB and NTM was selected.

(FIG. 14A) ROC curves for anti-TKT3 IgG were generated by using 10-fold cross validation (CV). CV models were obtained from the entire dataset. (FIG. 14A) TKT3 ROC curve yielded an area under curve (AUC) of 0.896, 0.869, 0.963, 0.883, 0.893, 0.965, 0.941, 0.906, 0.924, and 0.939. DTs for TKT3 with data excluding NTM (FIG. 14B) DT first trained with 75% of the data (FIG. 14C) Pruned DT for TKT3 based on misclassification or deviance. DTs for TKT3 with data including NTM (FIG. 14D) DT first trained with 75% of the data (FIG. 14E) Pruned DT for TKT3 based on misclassification or deviance. The best model that had a higher accuracy and/or predicted TB and NTM was selected.

(FIG. 15A) ROC curves for combined markers TKTμ+TKT1+TKT3 were generated by using 10-fold cross validation (CV). CV models were obtained from the entire dataset. (FIG. 15A) TKT3 ROC curve yielded an area under curve (AUC) of 0.983, 0.961, 0.991, 0.968, 0.966, 0.993, 0.986, 0.975 0.958, and 0.985. DTs for TKTμ+TKT1+TKT3 with data excluding NTM (FIG. 15B) DT first trained with 75% of the data (FIG. 15C) Pruned DT for TKT3. DTs for TKTμ+TKT1+TKT3 with data including NTM (FIG. 15D) DT first trained with 75% of the data (FIG. 15E) Pruned DT for TKT3 based on misclassification or deviance. The best model that had a higher accuracy and/or predicted TB and NTM was selected.

FIGS. 16A-16C: Sequence alignments of TKT from various *Mycobacterium* species. The sequence alignment and homology of TKT was done by using T-Coffee Multiple Sequence Alignment program. The amino acid sequences of TKT for all species were obtained from UniProtKB. (FIG. 16A; in three parts) Sequence alignment of TKT from *Mycobacterium tuberculosis* (UniProtKB: P9WG25, TKT_MYCTU; SEQ ID NO: 8), and *Mycobacterium avium* (UniProtKB: X8B9T3, X8B9T3_MYCAV; SEQ ID NO: 18). (FIG. 16B; in three parts) Sequence alignment of TKT from *Mycobacterium tuberculosis* (UniProtKB: P9WG25, TKT_MYCTU; SEQ ID NO: 8), and *Mycobacterium smegmatis* (UniProtKB: AOROM3, AOROM3_MYCS2; SEQ ID NO: 19). (FIG. 16C; in three parts) Sequence alignment of TKT from *Mycobacterium tuberculosis* (UniProtKB: P9WG25, TKT_MYCTU; SEQ ID NO: 8), and *Mycobacterium abscessus* (UniProtKB: B1MC67, B1MC67_MYCA9; SEQ ID NO: 20).

REFERENCE TO SEQUENCE LISTING

Figure 1A:
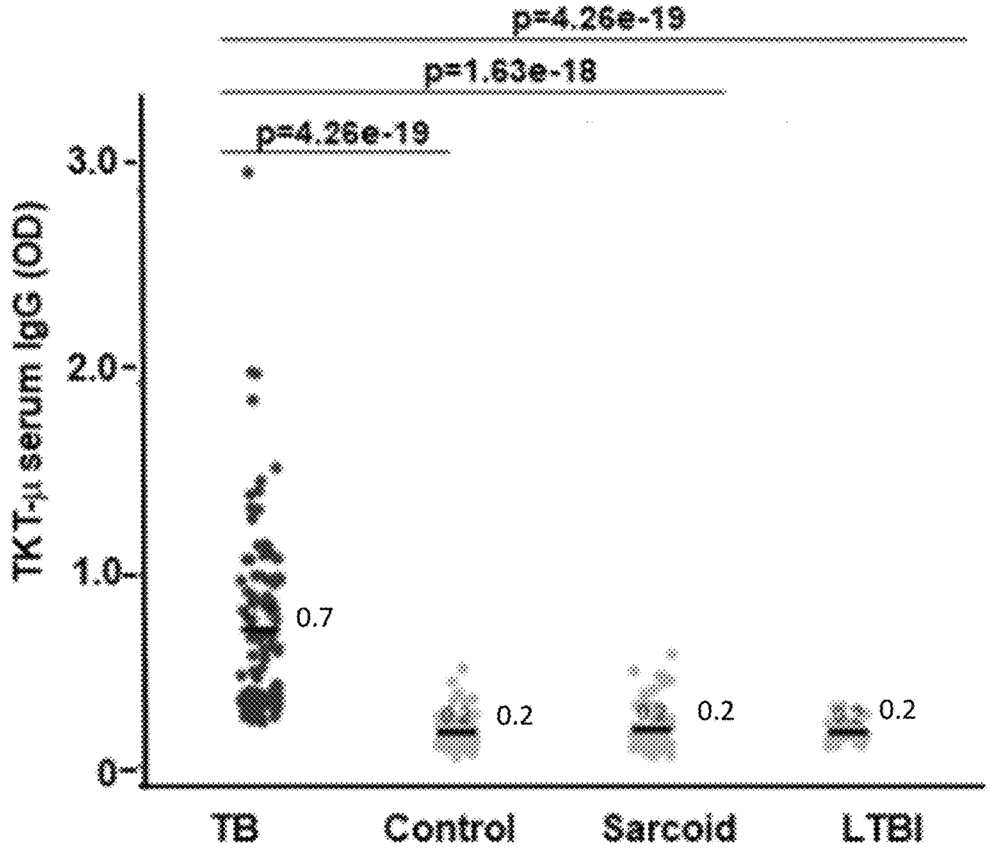
FIGS. 1A-1C. Detection and quantification of TKTμ-specific IgGs.

The nucleic acid and/or amino acid sequences described herein are shown using standard letter abbreviations, as defined in 37 C.F.R. § 1.822. Only one strand of each nucleic acid sequence is shown, but the complementary strand is understood as included in embodiments where it would be appropriate. In the Sequence Listing:

SEQ ID NO: 1 is a core part of a M.tb transketolase sequence:
THQPI

SEQ ID NO: 2 is an open reading frame sequence of a M.tb transketolase:
THDSIGLGEDGPTHQPIE SEQ ID NO: 3 is a synthesized TKT1 sequence:
GEDGPTHQPIEHLSA SEQ ID NO: 4 is a synthesized TKT2 sequence:
DGPTHQPIEHLSALRAIPRLSV SEQ ID NO: 5 is a synthetized TKT3 sequence:
HDSIGLGEDGPTHQPIEHLS SEQ ID NO: 6 is the amino acid sequence of a *Homo sapiens* TKT obtained from UniProtKB: A0A0B4J1R6 (TKT_HUMAN),
MAFASIYKLDNLVAILDINRLGQSDPAPLQHQMDIYQKRCEAFGWHAIIVDGHSVEELCKAFGQ

AKHQPTAIIAKTFKGRGITGVEDKESWHGKPLPKNMAEQIIQEIYSQIQSKKKILATPPQEDAPSV

DIANIRMPSLPSYKVGDKIATRKAYGQALAKLGHASDRIIALDGDTKNSTFSEIFKKEHPDRFIEC

YIAEQNMVSIAVGCATRNRTVPFCSTFAAFFTRAFDQIRMAAISESNINLCGS*HCGVSIGEDGPS*

*QMALEDLAMFRSVPTSTVFYPSDGVATEKAVELAAN*TKGICFIRTSRPENAIIYNNNEDFQVGQ

AKVVLKSKDDQVTVIGAGVTLHEALAAAELLKKEKINIRVLDPFTIKPLDRKLILDSARATKGRILT

VEDHYYEGGIGEAVSSAVVGEPGITVTHLAVNRVPRSGKPAELLKMFGIDRDAIAQAVRGLITKA

SEQ ID NO: 7 is the amino acid sequence of a *Staphylococcus aureus* TKT obtained from UniProtKB: Q6G9L6 (TKT_STAAW),
MFNEKDQLAVDTLRALSIDTIEKANSGHPGLPMGAAPMAYTLWTRHLNFNPQSKDYFNRDRFV

LSAGHGSALLYSLLHVSGSLELEELKQFRQWGSKTPGHPEYRHTDGVEVTTGPLGQGFAMSV

GLALAEDHLAGKFNKEGYNVVDHYTYVLASDGDLMEGISHEAASFAGHNKLSKLVVLYDSNDIS

LDGELNKAFSENTKARFEAYGWNYLLVKDGNDLEEIDKAITTAKSQEGPTIIEVKTTIGFGSPNK

AGTNGVHGAPLGEVERKLTFENYGLDPEKRFNVSEEVYEIFQNTMLKRANEDESQWNSLLEKY

AETYPELAEEFKLAISGKLPKNYKDELPRFELGHNGASRADSGTVIQAISKTVPSFFGGSADLAG

SNKSNVNDATDYSSETPEGKNVWFGVREFAMGAAVNGMAAHGGLHPYGATFFVFSDYLKPA

LRLSSIMGLNATFIFT*HDSIAVGEDGPTHEPIEQLAGLRAIPNMNVIRPADGNETRVAWEVALES*

ESTPTSLVLTRQNLPVLDVPEDVVEEGVRKGAYTVYGSEETPEFLLLASGSEVSLAVEAAKDLE

KQGKSVRVVSMPNWNAFEQQSEEYKESVIPSSVTKRVAIEMASPLGWHKYVGTAGKVIAIDGF

GASAPGDLVVEKYGFTKENILNQVMSL

SEQ ID NO: 8 is the amino acid sequence of a *Mycobacterium tuberculosis* TKT obtained from UniProtKB: P9WG25 (TKT_MYCTU),
MTTLEEISALTRPRHPDYWTEIDSAAVDTIRVLAADAVQKVGNGHPGTAMSLAPLAYTLFQRTM

RHDPSDTHWLGRDRFVLSAGHSSLTLYIQLYLGGFGLELSDIESLRTWGSKTPGHPEFRHTPG

VEITTGPLGQGLASAVGMAMASRYERGLFDPDAEPGASPFDHYIYVIASDGDIEEGVTSEASSL

AAVQQLGNLIVFYDRNQISIEDDTNIALCEDTAARYRAYGWHVQEVEGGENVVGIEEAIANAQA

VTDRPSFIALRTVIGYPAPNLMDTGKAHGAALGDDEVAAVKKIVGFDPDKTFQVREDVLTHTRG

LVARGKQAHERWQLEFDAWARREPERKALLDRLLAQKLPDGWDADLPHWEPGSKALATRAA

SGAVLSALGPKLPELWGGSADLAGSNNTTIKGADSFGPPSISTKEYTAHWYGRTLHFGVREHA

MGAILSGIVLHGPTRAYGGTFLQFSDYMRPAVRLAALMDIDTIYVWT*HDSIGLGEDGPTHQPIEH*

*LSALRAIPRLSVVRPADANETAYAWRTILARR*NGSGPVGLILTRQGVPVLDGTDAEGVARGGYV

LSDAGGLQPGEEPDVILIATGSEVQLAVAAQTLLADNDILARVVSMPCLEWFEAQPYEYRDAVL

PPTVSARVAVEAGVAQCWHQLVGDTGEIVSIEHYGESADHKTLFREYGFTAEAVAAAAERALD

N

-continued

SEQ ID NO: 9 is the amino acid sequence of a *Homo sapiens* TKTμ, corresponding to positions 250-297 within SEQ ID NO: 6,
HCGVSIGEDGPSQMALEDLAMFRSVPTSTVFYPSDGVATEKAVELAAN SEQ ID NO: 10 is the amino acid sequence of a *Staphylococcus aureus* TKTμ, corresponding to positions 460-540 within SEQ ID NO: 7,
HDSIAVGEDGPTHEPIEQLAGLRAIPNMNVIRPADGNETRVAWEVALE SEQ ID NO: 11 is the amino acid sequence of a *Mycobacterium tuberculosis* TKTμ, corresponding to positions 491-540 within SEQ ID NO: 8,
HDSIGLGEDGPTHQPIEHLSALRAIPRLSVVRPADANETAYAWRTILARR SEQ ID NO: 12 is a synthesized TKTμ sequence:
DLSSEVATHQPIIACLP SEQ ID NO: 13 is a synthesized Mav1 sequence:
THQPIEHLAALRAIPKLSVVRP SEQ ID NO: 14 is a synthesized Mav2 sequence:
GEDGPTHQPIEHLAALRAIPKLSVVRP SEQ ID NO: 15 is a synthesized Mav3 sequence:
HDSIGLGEDGPTHQPIEHLAALRAIPKLSVVRP SEQ ID NO: 16 is a synthesized peptide sequence:
HLAALRAIPKLSVVRP SEQ ID NO: 17 is a *M. abscesses* TKT peptide sequence:
HDSIGLGEDGPTHQPVEHLA SEQ ID NO: 18 the amino acid sequence of a TKT from *Mycobacterium avium* obtained from UniProtKB: X8B9T3 (X8B9T3_MYCAV),
MTTLEEISALTQPHLPDDWSELDSAAVDTIRVLAADAVQKVGNGHPGTAMSLAPLAYTLFQRV

MRHDPSDTHWLGRDRFVLSAGHSSLTLYLQLYLGGFGLELSDIESLRTWGSKTPGHPEFRHTK

GVEITTGPLGQGLASAVGMAMASRYERGLFDPDAAAGTSPFDHFIYVIASDGDIEEGVTSEASS

LAAVQQLGNLIVFYDHNQISIEDDTNIALCEDTAARYEAYGWHVQRVEGGENVVAIEEAIAAAKA

VTDRPSFIELRTIIGYPAPNAMNTGKAHGAALGEEEVAAVKKILGFDPDKTFQVRDKVIAHTRKL

VDRGREAHQKWQTDFDAWAQREPERKALLERLTAEKLPDGWDADLPHWEPGSDAIATRKAS

GAVLNAVAPKLPELWGGSADLAESNLTTINNADSFGPPSISTKEFTASWYGRVLHFGVREHAM

GAILSGIVLHGPTRAYGGTFLQFSDYMRPAVRLASLMDIDTIYVWTHDSIGLGEDGPTHQPIEHL

AALRAIPKLSVVRPADANETAYAWRTILARGNGSGPVGLVLTRQGLPVLEGTDADGVARGGYIL

GSDGEEAGQEPDVILIATGSEVQLAVEAQKLLADKDIVARVVSMPCVEWFESQPDDYRDSVLP

PSVSARVAVEAGVAQSWHKLVGDTGKIISIEHYGESADYKTLFREFGFTAEAVAAAAEEVVDN

SEQ ID NO: 19 the amino acid sequence of a TKT from *Mycobacterium smegmatis* obtained from UniProtKB: A0R0M3 (A0R0M3_MYCS2),
MNESNDRIDTTLVGRLARQLRADAIRASTAAGSGHPTSSMSAADLTAVLLARHLSYDWERPDH

PDNDHFILSKGHASPLLYAAFKAVGVITDTELMTGYRRFGSRLQGHPTPVLPWVDVASGSLGQ

GIAIGVGVALAGKFLDRSGFHVWTLCGDSEMAEGSVWEALDKAGYYGLSNFTVIVDVNRLGQR

GPTEFGWDLETYAKRVEAFGARAISVDGHRLEAIDQALTAARNTTQPTVILARTVKGRGFSEVE

DREGWHGKAFPPEMARRALAELGEVEGLTVAGPKPASRSGQSSAPGAGNPDGFSDRPRYAP

GEKVATRAAYGAAVAALGAVNRRVVALDGEVSNSTGAAEFTEHHPERYFEMFIAEQQLVASSV

GLHVRHYIPFASTFAAFLTRAHDFIRMAAVSQANICLIGSHAGVEIGADGPSQMALEDLAMMRS

VHGATVLYPSDATSTVALVDLMADADGVRYLRTTRGAYPVLYEPATVFTIGGSHTLRSSSADDV

TLIGAGVTVHQCLAAAESLHRDGIAARVIDVYSVKPIDRDTLLEAVRDTGARLVIAEDHHPEGGL

GSAVLEAISGAETPRLKLMHLAVRAMPGSGTPAELLADAAIDAASIDKAARHLLQADDGRSDDG

RSDDDETLTA

-continued

SEQ ID NO: 20 the amino acid sequence of a TKT from *Mycobacterium abscessus* obtained from UniProtKB: B1MC67 (B1MC67_MYCA9),

MTAISRELAEVPTDIPTLTRVDHPDDWTELDSRAVDTVRVLAADAVQKVGNGHPGTAMSLAPV

AYTLFQRQLRHDPSDTTWIGRDRFVLSCGHSSLTLYLQLYLGGFGLELSDIEALRTWGSLTPGH

PEYHHTKGVEITTGPLGQGLASAVGMAMASRYERGLFDPDAAPGTSPFDHFIYVIASDGDIEEG

VTSEASSLAGTQQLGNLIVIWDDNEISIEHDTKIALSEDTPARYEAYGWHVQTVVSGENVTGLEE

ALANARAVTDRPSFIALRTIIGYPAPTKMNTGGVHGSALGADEVAATKKILGFDPDKSFEVAPEV

IAHTRELVTRGKQAHAEWDKSFEAWAAREPERKALLDRLQARALPQGWDAGLPSWEPGSKA

VATRAASGDTLSALGAKLPELWGGSADLAGSNNTTIKGADSFGPTSIATSDWNAQPYGRTLHF

GIREHAMGSILSGIVLHGPTRAYGGTFLQFADYMRPAVRLAALMNIDPIYVWTHDSIGLGEDGP

THQPVEHLAALRAIPNLSVVRPGDANETAYAWATVLERQSSTGPVGLALTRQGVPILEGTSRE

GVAKGGYVLEAASDNPADAPDVILIGTGSELQLAVEAKKILAAKGIAASVVSLPCVEWFESQPQ

EYRDSVLPPSVRARVVVEAGIAQGWYKFVGDAGQIVSLEHFGASADDKTLFREFGFTPDAVAA

AAERSIAAAQ

DETAILED DESCRIPTION

Active Mycobacterial tuberculosis infection (TB) remains a global health threat with 10 million new cases and 1.7 million deaths annually (Lawn et al., *Lancet,* 378(9785): 57-72, 2011; Nahid et al., *Am. J. Respir. Crit.,* 184(8): 972-979, 2011). Pulmonary TB is contagious and can be lethal and latent TB infection (LTBI) can evolve into active TB (Lawn et al., *Lancet,* 378(9785): 57-72, 2011). In addition, there is a need to distinguish TB from non-TB pulmonary diseases to provide appropriate treatment to the patient exhibiting pulmonary disease symptoms. Current commercially available antibody-based TB tests show poor sensitivity and specificity, which further affects the ability to accurately diagnose a patient with TB.

Disclosed herein are peptides that can specifically bind to *M. tuberculosis* (M.tb) transketolase antibodies which can be used for various immunoassays to capture or detect antibodies directed to M.tb in biological specimens. The peptides include at least the sequence THQPI (SEQ ID NO: 1), generally not at either end of the peptide (that is, contained within the peptide sequence). The immunoassay can be an enzyme-linked immunosorbent assay to aid in determining whether or not a subject has an active M.tb infection.

Provided herein in one embodiment is a method of detecting antibodies that specifically bind a *Mycobacterium tuberculosis* (M.tb) peptide in a sample of a subject suspected of having an M.tb infection, the method including detecting in the sample the presence of an antibody that reacts with (specifically binds to) a peptide including (or having) the sequence of SEQ ID NO: 1, SEQ ID NO: 12 (TKT μ; DLSSEVATHQPIIACLP), SEQ ID NO: 3 (TKT1; GEDGPTHQPIEHLSA), or SEQ ID NO: 5 (TKT3; HDSIGLGEDGPTHQPIEHLS). By way of examples of the method, the detecting includes performing an enzyme-linked immunoassay (such as an enzyme-linked immunosorbent assay (ELISA)), a radioimmunoassay, an immunoprecipitation, a fluorescence immunoassay, a chemiluminescent assay, an immunoblot assay, a lateral flow assay, a flow cytometry assay, a multi-plex particle-based suspension array assay, a mass spectrometry assay, or a particulate-based assay. In examples, the sample is serum, and the serum is diluted more than 1:50, 1:250 to 1:16000, 1:400-1:1000, or 1:500, serum to dilution agent.

Also provided are methods for aiding in the diagnosis of active *Mycobacterium tuberculosis* (M.tb) infection in a subject including: contacting a sample from the subject with a peptide including the sequence of SEQ ID NO: 1, 12, 3, or 5 under conditions suitable for an anti-transketolase (TKT) antibody in the sample to form a complex with the peptide; detecting a level of formation of the complex using an enzyme-linked immunosorbent (ELISA) assay including a detecting antibody, wherein the detecting antibody is a horseradish peroxidase (HRP) conjugated anti-human IgG antibody, and a substrate to detect HRP, thereby determining the level of the anti-transketolase antibody in the sample; and comparing the level of antibody in the sample to a control level, wherein the difference in the level of antibody in the sample relative to the control level is indicative of an increased likelihood of the subject having active M.tb infection. By way of example, in some methods the control level is the level of antibodies in a sample from a healthy subject. In optional examples of the method, an increased level of anti-TKT antibody present in the sample relative to the control level is indicative of an increased likelihood of said subject having active M.tb infection.

Also provided are immunoassay kit embodiments, which kits are useful for selectively detecting anti-transketolase antibody in a biological sample. Such kits included, as capture reagent, a peptide including (or alternatively, consisting of) the sequence of SEQ ID NO: 1, 12, 3 or 5, wherein the peptide forms a complex with an anti-transketolase antibody in the biological sample; and as detection reagent, a detectable anti-human IgG antibody, wherein the detectable anti-human IgG antibody binds to anti-transketolase antibody in the complex. Optionally, kit embodiments may further include a solid support for the capture reagent.

Optionally, the capture reagent provided in a kit is immobilized on the solid support. For instance, the capture reagent can be coated on a microtiter plate.

Examples of kit embodiments further include a detection means for the detectable antibody. Optionally, the detection means in colorimetric.

In examples of kit embodiments, the detectable antibody is one or more of: amplified by a fluorometric reagent;

HRP-conjugated and the detection means is 3,3',5,5'-tetramethyl benzidine; a monoclonal antibody (such as a goat monoclonal antibody).

Optionally, kit embodiments further include anti-transketolase antibody as an antibody standard.

Aspects of the current disclosure are now described with additional details and options as follows: (I) Representative Definitions; (II) Systems for detecting M.tb infection; (III) Subjects for testing for M.tb infection; (IV) Biological samples for testing for M.tb infection; (V) Using a peptide to detect M.tb infection in biological samples; (VI) Interpretation of Test Results; (VII) Kits; (VIII) Exemplary Embodiments; (IX) Experimental Examples; and (X) Closing Paragraphs. These headings do not limit the interpretation of the disclosure and are provided for organizational purposes only.

(I) REPRESENTATIVE DEFINITIONS

"Up-regulation" or "up-regulated" means an increase in the presence of a protein and/or an increase in the expression of its gene. "Down-regulation" or "down-regulated" means a decrease in the presence of a protein and/or a decrease in the expression of its gene. "Its gene" in reference to a particular protein refers to a nucleic acid sequence (used interchangeably with polynucleotide or nucleotide sequence) that encodes the particular protein. This definition also includes various sequence polymorphisms, mutations, and/or sequence variants wherein such alterations do not substantially affect the identity or function of the particular protein. For example, in a sequence identity analysis, the test protein would share at least 80% sequence identity; at least 81% sequence identity; at least 82% sequence identity; at least 83% sequence identity; at least 84% sequence identity; at least 85% sequence identity; at least 86% sequence identity; at least 87% sequence identity; at least 88% sequence identity; at least 89% sequence identity; at least 90% sequence identity; at least 91% sequence identity; at least 92% sequence identity; at least 93% sequence identity; at least 94% sequence identity; at least 95% sequence identity; at least 96% sequence identity; at least 97% sequence identity; at least 98% sequence identity or at least 99% sequence identity with the particular protein.

"% sequence identity" refers to a relationship between two or more sequences, as determined by comparing the sequences. In the art, "identity" also means the degree of sequence relatedness between protein (or nucleic acid) sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure, it will be understood that where sequence analysis software is used for analysis, the results of the analysis are based on the "default values" of the program referenced. "Default values" mean any set of values or parameters which originally load with the software when first initialized.

The term "gene" can include not only coding sequences but also regulatory regions such as promoters, enhancers, and termination regions. The term further can include all introns and other DNA sequences spliced from the mRNA transcript, along with variants resulting from alternative splice sites. Gene sequences encoding the particular protein can be DNA or RNA that directs the expression of the particular protein. These nucleic acid sequences may be a DNA strand sequence that is transcribed into RNA or an RNA sequence that is translated into the particular protein. The nucleic acid sequences include both the full-length nucleic acid sequences as well as non-full-length sequences derived from the full-length protein. The sequences can also include degenerate codons of the native sequence. Portions of complete gene sequences are referenced throughout the disclosure as is understood by one of ordinary skill in the art.

"Protein" detection includes detection of full-length proteins, mature proteins, pre-proteins, polypeptides, isoforms, mutations, post-translationally modified proteins and variants thereof, and can be detected in any suitable manner.

A "population" is any grouping of subjects or samples of like specified characteristics. The grouping could be according to, for example, clinical parameters, clinical assessments, therapeutic regimens, disease status, severity of condition, etc.

The term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Alternatively, relative quantification can be accomplished by comparison of detected levels or amounts between two or more different markers to provide a relative quantification of each of the two or more markers, e.g., relative to each other. The actual measurement of values of the markers can be determined at the protein using any method known in the art.

A probe is a molecule that binds a target, either directly or indirectly. The target can be a marker, a fragment of the marker, or any molecule that is to be detected. In embodiments, the probe includes a nucleic acid or a protein. As an example, a protein probe can be an antibody. An antibody can be a whole antibody or a fragment of an antibody. A probe can be labeled with a detectable label. Examples of detectable labels include fluorescers, chemiluminescers, dyes, enzymes, enzyme substrates, enzyme cofactors, enzyme inhibitors, enzyme subunits, metal ions, and radioactive isotopes. A probe can be included in reagents.

A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

(II) SYSTEMS FOR DETECTING M.TB INFECTION

Described herein are systems of detecting M.tb infection in a subject for diagnosing a subject suspected of having M.tb infection. The systems can aid in differentiating a subject having an active M.tb infection from a latent M.tb infection or a non-M.tb pulmonary disease. In particular, the peptides described herein can be used in an enzyme-linked immunoassay to detect the presence of M.tb antibodies with high specificity and sensitivity in samples isolated from a subject.

The systems include a peptide comprising THQPI (SEQ ID NO: 1), DLSSEVATHQPIIACLP (SEQ ID NO: 12, TKTμ), GEDGPTHQPIEHLSA (SEQ ID NO: 3), or HDSIGLGEDGPTHQPIEHLS (SEQ ID NO: 5). The peptides specifically bind to antibodies for M.tb and can be used in various applications to capture or detect antibodies for M.tb present in a biological sample. Applications can include enzyme-linked immunoassay, a radioimmunoassay, an immunoprecipitation, a fluorescence immunoassay, a chemiluminescent assay, an immunoblot assay, a lateral flow assay, a flow cytometry assay, a multi-plex particle-based suspension array assay, a mass spectrometry assay, or a particulate-based assay. For example, the peptides described herein can be used as an antigen to capture M.tb antibodies present in a sample which then the peptide-antibody complex can be detected by a detecting antibody in an enzyme-linked immunosorbent assay.

(III) SUBJECTS FOR TESTING FOR M.TB INFECTION

Subjects include humans, veterinary animals (dogs, cats, reptiles, birds, hamsters, etc.) livestock (horses, cattle, goats, pigs, chickens, etc.), research animals (monkeys, rats, mice, fish, etc.) and other animals, such as zoo animals (e.g., bears, giraffe, elephant, lemurs).

Subjects with suspected of having tuberculosis disease, such as having coughing lasting longer than three weeks, hemoptysis, or chest pain may benefit from being tested to confirm M.tb infection. Subjects showing general tuberculosis disease symptoms, which include unexplained weight loss, loss of appetite, night sweats, fever, fatigue, and chills, may also benefit from being tested to M.tb infection. In addition, individuals with symptoms of M.tb infection, subjects who are at risk for M.tb infection, such as those who have been exposed to a M.tb patient or are immunocompromised, or individuals who have contact with high-risk individuals can benefit from being tested for M.tb. Testing to accurately diagnose an M tb infection will assist in ensuring that the appropriate therapy is determined and administered to the subject with M.tb infection.

Latent TB infection does not show symptoms and does not spread the infection to others. However, untreated latent TB infection can develop to active tuberculosis disease. Individuals with latent TB infection may benefit from being tested for active TB infection to assist in monitoring the disease status.

(IV) BIOLOGICAL SAMPLES FOR TESTING FOR M.TB INFECTION

The sample can be any appropriate biological sample obtained from the subject, such as a blood sample, a serum sample, a saliva sample, a sputum sample, a urine sample, bronchoalveolar lavage sample, etc. The sample also can be obtained from a biopsy of an affected tissue or organ, such as a lung biopsy, or lymph gland biopsy. The sample can include cells of affected tissue or organ.

Blood may be collected from a patient and tested by using the methods described herein. The blood sample may be processed to collect the serum or plasma fractions for testing.

To test a serum sample, the serum may be isolated from blood by using a serum separator tube to allow blood samples to clot at room temperature for 30 minutes. The sample in the tube may be centrifuged at 1000×g for 15 minutes before removing the separated serum from the sample. The serum may be assayed immediately or stored at temperatures at −20° C. or lower prior to analysis.

To test a plasma sample, the plasma may be isolated from blood by first adding an anticoagulant such as EDTA, heparin, or citrate, to the blood sample. The mixture can then be centrifuged for 15 minutes at 1000×g to separate plasma from the blood sample. The separated plasma may be assayed immediately or stored at temperatures at −20° C. or lower prior to analysis.

To test a saliva sample, the saliva may be collected in a tube by the subject spitting into the tube. The tube with the saliva sample may be centrifuged for 5 minutes at 10,000×g to separate an aqueous layer from cellular debris. The aqueous layer can be assayed immediately or stored at temperatures at −20° C. or lower prior to analysis.

To test a sputum sample, sputum is collected and may be liquefied, such as by incubating with dithiothreitol, filtered through gauze, and washed with PBS by centrifugation before analysis. The non-cellular fraction may be assayed immediately or stored at temperatures at −20° C. or lower prior to analysis.

Urine samples may be assayed. Urine can be collected in a sterile container then may be centrifuged to pellet cells in the urine sample. The aqueous layer or the pelleted cells resuspended in a chosen medium may be assayed immediately or stored at temperatures at −20° C. or lower prior to analysis.

Bronchoalveolar lavage samples may be tested. To test a bronchoalveolar lavage sample, the sample is collected by following American Thoracic Society guidelines. A saline solution can be infused into a subsegment of a lung followed by suction and collection of the specimen. The specimen may be centrifuged to separate the supernatant from cells in the sample. The supernatant can be assayed immediately or stored at temperatures at −20° C. or lower prior to analysis. The pelleted cells may also be assayed by lysing and centrifuging before analysis.

Tissues from a biopsy may be homogenized or lysed before analysis. To prepare homogenized tissue samples, the tissue can be rinsed with phosphate buffered saline (PBS) or another buffer of choice before homogenization using a tissue homogenizer in the buffer. The homogenate may be processed through freeze-thaw cycles to break cell membranes then centrifuged to separate a supernatant portion from cell debris for testing. The supernatant may be assayed immediately or stored at temperatures at −20° C. or lower prior to analysis. To prepare tissue lysate samples, the tissue can be first rinsed with PBS or another buffer of choice, homogenized, then agitated with a lysis buffer such as Radio-Immunoprecipitation Assay buffer. The mixture can be centrifuged to separate a supernatant portion from cell debris for testing. The supernatant may be assayed immediately or stored at temperatures at −20° C. or lower prior to analysis.

(V) USING A PEPTIDE TO DETECT M.TB INFECTION IN BIOLOGICAL SAMPLES

The peptides described herein are synthetic peptides determined to be antigenic based on the sequence of M.tb transketolase. Described herein are peptides that specifically bind to antibodies for M.tb and can be used in various applications to capture or detect antibodies for M.tb present in a biological sample with high specificity and sensitivity. Applications include various immunoassays, including enzyme-linked immunosorbent assays. Enzyme-linked immunosorbent assays are relatively simple procedures without complicated pre-processing of biological samples.

The peptides described herein can be used as an antigen to capture M.tb antibodies present in a biological sample in an enzyme-linked immunosorbent assay. The peptides are coated or anchored in wells of microtiter plates onto which biological samples are incubated. Any antigen-antibody complex that forms can be detected by a detecting antibody, which is a label-conjugated IgG antibody, the label of which can then be used to measure and calculate the level of the M.tb antibody present in the tested sample. A peptide standard curve is generated with the testing of the biological samples to be used to determine the M.tb antibody levels in the biological samples and to aid in the identification of samples positive for M.tb antibodies and determination of M.tb infection in the subject.

Those skilled in the art will be familiar with numerous specific immunoassay formats and variations thereof which can be useful for carrying out the methods disclosed herein. See, e.g., E. Maggio, Enzyme-Immunoassay (1980), CRC Press, Inc., Boca Raton, Fla; and U.S. Pat. Nos. 4,727,022; 4,659,678; 4,376,110; 4,275,149; 4,233,402; and 4,230,797.

Examples of suitable immunoassays include immunoblotting, immunoprecipitation, immunofluorescence, chemiluminescence, electro-chemiluminescence (ECL), and/or enzyme-linked immunoassays (ELISA).

The disclosure of protein and/or nucleic acid sequence markers herein is not limited to the particularly disclosed protein and gene sequences but instead also encompasses sequences including 80% sequence identity; 81% sequence identity; 82% sequence identity; 83% sequence identity; 84% sequence identity; 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity or 99% sequence identity.

Proteins can be linked to chips, such as microarray chips. See, for example, U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138. Microarray refers to a solid carrier or support that has a plurality of molecules bound to its surface at defined locations. The solid carrier or support can be made of any material. As an example, the material can be hard, such as metal, glass, plastic, silicon, ceramics, and textured and porous materials; or soft materials, such as gels, rubbers, polymers, and other non-rigid materials. The material can also be nylon membranes, epoxy-glass and borofluorate-glass. The solid carrier or support can be flat but need not be and can include any type of shape such as spherical shapes (e.g., beads or microspheres). The solid carrier or support can have a flat surface as in slides and micro-titer plates having one or more wells.

Binding to proteins or nucleic acids on microarrays can be detected by scanning the microarray with a variety of laser or CCD-based scanners, and extracting features with software packages, for example, Imagene (Biodiscovery, Hawthorne, CA), Feature Extraction Software (Agilent), Scanalyze (Eisen, M. 1999. SCANALYZE User Manual; Stanford Univ., Stanford, Calif. Ver 2.32.), or GenePix (Axon Instruments).

Antibodies can be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

(VI) INTERPRETATION OF TEST RESULTS

Up- or down-regulation of the markers, as indicated elsewhere herein for particular markers, can be assessed by comparing a value to a relevant reference level. For example, the quantity of one or more markers can be indicated as a value. The value can be one or more numerical values resulting from the assaying of a sample, and can be derived, e.g., by measuring level(s) of the marker(s) in the sample by an assay performed in a laboratory, or from a dataset obtained from a provider such as a laboratory, or from a dataset stored on a server. The markers disclosed herein can be a protein marker or a nucleic acid marker (gene encoding the protein marker).

In the broadest sense, the value may be qualitative or quantitative. As such, where detection is qualitative, the systems and methods provide a reading or evaluation, e.g., assessment, of whether or not the marker is present in the sample being assayed. In yet other embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. In some embodiments, a marker is detected by contacting a sample with reagents (e.g., antibodies or nucleic acid primers), generating complexes of reagent and marker(s), and detecting the complexes.

As stated previously, obtained marker values can be compared to a reference level. Reference levels can be obtained from one or more relevant datasets.

A reference level from a dataset can be derived from previous measures derived from a population.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05.

In one embodiment, values obtained about marker(s) and/or other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained value with a reference level, a linear algorithm, a quadratic algorithm, a decision tree algorithm, or a voting algorithm. The analytic process may set a threshold for determining the probability that a sample belongs to a given class. The probability preferably is at least at least 60%, at least 70%, at least 80%, at least 90%, at least 95% or higher.

In embodiments, the relevant reference level for a particular marker is obtained based on the particular marker in control subjects. Control subjects are those that are healthy and do not have sarcoidosis or tuberculosis. As an example, the relevant reference level can be the quantity of the particular marker in the control subjects.

In additional embodiments when more than one marker is assayed, values of the detected markers can be calculated into a score. Each value can be weighted evenly within an algorithm generating a score, or the values for particular markers can be weighted more heavily in reaching the score. For example, markers with higher sensitivity and/or specificity scores could be weighted more heavily than markers with lower sensitivity and/or specificity scores.

Particular embodiments disclosed herein include obtaining a sample from a subject suspected of having tuberculosis (TB); assaying the sample for up- or down-regulation of a marker disclosed herein (e.g., a marker corresponding to transketolase, TKT); determining one or more marker values based on the assaying; comparing the one or more marker values to a reference level; diagnosing tuberculosis in the subject according to the level or presence (or absence) of a marker, as described elsewhere herein (e.g., an increase in the level of an antibody that specifically binds to a peptide comprising (or consisting of) the sequence of SEQ ID NO: 1, 12, 3 or 5.

A diagnosis according to the systems and methods disclosed herein can direct a treatment regimen. For example, a tuberculosis diagnosis can direct treatment with a tuberculosis treatment (e.g., isoniazid (INH); rifampin (RIF); ethambutol (EMB); pyrazinamide (PZA)). A healthy diagnosis can direct further medical analysis if the subject's symptoms suggest further analysis is warranted. Administered treatments will be delivered in therapeutically effective amounts leading to an improvement or resolution of the treated condition, as assessed by a practicing physician, veterinarian, or researcher.

In embodiments, diagnosis of tuberculosis as disclosed herein may be combined with previously disclosed methods of using a computing device to provide for a quicker, more reliable, and less labor-intensive diagnosis. See, for instance, FIG. 10 and the related text of U.S. Pat. No. 10,781,489 ("SYSTEMS AND METHODS TO DIAGNOSE SARCOIDOSIS AND IDENTIFY MARKERS OF THE CONDITION"; issued Sep. 22, 2020).

(VII) KITS

The systems and methods disclosed herein include kits. Disclosed kits include materials and reagents necessary to assay a sample obtained from a subject for one or more markers disclosed herein. The materials and reagents can include those necessary to assay the markers disclosed herein according to any method described herein and/or known to one of ordinary skill in the art.

Particular embodiments include materials and reagents necessary to assay for up- or down-regulation of a marker in a sample. In particular embodiments, the kits include a peptide comprising (or having) the sequence of SEQ ID NO: 1, SEQ ID NO: 12 (TKTμ; DLSSEVATHQPIIACLP), or SEQ ID NO: 3 (TKT1; GEDGPTHQPIEHLSA), or SEQ ID NO: 5 (TKT3; HDSIGLGEDGPTHQPIEHLS). Collectively, any molecule (e.g., peptide, protein, antibody, aptamer, epitope, mimotope, oligonucleotide) that forms a complex with a marker is referred to as a marker binding agent herein.

Embodiments of kits can contain in separate containers marker binding agents either bound to a matrix or packaged separately with reagents for binding to a matrix. In particular embodiments, the matrix is, for example, a porous strip. In some embodiments, measurement or detection regions of the porous strip can include a plurality of sites containing marker binding agents. In some embodiments, the porous strip can also contain sites for negative and/or positive controls. Alternatively, control sites can be located on a separate strip from the porous strip. Optionally, the different detection sites can contain different amounts of marker binding agents, e.g., a higher amount in the first detection site and lesser amounts in subsequent sites. Upon the addition of test sample, the number of sites displaying a detectable signal provides a quantitative indication of the amount of marker present in the sample. The detection sites can be configured in any suitably detectable shape and can be, e.g., in the shape of a bar or dot spanning the width (or a portion thereof) of a porous strip.

In some embodiments the matrix can be a solid substrate, such as a "chip." See, e.g., U.S. Pat. No. 5,744,305. In some embodiments the matrix can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Additional embodiments can include control formulations (positive and/or negative), and/or one or more detectable labels, such as fluorescein, green fluorescent protein, rhodamine, cyanine dyes, Alexa dyes, luciferase, and radiolabels, among others. Instructions for carrying out the assay, including, optionally, instructions for generating a score, can be included in the kit; e.g., written, tape, VCR, or CD-ROM.

In particular embodiments, the kits include materials and reagents necessary to conduct an immunoassay (e.g., ELISA). In particular embodiments, materials and reagents expressly exclude equipment (e.g., plate readers). In particular embodiments, kits can exclude materials and reagents commonly found in laboratory settings (pipettes; test tubes; distilled H2O).

The Exemplary Embodiments and Example(s) below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(VIII) EXEMPLARY EMBODIMENTS

1. A method of detecting antibodies that specifically bind a *Mycobacterium tuberculosis* (M.tb) peptide in a sample of a subject suspected of having an M.tb infection, including detecting in the sample the presence of an antibody that reacts with (specifically binds to) a peptide including (or having) the sequence of SEQ ID NO: 1, SEQ ID NO: 12 (TKTμ; DLSSEVATHQPIIACLP), SEQ ID NO: 3 (TKT1; GEDGPTHQPIEHLSA), or SEQ ID NO: 5 (TKT3; HDSIGLGEDGPTHQPIEHLS).
2. The method of embodiment 1, wherein the detecting includes performing an enzyme-linked immunoassay, a radioimmunoassay, an immunoprecipitation, a fluorescence immunoassay, a chemiluminescent assay, an immunoblot assay, a lateral flow assay, a flow cytometry assay, a multi-plex particle-based suspension array assay, a mass spectrometry assay, or a particulate-based assay.
3. The method of embodiment 2, wherein the enzyme-linked immunoassay is an enzyme-linked immunosorbent assay (ELISA).
4. The method of embodiment 1, wherein the sample is serum, and the serum is diluted more than 1:50, 1:250 to 1:16000, 1:400-1:1000, or 1:500, serum to dilution agent.
5. A method for aiding in the diagnosis of active *Mycobacterium tuberculosis* (M.tb) infection in a subject including: contacting a sample from the subject with a peptide including the sequence of SEQ ID NO: 1, 12, 3, or 5 under conditions suitable for an anti-transketolase (TKT) antibody in the sample to form a complex with the peptide; detecting a level of formation of the complex using an enzyme-linked immunosorbent (ELISA) assay including a detecting antibody, wherein the detecting antibody is a horseradish peroxidase (HRP) conjugated anti-human IgG antibody, and a substrate to detect HRP, thereby determining the level of the anti-transketolase antibody in the sample; and comparing the level of antibody in the sample to a control level, wherein the difference in the level of antibody in the sample relative to the control level is indicative of an increased likelihood of the subject having active M.tb infection.
6. The method of embodiment 5, wherein the control level is the level of antibodies in a sample from a healthy subject.
7. The method of embodiment 6, wherein an increased level of anti-TKT antibody present in the sample relative to the control level is indicative of an increased likelihood of said subject having active M.tb infection.
8. An immunoassay kit for selectively detecting anti-transketolase antibody in a biological sample, the kit including: as capture reagent, a peptide including (or alternatively, consisting of) the sequence of SEQ ID NO: 1, 12, 3 or 5, wherein the peptide forms a complex with an anti-transketolase antibody in the biological sample; and as detection reagent, a detectable anti-human IgG antibody, wherein the detectable anti-human IgG antibody binds to anti-transketolase antibody in the complex.
9. The kit of embodiment 8, further including a solid support for the capture reagent.
10. The kit of embodiment 9, wherein the capture reagent is immobilized on the solid support.
11. The kit of embodiment 10, wherein the capture reagent is coated on a microtiter plate.
12. The kit of embodiment 8, further including a detection means for the detectable antibody.
13. The kit of embodiment 12, wherein the detection means in colorimetric.
14. The kit of embodiment 8, wherein the detectable antibody is amplified by a fluorometric reagent.
15. The kit of embodiment 8, wherein the detectable antibody is HRP-conjugated and the detection means is 3,3',5,5'-tetramethyl benzidine.
16. The kit of embodiment 8, wherein the detectable antibody is a monoclonal antibody.
17. The kit of embodiment 16, wherein the detectable antibody is a goat monoclonal antibody.
18. The kit of embodiment 8, further including anti-transketolase antibody as an antibody standard.

(IX) EXPERIMENTAL EXAMPLES

Example 1: Discovery of Novel Transketolase Epitopes and the Development of IgG-Based Tuberculosis Serodiagnosis Despite advances in rapid molecular techniques for tuberculosis (TB) diagnostics, there is an unmet need for a point-of-care non-sputum-based test. Previously, through a T7 phage antigen display platform and immunoscreening, it was identified that serum IgGs of active TB patients differentially bind to several antigen-clones and this immunoreactivity discriminates TB from other respiratory diseases. One of these high-performance clones has some homology to *Mycobacterium tuberculosis*' transketolase (M.tb TKT). In this study, a direct ELISA detecting IgG against TKT antigen-clone (TKTμ) was developed. Through sequence alignment and in silico analysis, 2 more peptides with potential antigenicity corresponding to M.tb-specific transketolase (M.tb-TKT1 and M.tb-TKT3) epitopes were designed. After development and standardization of a direct peptide ELISA for three peptides, 292 subjects including TB (n=101), LTBI (n=49), healthy controls (n=66) and sarcoidosis (n=76) were tested. 60% of subjects were randomly assigned to a training set to create optimal models distinguishing positive TB samples, and the remaining 40% were used to validate the diagnostic power of IgG based assays developed in the training set. Antibodies against M.tb TKT3 yielded the highest sensitivity (0.845) followed by TKTμ (0.817), and M.tb TKT1 (0.732). The specificities obtained by TKTμ, M.tb TKT3, and M.tb TKT1 on the test sets are 1, 0.95, and 0.875, respectively. The model using TKTμ obtains a perfect positive predictive value (PPV) of 1, followed by M.tb TKT3 (0.968) and M.tb TKT1 (0.912). These results show that IgG antibodies against transketolase can discriminate active TB against LTBI, sarcoidosis and controls.

There is an unmet need for a point-of-care non-sputum-based TB test. Through immunoscreening of a novel T7 phage library, classifiers that specifically bind to IgGs in active TB sera were identified. It was discovered that one of these clones is aligned with *Mycobacterium tuberculosis* transketolase (TKT). TKT is an essential enzyme for *Mycobacterium tuberculosis* growth. Three TKT epitopes (TKTμ, TKT1 and TKT3) were designed to detect TKT-specific IgGs. After the development and standardization of three different ELISA utilizing TKT peptides, 292 subjects including active TB, LTBI, healthy controls, and sarcoidosis were tested. Rigorous statistical analyses using training and validation sets showed that ELISA based detection of specific IgGs against TKT3 and TKTμ have the greatest sensitivity, specificity, and accuracy to distinguish active TB subjects from others, even LTBI. This work provides a novel scientific platform to further develop a point-of-care test aiding a faster TB diagnosis.

At least some of the information included in this Example was published as Talreja et al., *Microbiol Spectr*, e0337722, 18 Jan. 2023, doi:10.1128/spectrum.03377-22.

INTRODUCTION

Active Mycobacterial tuberculosis infection (TB) remains a global health threat with 10 million new cases and 1.7 million deaths annually (Lawn et al., Lancet, 378(9785): 57-72, 2011; Nahid et al., Am. J. Respir. Crit., 184(8): 972-9, 2011). One third of the world's population is infected with TB but not all are considered to have latent TB infection (LTBI) (Nahid et al., Am. J. Respir. Crit., 184(8): 972-9, 2011). Pulmonary TB is contagious and can be lethal and LTBI can evolve into active TB (Lawn et al., Lancet, 378(9785): 57-72, 2011). Efforts during the past decade to consistently diagnose and treat pulmonary cases have slowed the TB incidence rate, but have not yielded substantial progress (Wallis et al., Lancet, 375(9729): 1920-37, 2010). The existing TB diagnostics pipeline still does not have a simple, rapid, inexpensive point-of-care (POC) test (Wallis et al., Lancet, 375(9729):1920-37, 2010). The World Health Organization (WHO) has defined high-priority target product profiles for tuberculosis diagnostics (Denkinger et al., J Infect Dis, 220:S91-S8, 2019; Hong et al., Sci Transl Med, 14:eabj4124, 2022). These priorities include a sputum-based POC smear replacement test, a non-sputum biomarker-based POC TB test, a POC triage test, and a rapid drug-susceptibility test (DST) (Hong et al., Sci Transl Med, 14:eabj4124, 2022.). The discovery of specific biomarkers in form of antibodies distinguishing the immunity in active TB and LTBI could be the key to understanding the humoral responses against mycobacterial pathogens. Current commercially available antibody-based TB tests show poor sensitivity and specificity and none can distinguish active TB from LTBI (Steingart et al., PLOS Med, 4(6): e202, 2007). Due to the lack of precision, WHO does not endorse the routine application of the current commercial serological tests for TB diagnosis (World Health Organization, WHO operational handbook on tuberculosis: module 3: diagnosis: tests for tuberculosis infection. 2022; Melkie et al., Eur Respir Rev, 31, 2022). Serological diagnosis of tuberculosis has been challenging, partly due to large M.tb proteome and even larger antigenic epitopes (Denkinger et al., J Infect Dis, 220:S91-S8, 2019), and heterogeneity across humans in immunoglobulin G (IgG) response to tuberculosis (Achkar et al., Cell Host Microbe, 13:250-62, 2013). Most tuberculosis serological tests use purified M.tb proteins, a single or small number of antigens, predominantly derived from membrane proteins of M.tb (Steingart et al., PLOS Med, 4(6): e202, 2007). Challenges for the development of effective serological tests include the need to differentiate active pulmonary TB from other pulmonary diseases, including pneumonia or other granulomatous disease such as pulmonary sarcoidosis.

Sarcoidosis is a non-infectious systemic granulomatous disease with remarkable similarity to TB in clinical, immune responses, and in gene expression signatures (Maertzdorf et al., Genes Immun, 12:15-22, 2011; Maertzdorf et al., Proc Natl Acad Sci USA, 109:7853-8, 2012; Oswald-Richter et al., J Clin Immunol, 30:157-66, 2010; Blankley et al., PloS one, 11:e0162220, 2016). Previously, a T7 phage antigen display platform was developed and after immunoscreening of large sets of serum samples, 10 clones that differentially bind to serum IgG of active TB patients differentiating TB from other respiratory diseases were identified (Talwar et al., Viruses, 10(7), 2018; Talwar et al., EBioMedicine, 2(4): 341-50, 2015). One of these high-performance clones had homology to *Mycobacterium tuberculosis*' (M.tb) transketolase (Talwar et al., *Viruses,* 10(7), 2018; McEwan et al., Nat Immunol, 14(4): 327-36, 2013). Transketolase (TKT) is an essential enzyme for the intracellular growth of M.tb (Fullam et al., Open Biol, 2(1): 110026, 2012) and is the key enzyme in non-oxidative pentose phosphate pathway (Fullam et al., Open Biol, 2(1): 110026, 2012; Tan et al., J Infect Dis, 220(12): 1967-76, 2019; Schenk et al., J Mol Evol, 44(5): 552-72, 1997). It catalyzes the reversible transfer of a two-carbon ketol group from sedoheptulose-7-phosphate to glyceraldehyde-3-phosphate, producing xylulose-5-phosphate and ribose-5-phosphate. TKT has a highly evolutionary conserved structure and function, but there are intraspecies and interspecies amino acid (AA) variations among microorganisms and mammals (Fullam et al., *Open Biol,* 2(1): 110026, 2012; Schenk et al., *J Mol Evol,* 44(5): 552-72, 1997).

Because it was previously have shown that IgG of TB sera differentially bind to antigen-clone containing TKT μ (Talwar et al., *Viruses,* 10(7), 2018; Talwar et al., *EBioMedicine,* 2(4): 341-50, 2015) and M.tb transketolase is required for bacterial growth (Kamada et al., Appl Microbiol Biotechnol, 56(5): 710-717, 2001), it was hypothesized that abundance of IgG in sera against specific TKT may differentiate between active TB, LTBI and other non-TB granulomatous lung diseases. By aligning TKTμ with TKT sequences from *H. sapiens*, M.tb and *Staphylococcus aureus*, it was found that the core sequence of TKTμ shares homology with M.tb TKT. Because there are some AA differences between TKTμ and M.tb TKT, two additional M.tb TKT-peptide homologs (TKT1 and TKT3) were designed to develop a novel direct ELISA and to quantify the levels of IgG against these three TKT peptides (TKTμ, M.tb TKT1 and M.tb TKT3) for the TB serodiagnosis.

Materials and Methods

Chemicals and Antibodies

ELISA plates were purchased from R&D systems (Minneapolis, MN), Goat anti-human IgG HRP-linked antibody was purchased from Abcam (Cambridge, MA), blocking buffer was purchased from Bio-Rad (Bio-Rad, Hercules, CA).

Patient Selection

This study was approved by the institutional review board at Wayne State University, and the Detroit Medical Center. All methods were performed in accordance with the human investigation guidelines and regulations by the IRB (protocol No=055208MP4E) at Wayne State University. All experiments were performed in accordance with guidelines and regulations of investigation of human subjects. Sera were collected from 4 groups: (1) healthy volunteers (n=66); (2) sarcoidosis subjects (n=76); (3) pulmonary TB patients (n=101), 4) latent TB (n=49). All study subjects signed a written informed consent. Sera from patients with active and latent tuberculosis were obtained from the Foundation for Innovative New Diagnostics (FIND, Geneva, Switzerland). All TB patients had smear positive sputum. LTBI subjects had negative smear and culture but positive interferon gamma release assays (IRGs).

Alignment of TKT sequence from *Homo sapiens, Mycobacterium tuberculosis* (M.tb) and *Staphylococcus aureus* (*S. aureus*). The amino acid sequences of TKT were obtained from UniProtKB: P9WG25 (TKT_MYCTU; SEQ ID NO: 8), AOAOB4J1R6 (TKT_HUMAN), Q6G9L6 (TKT_STAAS). The sequence alignment and homology of TKT was done by using T-Coffee Multiple Sequence Alignment program (Di Tommaso et al., NAR 39 (Web): W13-7, 2011; Notredame et al., *J Mol Biol.* 302(1):205-217, 2000). FASTA files of the TKT amino acid (AA) sequences of three species were submitted to T-coffee alignment program and illustrated in ClustalW format.

TKT Peptide ELISA

TKT peptide was chemically synthesized by GenScript (Piscataway, NJ). MicroPlate (R&D system) was coated with TKT peptide at the concentration of 500 ng/ml (100 μl/well) for overnight at room temperature (RT). Next day plates were washed 3× with washing buffer (PBS with 0.05% Tween-20). Plates were blocked at RT for 1 h with blocking buffer (Bio-Rad). After blocking, the plates were washed 3× with washing buffer, and individual serum samples (1:500 in blocking buffer) in duplicates were added onto wells and incubated at RT for 2 h. After 2 h, the plates were washed 3× and then incubated with goat anti-human IgG HRP linked secondary antibody (Abcam, Waltham, MA) at RT for 90 min. Plate was washed 4×, and 100 μl/well TMB substrate mixture (R&D system) was added for 20 min at RT and the reaction was stopped by adding 50 μl of 2N $H_2SO_4$ to each well. The optical density (OD) was measured at 450 nm using microplate reader (Biotek).

Generation of rabbit polyclonal antibody against TKTμ peptide. The rabbit polyclonal anti-TKTμ antibody was custom generated by GenScript (Piscataway, NJ). Briefly, TKTμ peptide was conjugated to the carrier protein KLH, 0.2 mg TKTμ peptide-KLH conjugate with Freud's complete adjuvant was administered subcutaneously per rabbit (New Zealand strain). After three booster doses of conjugated TKTμ peptide (0.2 mg/rabbit) on days 14, 28 and 42, the serum from the immunized rabbits was collected on day 49 and pooled and the polyclonal anti-TKTμ IgGs were purified using antigen affinity purification method.

Statistical Analyses

Sample size calculation and power analysis. Power and sample size was calculated using G power (Faul et al., Behav. Res. Methods, 39(2): 175-91, 2007). The estimated effect size of 0.5-0.6 with a 90% power and a false discovery rate (FDR) of 1-5%, the required sample size for TB was n=48 and non-infected individuals (healthy controls) n=50. To reach higher power to near 100% and be able to validate the results on an independent set, sample size was increased and included disease controls sarcoidosis subjects (n=76), and LTBI (n=49).

The analyses of ELISA data were performed in programming language R. A two-tailed t-test was applied to determine whether the measurements of IgG specific TKT antibodies in TB sera were significantly different as compared to other groups. Subsequently, the significant scores (p values) were corrected for multiple comparisons using the FDR (Benjamini et al., J R Stat Soc Series B Stat Methodol, 57(1): 289-300, 1995). To build a model for each IgG against TKT-epitopes to distinguish TB samples from non-TB samples, the data was randomly split into training and test sets with the ratio of 60/40. The model is defined as the optimal cut point on the receiver operating characteristic (ROC) curve obtained from the training set closest to the (1,0) point. A sample was classified as TB infection if its serum IgG ODs against specific TKT is greater than or equal to the OD threshold corresponding to this cut point. The ability to correctly identify TB and non-TB samples in the test set of each model was assessed based on the sensitivity, specificity, positive predictive value (PPV), negative predictive value (NPV), and accuracy when applying the model on the test set.

Results and Discussion

Results

Selection of a novel tuberculosis antigen and development of ELISA. Through the immunoscreening of the microarray platform with two different sets of sera from active TB and various positive and negative controls, 10 highly performing clones were identified (Talwar et al., Viruses, 10(7), 2018; Talwar et al., EBioMedicine, 2(4): 341-50, 2015). One of those clones had homology to M.tb TKT, and the sequence was labeled as TKTμ. Because of high sensitivity of TKTμ to recognize IgG of TB sera, this clone was chosen to develop a rapid ELISA test for serodiagnosis of TB (Talwar et al., Viruses, 10(7), 2018; Talwar et al., EBioMedicine, 2(4): 341-50, 2015). To develop the ELISA, the TKTμ peptide was chemically synthesized and purified. After extensive optimizations of peptide concentration, plate selection, serum dilution, incubation parameters, and detection antibody, the avidity of specific IgGs binding against TKTμ epitope in the sera of study subjects (n=292) via direct ELISA was determined. The avidity is the functional affinity as indicator of the relative strength of the interactions between IgG antibody binding sites to TKTμ epitope. In addition to healthy controls and TB patients, LTBI subjects and patients with sarcoidosis were included. Sarcoidosis subjects were included because many studies suggested a shared underlying pathophysiology and clinical features between sarcoidosis and TB (Maertzdorf et al., Genes Immun, 12:15-22, 2011; Maertzdorf et al., Proc Natl Acad Sci USA, 109:7853-8, 2012; Blankley et al., PloS one, 11:e0162220, 2016). For instance, M.tb antigens (ESAT6 and MKatG) induce T-cell-specific responses in the blood of sarcoidosis patients (Oswald-Richter et al., J Clin Immunol, 30:157-66, 2010; Richmond et al., J Clin Immunol, 33:446-55, 2013; Drake et al., Infect Immun, 75:527-30, 2007). All TB subjects had positive AFB smear and culture tests, while LTBI was defined based on negative smear and culture but a positive interferon gamma release assay (IRG) and skin tests. Characteristics of study groups are shown in Table 1.

TABLE 1

| | Study Subjects | | | |
|---|---|---|---|---|
| Characteristic | Controls | Sarcoidosis | TB Subjects | LTBI |
| Age (Mean ± SEM[a]) | 41 ± 11 | 46 ± 12 | 35 ± 11 | 33 ± 10 |
| Gender, N (%) | 66 | 76 | 101 | 49 |
| Male | 27 (40) | 27 (35) | 67 (66) | 30 (61) |
| Female | 39 (60) | 49 (64) | 34 (34) | 19 (39) |
| Race, N (%) | | | | |
| African American | 21 (31) | 72 (95) | 0 | 0 |
| African | 4 (6) | 0 | 11 (10) | 9 (18) |
| White | 29 (43) | 3 (4) | 0 | 0 |
| Asians | 13 (19) | 1 (1) | 89 (90) | 40 (82) |
| IRGsc | N/A | negative | N/A | positive |
| TB smear [d] | N/A | N/A | positive | negative |

[a]Standard error of mean,
[b] Not applicable,
[c] Interferon γ release assay,
[d] TB Smear (AFB positive sputum)

All measurements were duplicates and standardized in the lab. The results in FIG. 1A shows serum IgG optical density (OD) against the TKTμ epitope among study subjects. The OD values (mean±SD) of TKTμ-specific IgGs in sera of TB patients was 0.7±0.48, whereas the ODs in healthy controls, sarcoidosis and LTBI had average ODs of 0.18±0.09, 0.19±0.12, and 0.18±0.05, respectively. As shown, there were significant differences in the OD values between TB and healthy controls (adjusted p=4.26e-19), sarcoidosis (adjusted p=1.63e-18) and LTBI (adjusted p=4.26e-19).

Figure 1B:
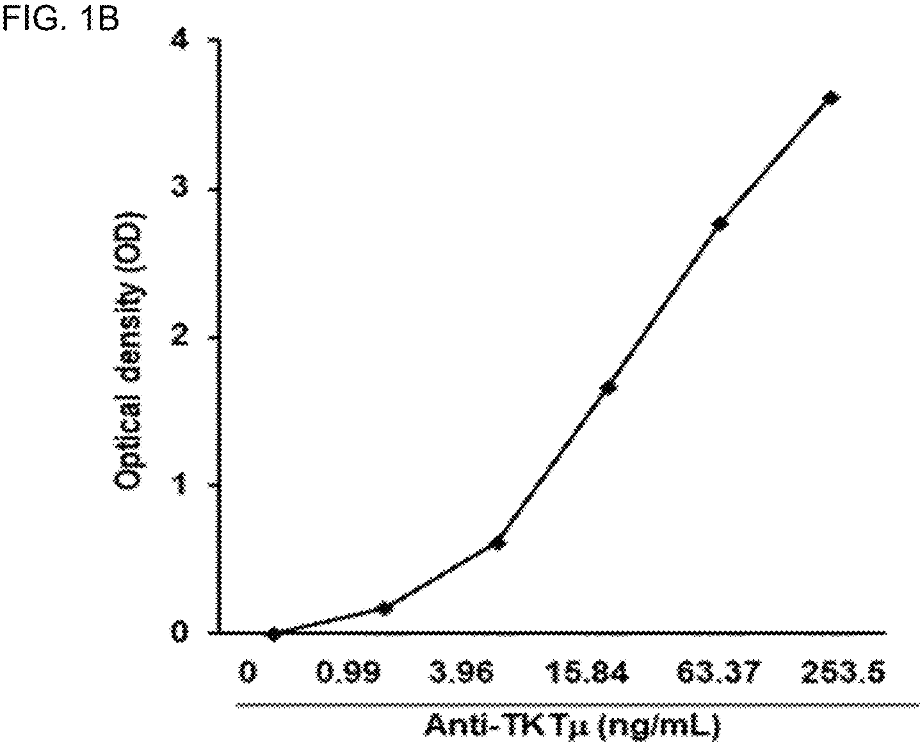
Figure 1C:
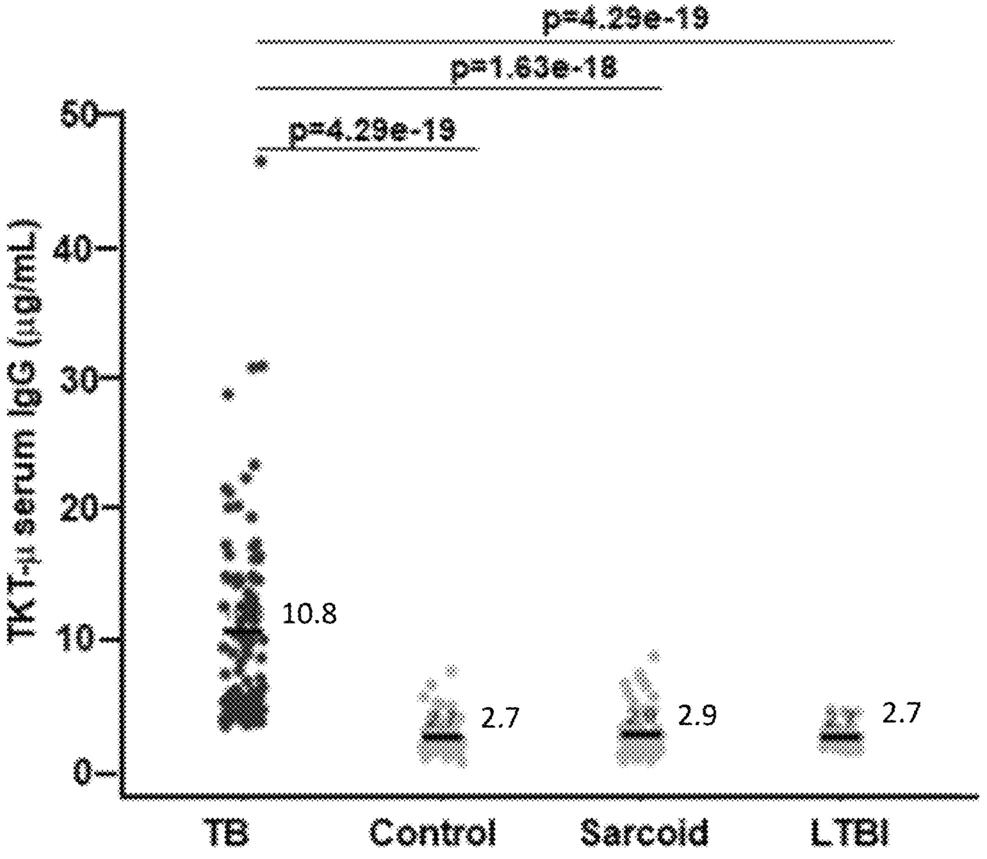

Rabbit immunizations and polyclonal antibody against TKTμ. Because significant differences in IgG immunoreactivity of TB sera against TKTμ epitope was observed, to quantify the concentration of TKTμ specific IgGs in serum and to develop TKTμ standard curve, rabbits were immunized with TKTμ peptide. After 3× immunizations of rabbits with TKTμ peptide, the immunization achieved high concentration of polyclonal IgG antibody against TKTμ that was purified. The polyclonal IgG antibody against TKTμ (anti-TKTμ IgG) was then utilized to obtain the anti-TKTμ antibody standard curve (FIG. 1B). The results of TKT peptide ELISA using different dilutions (1:1000-1:512,000) of rabbit anti-TKTμ IgG are shown in Table 2. The serum concentration of TKTμ specific IgGs concentration calculated based on standard curve in study groups. The mean of anti-TKTμ IgG antibodies in TB sera was 10.8 (ranging from 3 μg to 50 μg/mL). The mean of anti-TKTμ IgG antibodies in sera of controls, LTBI and sarcoidosis patients was 2.7 (ranging from 1.7-3.5 μg/mL). The FDR-adjusted p values between TB samples and healthy controls values were p=4.29e-19, TB samples and sarcoidosis p=1.6e-18, and LTBI was p=4.29 e-19. These data suggest a significant difference in the level of anti-TKTμ IgG antibody values in sera of TB subjects even in comparison with LTBIs' values (FIG. 1C).

Table 2 shows TKT-μ peptide ELISA using different dilutions of custom-made rabbit anti-TKT-μ IgG.

TABLE 2

| | OD (450 nm) | |
|---|---|---|
| Antibody Dilution | Anti-TKT-μ | Control IgG |
| 1:1,000 | 2.609 | 0.170 |
| 1:2,000 | 2.579 | 0.118 |
| 1:4,000 | 2.527 | 0.083 |

TABLE 2-continued

| | OD (450 nm) | |
|---|---|---|
| Antibody Dilution | Anti-TKT-μ | Control IgG |
| 1:8,000 | 2.451 | 0.072 |
| 1:16,000 | 2.294 | 0.063 |
| 1:32,000 | 2.033 | 0.059 |
| 1:64,000 | 1.781 | 0.055 |
| 1:128,000 | 1.412 | 0.053 |
| 1:256,000 | 1.007 | 0.059 |
| 1:512,000 | 0.683 | 0.054 |
| Blank | 0.055 | 0.057 |

TKT-μ peptide ELISA using different dilutions of custom-made rabbit anti-TKTμ IgG. TKT-μ peptide ELISA was done via standardized TKT peptide ELISA. Two-fold serial dilutions of custom made anti-TKT-μ antibody (1:1000-1:512,000) in duplicates were used. Rabbit IgG (1:1000-1:512,000) was used as a control. The ELISA plate was read for OD value at 450 nm using plate reader.

Figure 3:
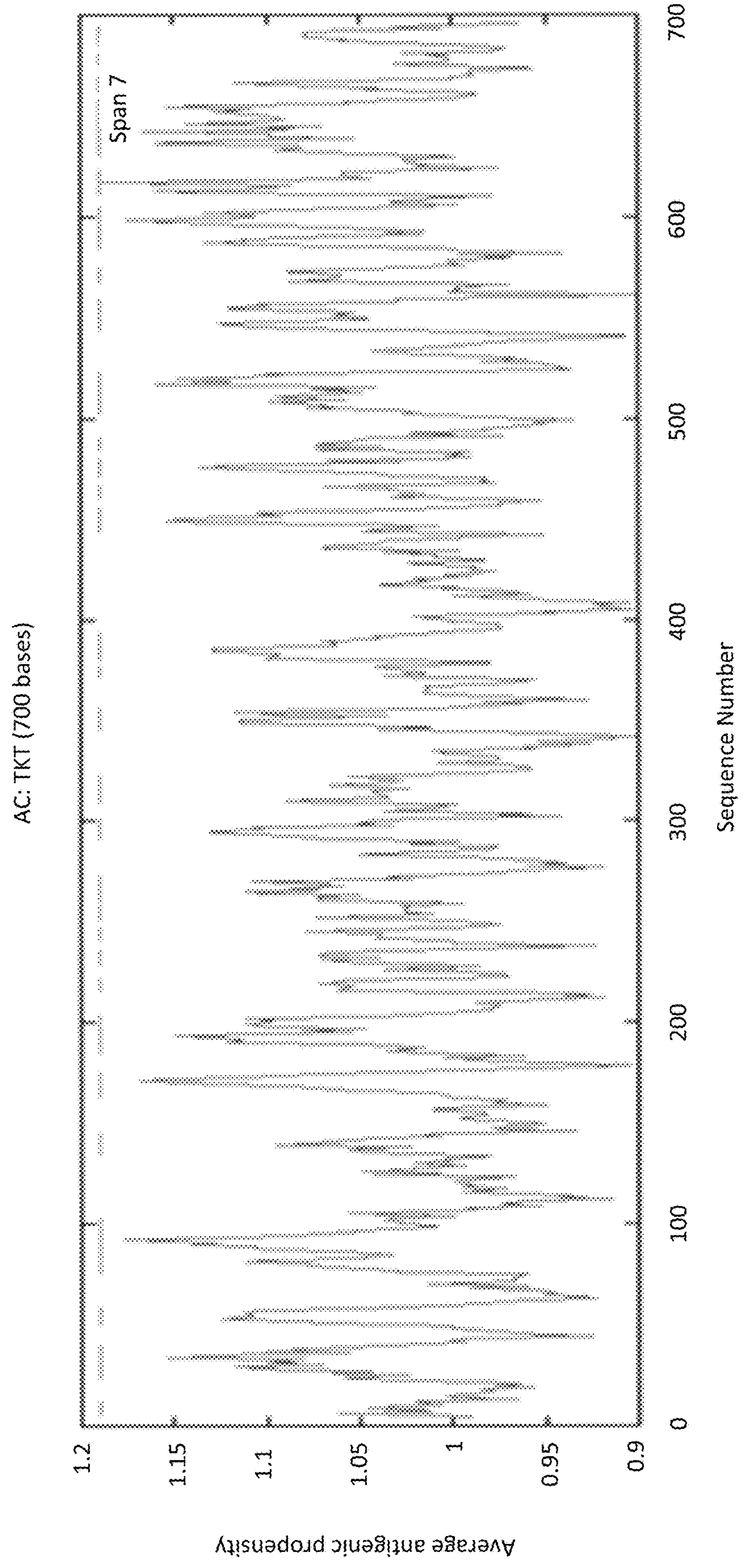
FIG. 3. Antigenic determinants plot of M.tb TKT. Antigenic peptides of M.tb TKT were determined using the method of Kolaskar and Tongaonkar (*FEBS Let.* 276(1-2): 172-174, 1990), an antigenic peptide prediction tool (OptimumAntigen Design Tool, e.g., as available from GenScript, Piscataway, NJ). There were 30 antigenic determinants in M.tb TKT sequence. TKT-μ, M.tb TKT1 and M.tb TKT3 peptides represent the antigenic determinants in the region spanning between sequence number 500-600.

TKT-sequence alignments of *Mycobacterium tuberculosis, Homo sapiens* and *Staphylococcus aureus*. TKT is an evolutionary conserved enzyme and ubiquitously present from microorganisms to humans, but there are inter- and intra-species variations in gene and protein sequences. Therefore, TKTμ was aligned with TKT of M.tb, *Homo sapiens* and *Staphylococcus aureus* (FIG. 2A). TKT structure from most of species is arranged into three domains: Domains I (1-322), II (323-527), and III (528-700). Domain III comprises the last approximately 170 amino acids and is involved in the regulation of the enzyme activity and most mutations have been reported in this domain (Fullam et al., Open Biol, 2(1): 110026, 2012). M.tb TKT has 26% sequence homology with *Homo sapiens* and 43.8% with *S. aureus* transketolase. It was found that the TKTμ peptide (17AA) has similarity to M.tb transketolase on the AA sequence of THQPI (SEQ ID NO: 1), spanning from AAs 562-566 of M.tb TKT (FIG. 2B) and is the core domain III of M.tb TKT, which is the part of the open reading frame containing a specific sequence motif of THDSIGLGEDGPTHQPIE (SEQ ID NO: 2) (Fullam et al., Open Biol, 2(1): 110026, 2012). Because detection of abundance of IgG antibody against TKTμ epitope in sera of TB patients, it was asked if designing peptides corresponding only to M.tb TKT, but not the other organisms, could improve the sensitivity and specificity of ELISA. Therefore, three other peptides containing epitopes spanning the AA 541-570 of M.tb TKT protein were designed. These peptides were designed to include the adjacent AA present in TKTμ (SEQ ID NO: 12) epitope, THQPI (SEQ ID NO: 1), representing the antigenic determinants. These were TKT1: GEDGPTHQPIEHLSA (15 AA) (SEQ ID NO: 3), TKT2: DGPTHQPIEHLSALRAIPRLSV (22 AA) (SEQ ID NO: 4), and TKT3: HDSIGLGEDGPTHQPIEHLS (20 AA) (SEQ ID NO: 5) (FIG. 2B). Utilizing OptimumAntigen™ design tool, analyzed in silico the potential antigenicity of TKT peptides. The antigenicity is greater than 0.6, and the homology is less than 95%, the peptide is considered to provoke a good immune response. The in-silico analysis of TKT peptides indicated that TKTμ, M.tb TKT1 and M.tb TKT3 showed a good antigenicity. The antigenicity of TKTμ was 0.96 and homology 35/58% (*Mus musculus/Oryctolagus cuniculus*), TKT1 was 1.72 and homology 39/46% and TKT3 was 1.93, homology 29/34% (FIG. 3). The silico analysis indicated a lack of an antigenic property of TKT2 peptide.

Figure 4A:
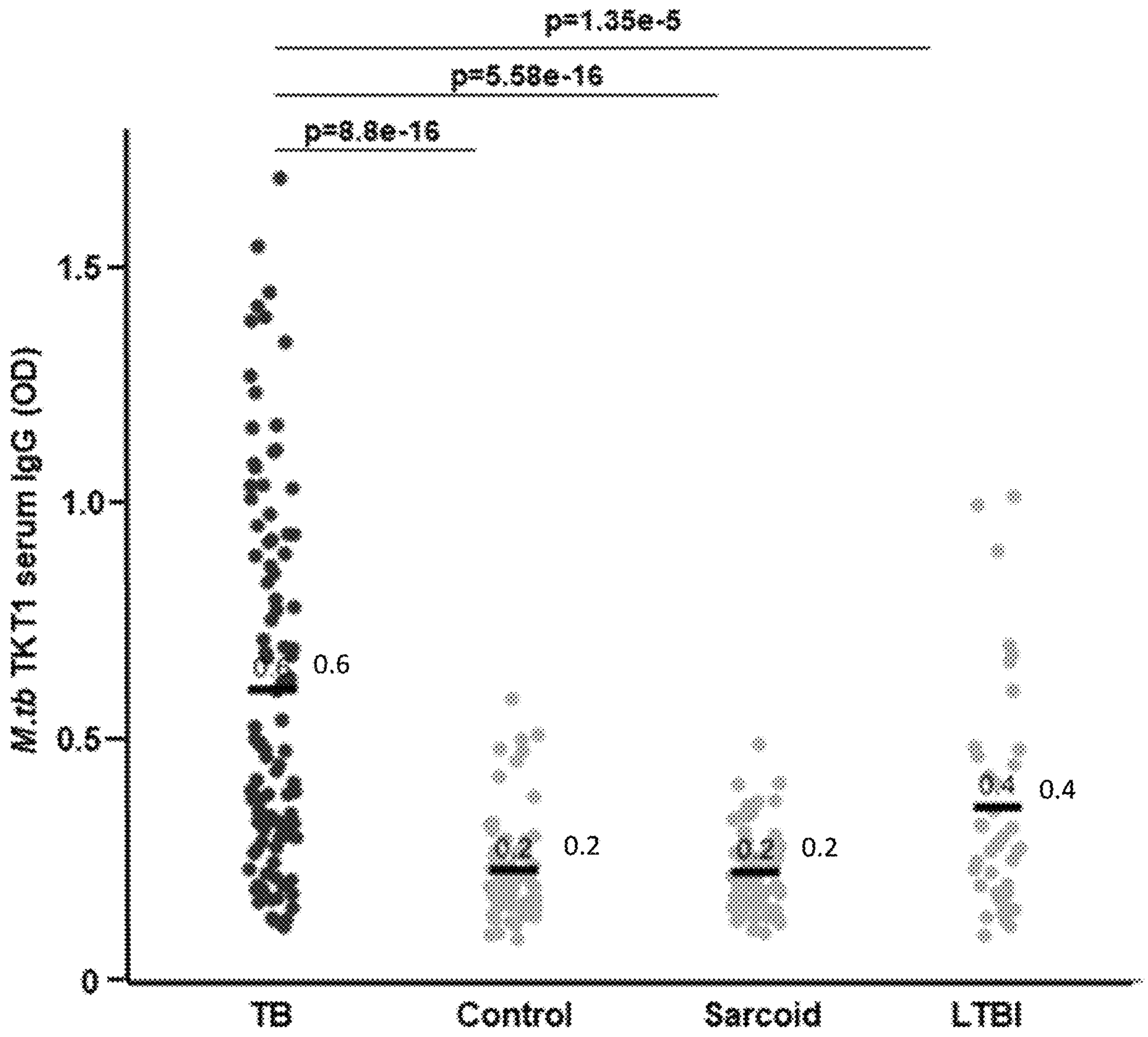
FIGS. 4A-4B. Evaluation of M.tb TKT1 and M.tb TKT3 specific IgGs in serum samples. M.tb TKTμ and M.tb TKT3 specific IgGs in serum of all study groups: healthy subjects (n=66), sarcoid (n=76), smear positive TB subjects (n=101) and LTBI (n=49) measured via direct peptide ELISA utilizing chemically synthesize M.tb TKT1 or M.tb TKT3 peptides. The comparison of immunoreactivity of serum IgGs to M.tb TKT 1 and M.tb TKT 3 peptides is presented as OD 450 nm.
Figure 4B:
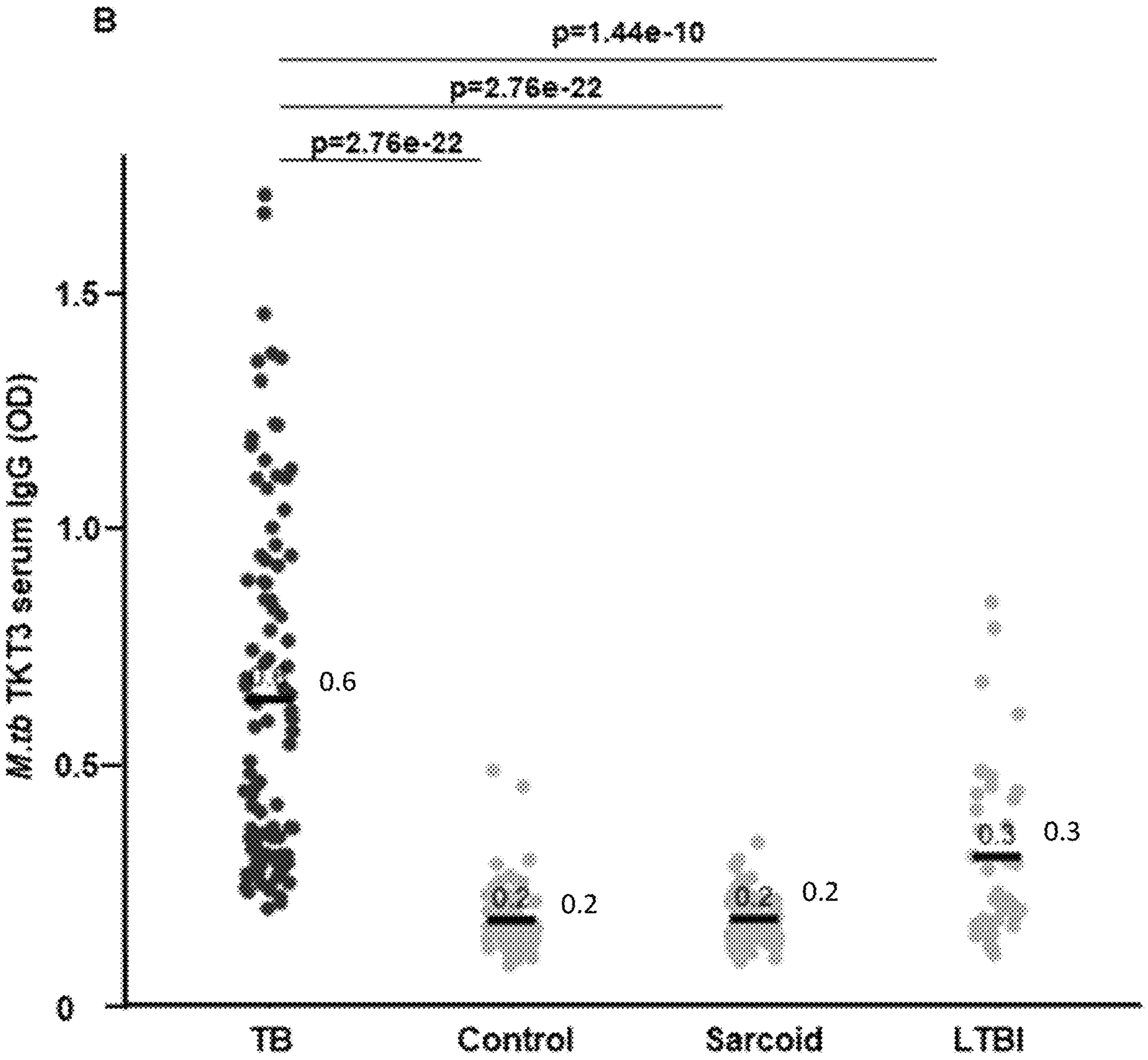

Detection of specific IgG against M.tb TKT epitopes. It was asked if the designed M.tb specific TKT epitopes (TKT1 and TKT3) have a better specificity and sensitivity to detect IgG in sera from active TB patients as compared to TKTμ. Similar algorithm was applied to develop and standardize the ELISA for each peptide sequences as described in Material and Methods. The immunoreactivity to M.tb TKT1 epitope presented as OD (FIG. 4A). As shown, the OD mean values in active TB was 0.61±0.39 that was significantly different comparing to OD values of healthy controls (adjusted p value=8.8 e-16), sarcoidosis (adjusted p value=5.8 e-16) and LTBI (adjusted p value=1.35 e-16). Similarly, TKT3 specific IgGs in all study subjects via ELISA were detected. The OD mean values against M.tb TKT3 in active TB was 0.62±0.35 that was significantly different comparing to OD values of healthy controls (adjusted p value=2.76 e-22), sarcoidosis (adjusted p value=2.76 e-22) and LTBI (adjusted p value=1.44 e-10) (FIG. 4B) These data indicate that both M.tb TKT1 and TKT3 peptides bind to specific IgG in sera from active TB and that and sera of active TB subjects exhibit significantly higher ODs compared to all other groups, even LTBI.

Figure 5A:
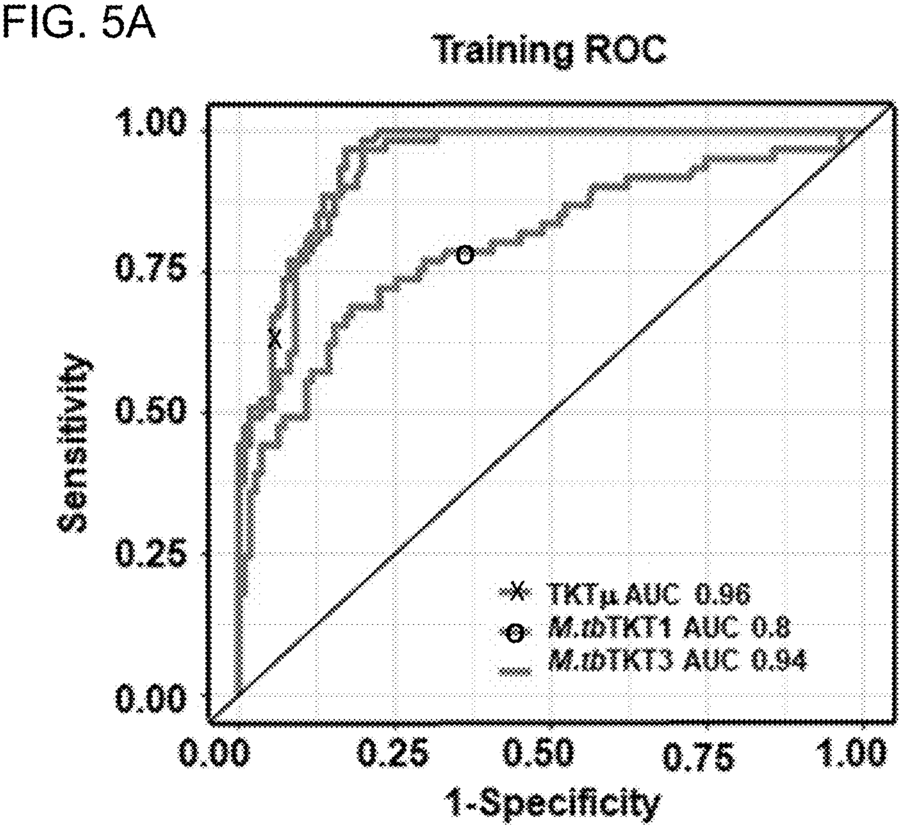
FIGS. 5A-5D. Classifications and receiver operating characteristic curve of TKT u, TKT1 and TKT3. A) Receiver operating characteristic (ROC) curves generated from training set (60% of samples) using IgG specific ODs against TKTμ, M.tb TKT3 and M.tb TKT1. The training set used to build a model and identify best threshold for IgG specific epitopes.
Figure 5B:
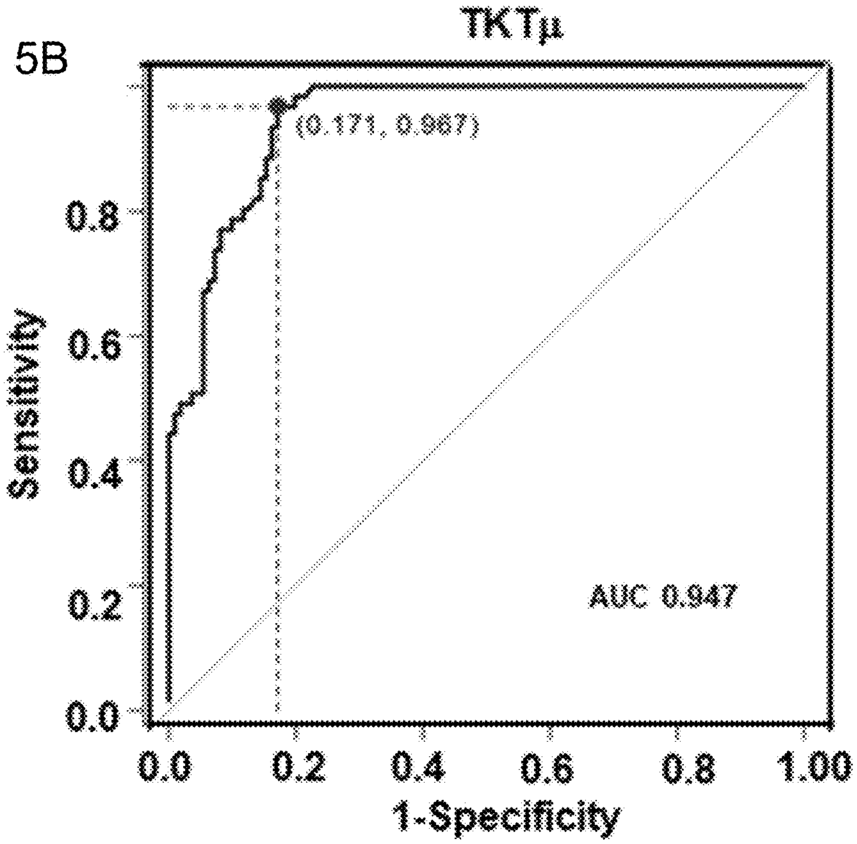
Figure 5C:
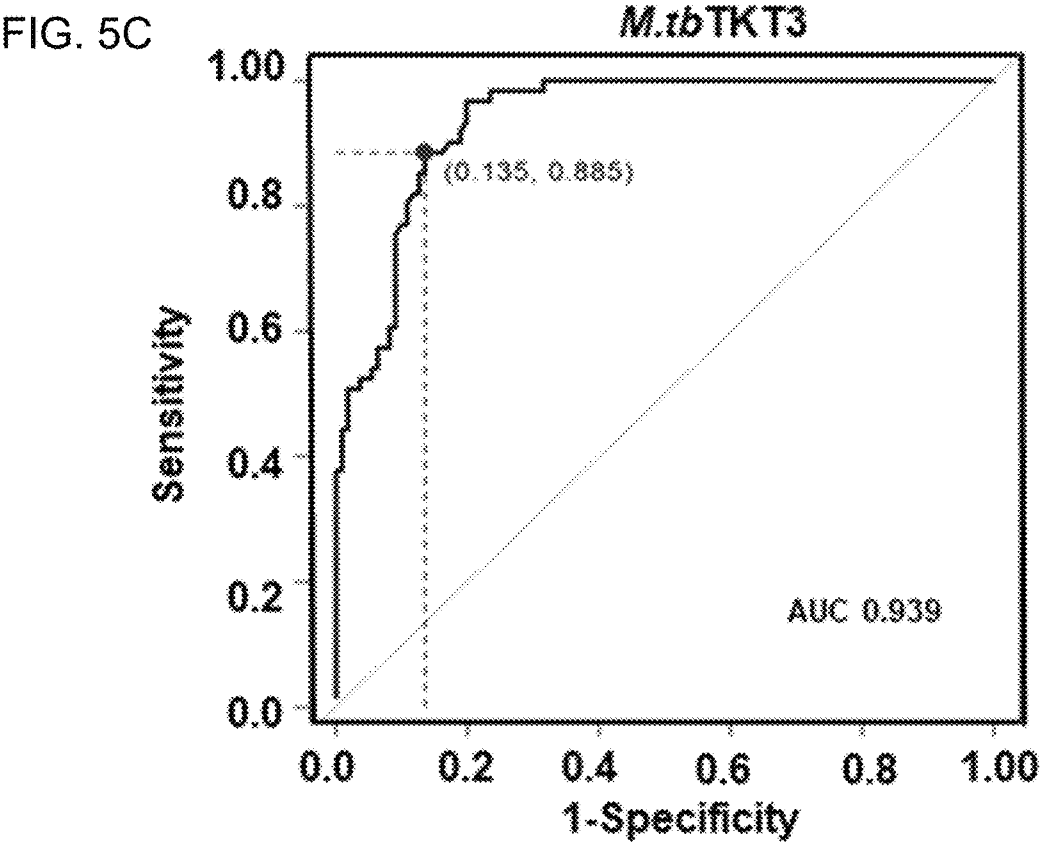
Figure 5D:
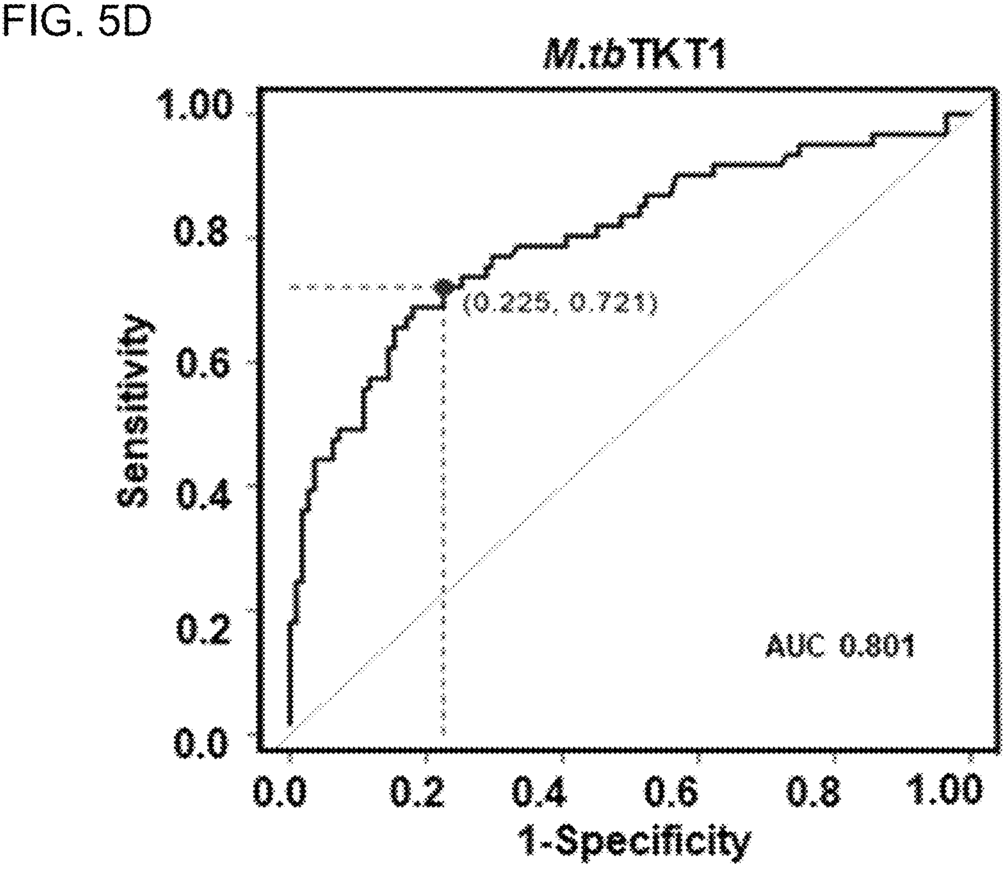

Classifications and ROC curves of TKT u, TKT1 and TKT3. To develop a model to classify active TB from other groups, first the data of all subjects (n=292) was randomly split into the training and test sets with a ratio of 60/40. Sixty percent of samples were assigned to the training set and the remaining were assigned to the test set (Table 3). Secondly, ROC curves were generated by using M.tb TKT 1, M.tb TKT3 and TKTμ data from training set (FIG. 4A). M.tb TKT1 ROC curve yielded an area under curve (AUC) of 0.8 (95% CI: 0.72-0.87) (FIG. 5A). M.tb TKT3 yielded an AUC of 0.95 (95% CI: 0.92-0.98). TKTμ yielded an AUC of 0.94 (95% CI: 0.91-0.97) (FIG. 4A). Based on the ROC curves, the best OD thresholds were identified for TKTμ, M.tb TKT1, and M.tb TKT3: 0.252, 0.293, and 0.267, respectively. Subsequently, these OD thresholds were applied to classify samples in the test data set and to assess the sensitivity, specificity, PPV, NPV, and accuracy. The model from training set was validated on the test set (40% of samples) and ROC curves were generated for all three peptides (FIGS. 5B-D). A sample was considered as "non-TB" if its serum IgG optical density was lower than or equal to the corresponding threshold and otherwise as TB. The classification with M.tb TKT3 on the test set yielded the highest sensitivity (0.845) followed by TKTμ (0.817), and M.tb TKT1 (0.732). The specificities obtained by TKTμ, M.tb TKT3, and M.tb TKT1 on the test sets are 1, 0.95, and 0.875, respectively. The model using TKTμ again obtained a perfect PPV of 1, followed by M.tb TKT3 with the PPV of 0.968 and M.tb TKT1 with the PPV of 0.912. The model with M.tb TKT3 had the highest NPV (0.776), followed by TKTμ (0.755) and M.tb TKT1 (0.648), all measured on the test set. The accuracy using TKTμ and M.tb TKT3 were equally good (both 88.3%), while the accuracy using M.tb TKT1 was 78.4%. These results clearly show that both ELISA based detection of IgG against M.tb TKT3 and TKTμ have great sensitivity, specificity, and accuracy to distinguish between active TB subjects from healthy controls, sarcoidosis and LTBI.

TABLE 3

Sample allocation in training and testing sets

| | Training | Testing |
|---|---|---|
| TB subjects | 61 | 40 |
| Controls | 42 | 27 |
| Sarcoidosis | 45 | 29 |
| LTBI | 24 | 15 |

Sample allocation of subjects in different groups for training and test sets. To develop a model to classify active TB from other groups, subjects were randomly split into the training and test sets with a ratio of 60/40.

Discussion

Figure 6:
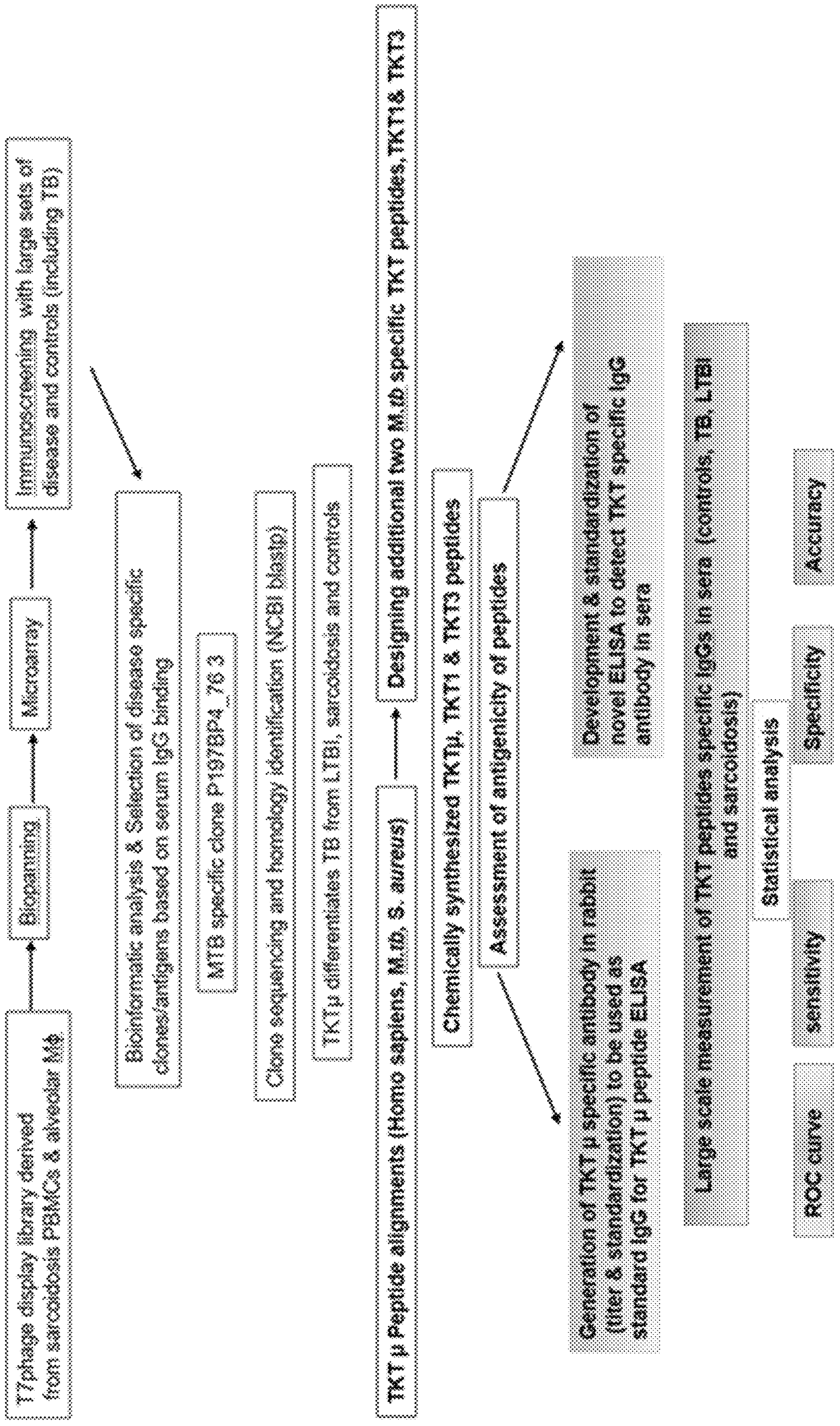
FIG. 6. Schematic representation of discovery and development of the highly specific and sensitive peptide-ELISA for detecting TKT-specific IgG antibodies in serum. Flow chart depicting the steps involved in discovery of TB specific clones utilizing T7 phage display library and immunescreening, identification of TKT epitopes, and the development of TKT peptide ELISA.

There is a need for a new conceptual approach to understand the complex host immune response to mycobacteria, including the mechanisms of humoral immunity (Melkie et al., Eur Respir Rev, 31, 2022; Kunnath-Velayudhan et al., Clin Microbiol Rev, 24(4): 792-805, 2011). The role of cell-mediated immunity in the defense against TB is well known, the role of antibodies in providing protection or their utilization as a diagnostic tool has not been well established (Winslow et al., Immunol Rev, 225:284-99, 2008; Achkar et al., Cell Host Microbe, 13:250-62, 2013). Most subjects developing TB are T cell competent, suggesting other possible immunological mechanism(s) underlying TB control (Giri et al., N Am J Med Sci, 5(6): 367, 2013). The elucidation of humoral immune responses to mycobacterial antigens seems to be difficult. Based on theoretical combinatorial calculations, the human antibody repertoire is estimated to include ~$10^{15}$ members (Rees A R., MAbs, 12(1): 1729683, 2020). This astronomical antibody repertoire is due to somatic diversification and gene rearrangement of immunoglobulins, VDJ recombination, T cells and MHC class diversity and interaction, and importantly mutations in M.tb genome among others (Briney et al., Front Immunol, 4:42, 2013; World Health Organization, Catalogue of mutations in *Mycobacterium tuberculosis* complex and their association with drug resistance. 2021). The evolutionary survival strategy of M.tb provided the advantage to balance species specific host responses, enabling the pathogen to remain dormant for a period of time by tuning down its' metabolism, resisting host responses and the actions of antibiotics (Gengenbacher et al., FEMS Microbiol Rev, 36:514-32, 2012; Brites et al., Immunol Rev, 264(1): 6-24, 2015; Saelens et al., Front Immunol, 10:528, 2019). Recent studies highlight the importance of humoral immunity and B cells in the defense against M.tb (Achkar et al., Cell Host Microbe, 13:250-62, 2013; Malik et al., J Exp Med, 191(2): 287-302, 2000). Immunoglobulin promotes phago-lysosomal fusion and intracellular killing through opsonization and engagement with FcγR (Ashenafi et al., Thorax 68(3): 269-76, 2013; du Plessis et al., Tuberculosis, 97:118-25, 2016; Kozakiewicz et al., PLOS Pathog, 9(7): e1003472, 2013; Walzl et al., Nat Rev Immunol, 11(5): 343-54, 2011). Studies showed that antibodies present in the sera of LTBI subjects exhibit enhanced phagolysosomal maturation, inflammasome activation, and macrophage killing of intracellular M.tb as compared to IgG present in sera from active TB subjects (Lu et al., Cell, 167(2): 433-43. e14, 2016; Rao et al., Clin Infect Dis, 61Suppl 3: S225-34, 2015). IgG antibodies may also gain access to the cytosol of M.tb-infected cells to promote growth restriction of intracellular bacteria (McEwan et al., Nat Immunol, 14(4): 327-36, 2013; Lu et al., Cell, 167(2): 433-43. e14, 2016; Rao M et al., Clin Infect Dis, 61Suppl 3: S225-34, 2015). The elucidation of humoral immune responses to mycobacterial antigens seems to be difficult. To this end, detection of humoral immune responses can be achieved by peptide microarrays, allowing the testing of several thousand unique epitopes displayed as linear peptides on a nitrocellulose coated glass slide in an unbiased fashion. This approach was utilized to develop a high-throughput method using a T7 phage display cDNA library derived from BALs and whole leukocytes of sarcoidosis subjects, and TKTμ was identified as one of the top 10 classifier clones distinguishing sera from active TB patients from uninfected control sera with a high sensitivity and specificity (Talwar et al., Viruses, 10(7), 2018; Talwar et al., EBioMedicine, 2(4): 341-50, 2015; Talwar et al., Mycobact Dis, 6(2): 214, 2016; Hanoudi et al., Mol Biomed, 3(1): 1-14, 2022). FIG. 6 illustrates the schematic diagram of the approach in discovery and development of the highly specific and sensitive peptide-ELISA for serological detection TKT-specific IgG antibodies. The TKT is a critical enzyme catalyzing the cleavage of carbon-carbon bonds to transfer two ketol carbon units from donor ketose sugars, like xylulose-5-phosphate, to acceptor aldose sugars, such as ribose-5-phosphate or erythrose-4-phosphate, resulting in the production of sedoheptulose-7-phosphate or fructose-6-phosphate. TKT has a critical role in carbon branching in bacterial growth including M.tb (Fullam et al., Open Biol, 2(1): 110026, 2012; Sundström et al., J Biol Chem, 268(32): 24346-52, 1993) and depletion of TKT changes the M.tb virulence (Kolly et al., FEMS Microbiol Lett, 358(1): 30-5, 2014). Because the dormancy/non-replicative phase of M.tb is characterized by low metabolic rate and a lower M.tb cell division (Talwar et al., Mycobact Dis, 6(2): 214, 2016), an ELISA for TKT specific epitopes was developed to test if IgG against any TKT epitope can differentiate between active TB and LTBI. As TKT plays a key role in the switch from the dormancy to proliferative phase and TKT specific IgG may uncover the differences between active TB and LTBI. The study showed that both TKTμ and M.tb TKT3 peptides are specific and sensitive to detect IgG against TKT and both can be used to develop sensitive direct peptide ELISA or POC test such as lateral flow to differentiate TB from other conditions. Evaluating a large diverse collection of samples and developing a statistical classification model using training and test sets, M.tb TKT3 epitope yielded the highest sensitivity (0.845) followed by TKTμ (0.817), and M.tb TKT1 (0.732). The specificity obtained by TKTμ, M.tb TKT3, were 1, 0.95 respectively. The specificity of M.tb TKT1 peptide ELISA was the lowest (0.875). Despite a 75% sequence similarity between M.tb TKT1 and M.tb TKT3, there were differences in the sensitivity and specificity of these two peptides. These differences appear to be due to the five N-terminal AA's that may confer conformational changes affecting the affinity/avidity of IgG bindings to these epitopes. By applying whole genome sequencing of M.tb of clinical isolates, a recent study showed a significant genetic heterogeneity and a large number of single nucleotide variants (SNV) and that even one SNV can affect drug susceptibility and resistance (Advani et al., Front Microbiol, 10:309, 2019). Interestingly, beside well-described SNV in rpoB gene leading Xpert MTB/RIF, they found numerous SNVs in metabolic genes, including the M.tb TKT gene (Advani et al., Front Microbiol, 10:309, 2019; Ullah et al., BMC Infec Dis, 16:1-6, 2016). Therefore, it is conceivable that the differences in N-terminal AAs affect the antigenicity and the antibody responses.

Current non-sputum based POCs either detect various M.tb antigens, including lipoarabinomannan (LAM), culture filtrate proteins (CFPs), and ESAT-6, or detect host antibody responses to M.tb (Hong et al., Sci Transl Med, 14:eabj4124, 2022; Peter et al., Lancet, 387:1187-97, 2016). Sensitivities and specificities of antigen-based POCs are lower than the ideal and variable based on the patient population, including hospitalized patients versus outpatient or HIV status (Hong et al., Sci Transl Med, 14:eabj4124, 2022; World Health Organization, Lateral flow urine lipoarabinomannan assay (LF-LAM) for the diagnosis of active tuberculosis in people living with HIV: policy update (2019): evidence to decision tables. 2019). Among these tests, WHO endorsed lateral flow urine LAM assay to aid TB disease diagnosis in HIV-positive patients (World Health Organization, Lateral flow urine lipoarabinomannan assay (LF-LAM) for the diagnosis of active tuberculosis in people living with HIV: policy update (2019): evidence to decision tables. 2019). LAM is a ubiquitous mycobacterial component, has low specificity for distinguishing M.tb from nontuberculous mycobacteria (NTM) that is important in HIV infected subjects (Liu et al., Int J Infect Dis, 118:65-70, 2022). There are few serological tests available that quantitate the TB specific antibodies in the serum. The InBios Active Tb Detect IgG ELISA assay that uses pool of M.tb antigens was found to be sensitive to detect active TB (Omrani et al., Pak J Biol Sci. 12(4):373-377, 2009; Welch et al., Clin Vaccine Immunol, 19(4): 522-6, 2012). Other available tests for TB serodiagnosis utilizing various components of M.tb, including, Ag60 complex (Grubek-Jaworska et al., Int J Tuberc Lung Dis, 1(6): 556-62, 1997; Alifano et al., Thorax 53(5): 377-80, 1998), PPD (Zeiss et al., Rev Respir Dis, 130(5): 845-8, 1984) or a pool of membrane and secreted antigens from M.tb H37Rv (Målen et al., Scand J Immunol, 67(3): 245-52, 2008). Most these tests utilized either a single specific antigen or a pool of membrane or secreted M.tb antigens containing various potential epitopes. Only a few studies included LTBI to assess specificity and sensitivity (Wang et al., Int J Infect Dis, 70:1-9, 2018).

Target product profiles (TPPs) issued by the WHO defining non-sputum-based rapid biomarkers performance as a triage test recommended to have a sensitivity >95%; and a specificity >80% to screen patients with suspected TB disease and to reduce the population that requires confirmatory tests (Hong et al., Sci Transl Med, 14:eabj4124, 2022; Melkie et al., Eur Respir Rev, 31, 2022). The data indicate that the TKT specific ELISA tests fulfill these criteria and are suitable for this purpose. Furthermore, combination of three epitopes may increase specificity and sensitivity of the test.

Efficacy studies from advanced TB vaccines designed to stimulate cell-mediated immunity failed to show consistent protection, warranting the need of harnessing other types of immunity, including antibody and B cell responses (Melkie et al., Eur Respir Rev, 31, 2022; Achkar et al., Cell Host Microbe, 13:250-62, 2013; Lu et al., Cell, 167(2): 433-43. e14, 2016). One important consideration is that if the TKTμ, M.tb TKT1 and M.tb TKT3 can serve as vaccine candidates. There are some important facts may favor potential utility of TKT peptide as a vaccine candidate: First, the current data that TB subjects exhibit antibody against TKTμ, M.tb TKT3 and M.tb TKT1 epitopes. Second, that excellent antibody responses can be evoked in TKTμ immunized rabbits suggesting humoral response to TKT epitopes. Third, that TKT enzyme is important for M.tb bacterial growth and IgG antibody levels were different in TB subjects versus LTBI. Further experiments in animal models of M.tb infection can provide invaluable information.

This study has certain noteworthy limitations. First, like any other human study, it is prone to bias due to unmeasured confounders. Second, prospective studies or measurement of TKT antibodies in collected sera at the completion of anti-tuberculosis treatment can provide insight into the value of treatment success. Third, further testing is required in subpopulations of immunocompromised subjects such as HIV patients. Fourth, assessments of TKT antibodies in sera of subjects with culture and smear positive for NTM species are required to evaluate diagnostic accuracy of this test. Because IgG subclasses may affect the bacterial clearance as well as Fcγ receptor activation, further studies are needed to evaluate TKT specific IgG subclasses.

Example 2: ELISA Development and Standardization

Figure 7:
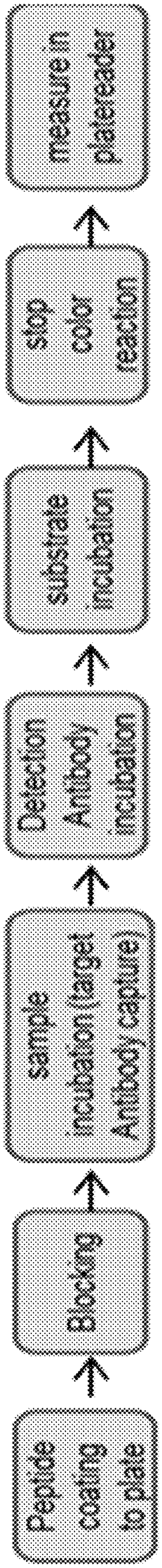
FIG. 7. A generalized workflow for performing an ELISA.

Direct peptide ELISA (enzyme-linked immunosorbent assay) is a powerful method for detecting and quantifying specific antibody against protein regions or antigens. The Peptide-ELISA developed, requires peptide to be immobilized onto a plate surface, and the specific antibody in human serum be captured during incubation, then an HRP conjugated complementary detection antibody binds to the complex of peptide and antibody, and the substrate is added and finally the enzyme, HRP bound to detection antibody, reaction and development of color with substrate. The color change in the plate is then measured as an optical density (OD) in a plate reader. The generalized workflow for performing this ELISA is as shown in FIG. 7. While the ELISA protocol is conventional, for the direct ELISA, there was a need to standardize it step by step based on the experiment's result.

1. Plate Selection

First of all, the selection of plate is very important step in the whole procedure. As the platform for all reactions, the peptides should bind the plate firmly, and combine unwanted organic group in samples as less as possible. The most popular ELISA plates available in market were chosen, from R&D, ThermoFisher and also a NeutrAvidin coated plate from ThermoFisher, and either of them was referred in previous publications. The ELISA was run with several of plates parallelly under same treatments and conditions with sera from patients and healthy controls samples. Among them, the OD value R&D plate showed was around 0.6~3, while the ThermoFisher plate showed only 0.2~0.6, although both of them showed difference between patients' group and control group. Therefore, the R&D plate was chosen. Also, the strips and frame design of R&D plate is easy to disassemble and insert, offering the best convenience for the experiments operating.

The R&D plate was selected for the ELISA experiments.

2. Coating Buffer Selection

The coating buffer dissolves the peptide and help to immobilize the peptide to the plate surface. Currently, the carbonate coating buffer and PBS are commonly used as coating buffer. Both the coating buffers were used in the experiments, and there was not much difference between them.

PBS was selected as the coating buffer because it is the most common solution available in most labs and easy to prepare.

3. (A) Coating Concentration of Peptide and Coating Condition

Normally 0.1 μg/mL-10 μg/mL peptide is coated onto plate in research, and an ELISA was performed with gradient peptide concentration with serum samples (pure target antibody standard), to optimize the peptide concentration for coating, and the result is as following.

According to this result, it was found that 500 ng/ml of peptide is approaching maxima point of coating concentration, and the higher concentration did not increase OD significantly. It was determined that 500 ng/ml is the coating concentration.

TABLE 4

| Peptide | OD450 in duplicate wells | |
|---|---|---|
| 2000 ng/ml | 3.364 | 3.281 |
| 1000 ng/ml | 3.285 | 3.252 |
| 500 ng/ml | 3.138 | 3.072 |
| 250 ng/ml | 2.785 | 2.71 |
| 125 ng/ml | 2.342 | 2.25 |
| 62.5 ng/ml | 1.563 | 1.52 |
| 31.25 ng/ml | 0.85 | 0.884 |
| No peptide | 0.047 | 0.047 |

To acquire the best coating condition, two general methods were used: overnight coating at room temperature, and 2 hours coating at 37° C. as comparison. Both methods worked well, the former showed less difference between the OD of duplicated wells, and did not require any heater or incubator to perform this step.

Overnight coating of plate with 500 ng/mL of peptide was standardized.

(B) N- or C-terminal Biotinylated Peptide for Coating the Plates

To determine if the efficiency of immobilization of the peptide to the plate can be optimized, the N- or C-terminal Biotinylated peptide was synthesized. Biotinylated peptide binds to the Avidin, NeutrAvidin or streptavidin coated surface. NeutrAvidin coated plates and biotinylated peptide (TKT-μ) were used to perform ELISA. The results are shown below in Table 5.

TABLE 5

| Biotinylated N-TKT | TB serum (1:500) | TB serum (1:1000) | No serum, with detection Ab | No serum, No detection Ab |
|---|---|---|---|---|
| 0 ng/mL | 0.428 | 0.246 | 0.059 | 0.046 |
| 500 ng/mL | 0.541 | 0.356 | 0.073 | 0.047 |
| 1000 ng/mL | 0.593 | 0.339 | 0.068 | 0.048 |
| 2000 ng/mL | 0.565 | 0.359 | 0.069 | 0.056 |
| 3000 ng/mL | 0.685 | 0.41 | 0.067 | 0.047 |
| 4000 ng/mL | 0.683 | 0.446 | 0.075 | 0.054 |

The results showed that ELISA performed with biotinylated peptide (TKT-μ) didn't give the reliable results at any of the peptide concentration used.

4. Washing Buffer Selection and Washing Times

The washing step wash off the reagents that are not bound, and thus avoids the background noise reading caused by the unbound sample components or reagents. The most used washing buffer recipes that were found were TBS or PBS with 0.5%. Tween-20, and most ELISA procedure suggests 3 or 4 times washing between each incubation step.

Two washing buffers were used, and there was not much difference between two washing buffers, and PBS with 0.5%. Tween-20 (PBST) was selected, because PBS is the most common solution in labs as well as a non-toxic solution.

The washing was standardized with PBST buffer and three times washing.

5. Blocking Buffer and Assay Buffer

The purpose of blocking is to mask the nonspecific organic group that may bind to the surface of the plate, and hence to avoid noise reading.

An assay buffer is to dilute sample (serum) and detection antibody. In this protocol, the same buffer was used for both blocking buffer and assay buffer.

For comparison, 3 types of blocking buffers such as 5% BSA in PBST, 5% non-fat milk in PBST were used, and also one commercial blocking buffer from Bio-Rad named EveryBlot blocking buffer. The 5% non-fat milk in PBST and the commercial blocking buffer showed less noise in final reading in the experiments. Because the 5% milk have to be freshly made and it could not be preserved for long time, EveryBlot blocking buffer was chosen as the blocking and assay buffer.

6. Serum Sample Dilution

Figure 8:
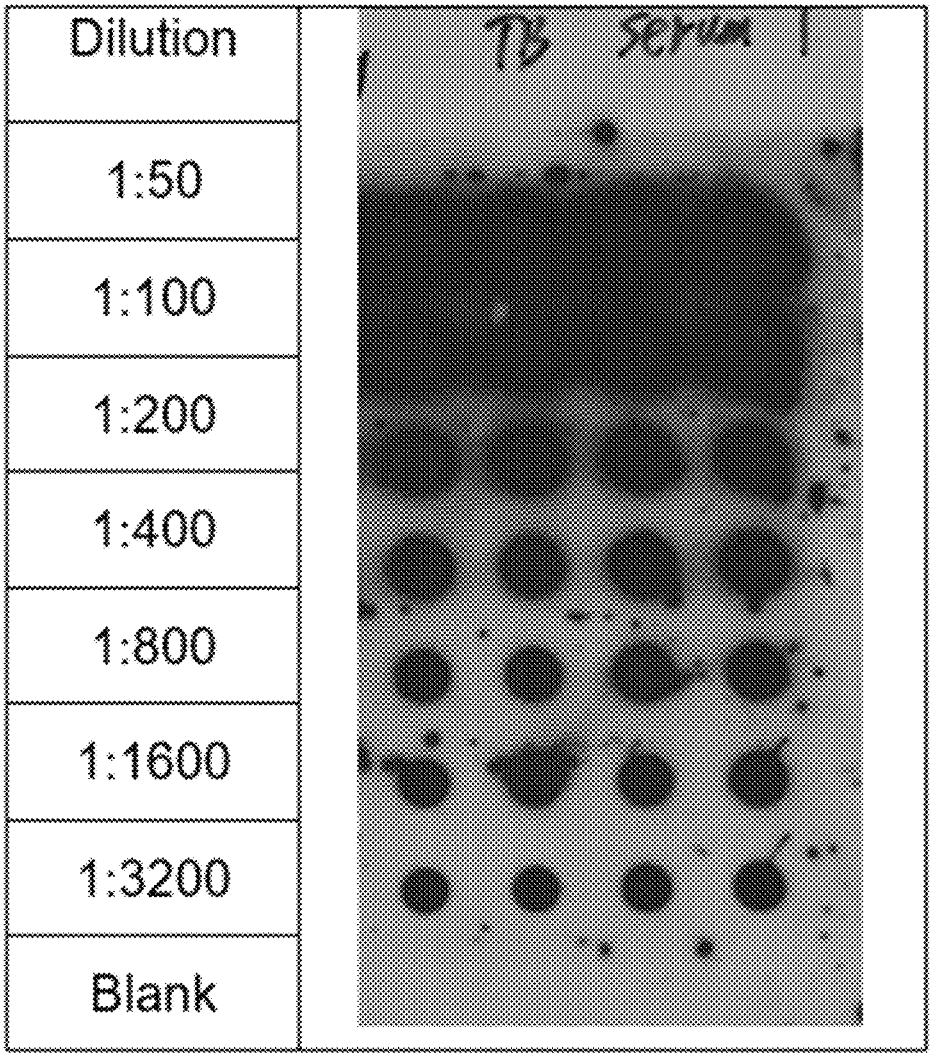
FIG. 8. An image of a dot blot from testing TB serum dilution range of 1:50 to 1:3200 dilution.

In the experiments, the human sera were the study samples. To minimize the noise caused by non-specific antibody binding, the serum should be generally diluted 1:50 or more. A Dot-blot experiment was done to estimate the best dilution for serum sample. The Dot blot in FIG. 8 shows that the dots were strong and clear in the dilution range of 1:400-1:800 dilution.

Figure 9:
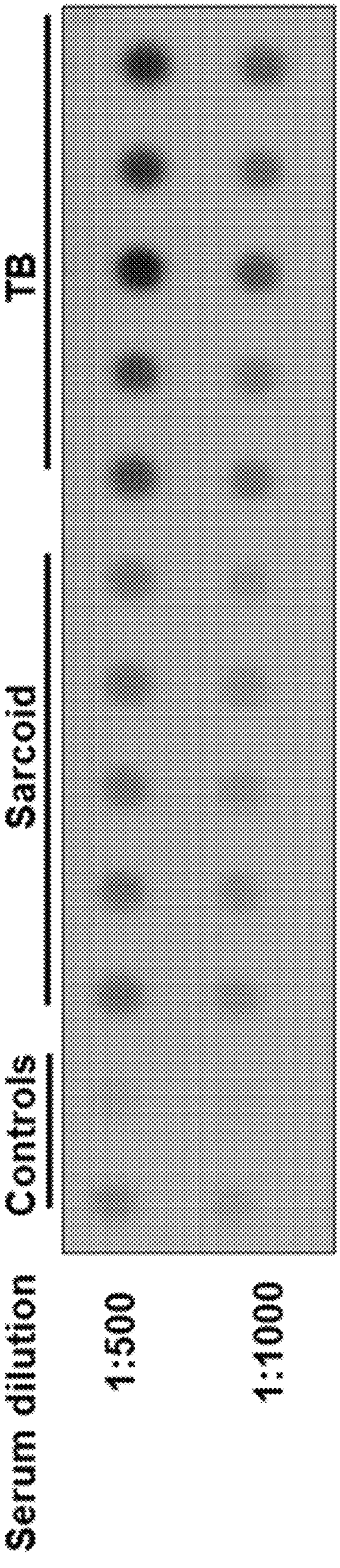
FIG. 9. An image of a dot blot from testing 1:500 and 1:1000 dilutions of serum from controls (C1-C2), sarcoid (S2-5) and TB (1-5) groups.

Following that, both 1:500 and 1:1000 serum dilutions were tested in Dot blot with Controls (C1-2), sarcoid (S2-5) and TB (1-5) serum (FIG. 9).

Both the dilutions in ELISA were tested. The OD value at 1:500 dilution was higher and had much difference between each group. Finally, the sample dilution as 1:500 was decided. The results are shown in Table 6.

TABLE 6

| | TB sera 1:500 | TB sera 1:1000 |
|---|---|---|
| TB01 | 1.0975 | 0.559 |
| TB02 | 1.3495 | 0.5545 |
| TB03 | 0.98 | 0.46 |
| TB04 | 0.8405 | 0.4995 |
| TB05 | 0.66 | 0.367 |
| TB06 | 0.97 | 0.6445 |
| TB07 | 0.6815 | 0.33 |
| TB08 | 0.5805 | 0.2725 |
| TB09 | 0.815 | 0.452 |
| TB10 | 0.981 | 0.419 |
| Control 1 | 0.642 | 0.354 |
| Control 2 | 0.5465 | 0.2495 |
| Blank | 0.06 | 0.06 |

The serum sample dilution (in EveryBlot blocking buffer; Bio-Rad Laboratories, Inc.) was standardized to be used as 1:500.

7. Sample Loading

To minimize the operating deviation in experiments, 100 ml of diluted serum sample was loaded in duplicates in each experiment, and the final result was the average of two values. The deviation between duplicated wells was minimized by using a multichannel pipet and good pipetting skill.

Figure 10:
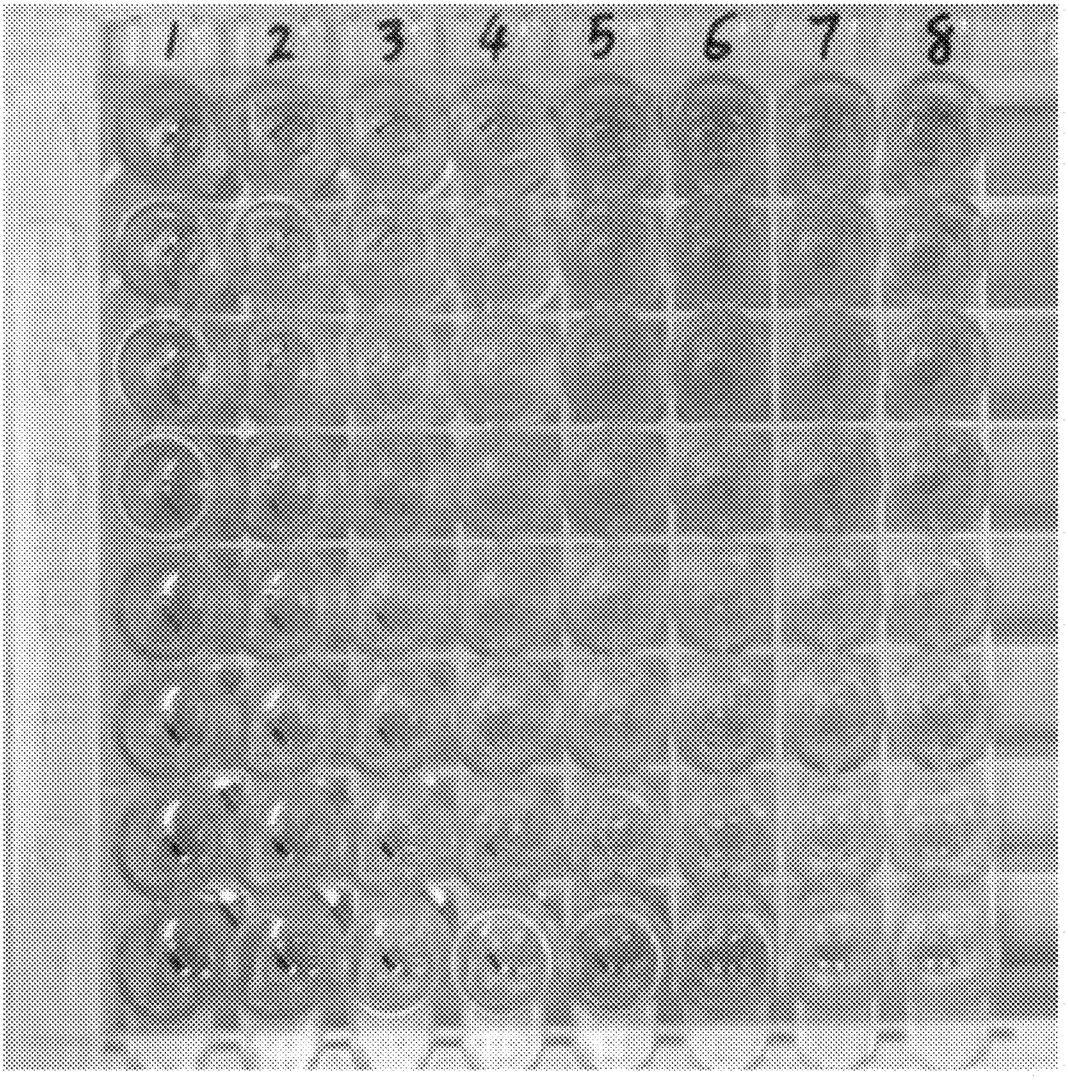
FIG. 10. An image of a plate from testing duplicates of diluted serum sample.

As an example, a picture of the plate and the reading (OD) are shown in FIG. 10 and as quantified in Table 7. To add 100 ml of diluted serum sample in duplicates was standardized.

TABLE 7

| | 1 | 2 | 3 | 4 | 5 | 6 | 7 | 8 |
|---|---|---|---|---|---|---|---|---|
| A | 0.447 | 0.464 | 0.285 | 0.228 | 2.135 | 2.412 | 0.824 | 1.307 |
| B | 0.247 | 0.217 | 0.237 | 0.198 | 1.185 | 1.343 | 0.469 | 0.442 |
| C | 0.385 | 0.348 | 0.124 | 0.124 | 1.839 | 2.05 | 0.848 | 0.873 |
| D | 0.462 | 0.521 | 0.634 | 0.421 | 0.924 | 0.868 | 0.936 | 0.98 |
| E | 0.331 | 0.278 | 0.204 | 0.217 | 0.328 | 0.286 | 0.196 | 0.205 |
| F | 0.356 | 0.389 | 0.575 | 0.474 | 0.424 | 0.713 | 0.554 | 0.602 |
| G | 0.436 | 0.441 | 0.337 | 0.485 | 0.704 | 0.65 | 0.172 | 0.145 |
| H | 0.758 | 0.707 | 0.053 | 0.053 | 3.669 | 3.338 | 0.074 | 0.071 |

8. Detection Antibody Selection

The detection antibody is an enzyme conjugated secondary antibody that is complementary to the primary antibody. Since the sample was human serum sample and the objective of the ELISA is to detect peptide-specific IgGs (primary antibody) in serum that bind to the coated peptide on plate, therefore an HRP conjugated anti-human IgG antibody as detection antibody was used. Detection antibody binds to the peptide-IgG complex bound to the plate.

There were lots of products available in market. HRP-conjugated Rabbit Anti-Human IgG H&L and HRP-conjugated Goat anti Human IgG-HRP was selected for standardization. Finally, the HRP-conjugated Goat anti Human IgG from Abcam was chosen, one of famous global protein research companies.

According to the protocol of analogous ELISA, the plate was incubated with detection antibody at room temperature for 90 minutes, and the dilution was 1:5000.

HRP-conjugated Goat anti Human IgG as detection antibody to be used at 1:5000 dilution in EveryBlot blocking buffer, and incubation time of 90 minutes was standardized.

9. Substrate Selection

Currently, there are five major substrates in developing color for ELISA. Among them, TMB is often used for HRP detection because it develops color faster, and it is more sensitive than other substrates. Since the HRP conjugated detection antibody was used, the TMB was used as the developing substrate.

10. Plate Reader

A Biotek Synerty H1 plate reader was applied for the measurement, which is a multi-function plate reader that can be used to read absorbance, luminescence, and fluorescence. And the best way can be chosen to translate the color changes in plate into digital measurement.

11. Standard Curve for TKT-μ Peptide ELISA.

To quantitate the concentration of TKT-μ specific IgGs in serum samples, rabbit anti-TKT-μ IgG was generated by immunizing the rabbit with TKT-μ peptide.

Briefly, TKTμ peptide was conjugated to the carrier protein KLH, 0.2 mg TKTμ peptide-KLH conjugate with Freud's complete adjuvant was administered subcutaneously per rabbit (New Zealand strain). Subsequently, three booster doses of conjugated TKTμ peptide (0.2 mg/rabbit) were given on days 14, 28 and 42. The serum from the immunized rabbits was collected on day 49 and pooled and the polyclonal anti-TKTμ IgGs were purified by using antigen affinity purification method.

Rabbit anti-TKTμ IgG was used to generate standard curve (OD vs anti-TKT-μ IgG) for TKT-μ peptide ELISA as shown in FIG. 1B.

The standard curve for TKT-μ peptide ELISA to calculate the concentration of TKT-μ specific IgGs in the serum samples was standardized.

12. Titration of TKT-μ Specific IgG Antibodies in Serum Samples

To determine the titer of antibodies in each serum sample, direct TKT peptide ELISA was performed using serial dilutions of the serum starting from 1:250 to 1:16,000. To measure the titer of antibody in the serum, OD of test/OD of Blank for each sample was calculated. It was standardized that the antibody titer is the highest dilution when Test/Blank (T/B)>=2.1. The healthy control was compared with TB patients. Table 8 shows the representative TKT-peptide ELISA results obtained from few of the patients and healthy control.

TABLE 8

| | Subject | | | | |
|---|---|---|---|---|---|
| Serum dilution | C45-1 | TB01 | TB10 | TB11 | TB17 |
| Serum 1:250 | 0.57 | 1.18 | 1.125 | 1.412 | 1.423 |
| Serum 1:500 | 0.392 | 0.931 | 0.873 | 1.141 | 1.259 |
| Serum 1:1000 | 0.334 | 0.73 | 0.718 | 0.865 | 1.057 |
| Serum 1:2000 | 0.218 | 0.571 | 0.533 | 0.644 | 0.837 |
| Serum 1:4000 | 0.172 | 0.381 | 0.39 | 0.425 | 0.624 |
| Serum 1:8000 | 0.147 | 0.26 | 0.27 | 0.251 | 0.438 |
| Serum 1:16000 | 0.101 | 0.188 | 0.221 | 0.166 | 0.358 |
| Blank | 0.071 | 0.067 | 0.06 | 0.059 | 0.06 |
| Test/Blank (1:16000) | 1.422535211 | 2.805970149 | 3.683333333 | 2.813559322 | 5.966666667 |

13. Advantages and Uniqueness of the Lab Developed TKT Peptide ELISA

Qualified tuberculosis biomarkers are most urgently needed for diagnosis, predictors of reactivation or cure, and indicators of vaccine-induced protection. However, serological diagnosis of tuberculosis has been challenging. Partly due to large Mycobacterial tuberculosis (M.tb) proteome and even larger antigenic epitopes. Additionally, there is heterogeneity across humans in development of immunoglobulin G (IgG) in response to tuberculosis. Diversity of M.tb antigens and diversity of human antibody repertoire in general and against M.tb antigens are major challenges to identify serological TB biomarkers Most tuberculosis serological tests that are commercially available use purified M.tb proteins, a single or small number of antigens, predominantly derived from membrane proteins of M.tb. However, a unique neoantigen, TKT-μ that has sequence similarity to M.tb transketolase (TKT) enzyme, was discovered. TKT is an essential enzyme that is required for the intracellular growth of M.tb. The TKT-peptide ELISA results show that TB patients have significantly higher levels of TKT-specific antibodies as compared to healthy controls and Latent TB (LTBI). The increased levels of TKT-specific antibodies is presumably associated with growing M.tb bacteria in active TB patients. TKT plays a key role in the switch from the dormancy to proliferative phase and TKT specific IgG may uncover the differences between active TB and LTBI. Thus, IgG based serodiagnosis of TB with TKT-peptide ELISA is promising.

Most of the serological TB tests utilize M.tb cell lysates or complex of 3-4 cell wall antigen peptides (e.g. Ag85 complex) or complex of recombinant antigens. However, to develop ELISA for the detection of human IgG against TKT epitopes (TKTμ, TKT3 and TKT1), selected peptides were chemically synthesized. There are several advantages of chemically synthesized: 1) short peptides are stable and easy to use for standardization as compared to purified antigens. 2) they bind selectively to the specific antibodies as they represent a single epitope. 3) there are less chances of cross-reactivity to other antibodies as seen with full-length proteins; and 4) the utilization of short peptides to detect IgG via ELISA increases the specificity of the assay, as the immunoreactivity depends on a single epitope.

Currently, commercially available serological TB tests show poor sensitivity and specificity. ELISA results obtained with the discovered TKT peptides yielded high specificity and sensitivity. Antibodies against M.tb TKT3 yielded the highest sensitivity (0.845) followed by TKTμ (0.817), and M.tb TKT1 (0.732). The specificities obtained by TKTμ, M.tb TKT3, and M.tb TKT1 on the test sets are 1, 0.95, and 0.875, respectively. The model using TKTμ obtains a perfect positive predictive value (PPV) of 1, followed by M.tb TKT3 with the PPV of 0.968 and M.tb TKT1 with the PPV of 0.912 These results show that IgG antibodies against transketolase can discriminate active tuberculosis.

Anti-TKT IgG that can be used to plot a standard curve to quantitate the TKT-specific IgGs in serum samples was successfully generated.

Example 3: Performance of Transketolase Immunoepitopes to Accurately Diagnose *Mycobacterium tuberculosis* Infection in a Mixed Patient Population Rapid, reliable tuberculosis (TB) diagnostic to differentiate active TB from non-nontuberculous mycobacterial infection (NTM) or granulomatous respiratory conditions are needed. The WHO defined high-priority target product profiles for TB diagnostics. Previously, three transketolase (TKT) epitopes that differentially bind to IgG in sera of TB patients were identified. Utilizing a peptide-based ELISA against TKT-epitopes, 510 samples from TB (n=148), LTBI (n=50), NTM (n=62), healthy controls (n=122), lung cancer (n=30), and sarcoidosis (n=98), were tested.

The diagnostic performance of TKT epitopes for TB involved three classification methods, receiver operating characteristic (ROC) by 10-fold cross-validation (CV), decision tree (DT), and random forest (RF). CV yielded a sensitivity, specificity, positive and negative predictive value (PPV, NPV) for TKTμ IgG-antibody of: 0.988, 0.879, 0.763 and 0.993; TKT1 IgG-antibody: 0.834, 0.754, 0.576 and 0.919; and TKT3 IgG-antibody: 0.891, 0.757, 0.599, and 0.945. TKTμ yielded two effective DT models: for TB and non-TB with 1.0, 0.886, 0.840, and 1.0; and TB, non-TB, and NTM with 1.0, 0.880, 0.815, and 1.0. Including NTM's TB's PPV and specificity decreased. The top RF model randomly drew from all three-epitope specific antibodies. Without NTM, TB diagnostics saw sensitivity (1.0), specificity (0.957), PPV (0.933), and NPV (1.0). Inclusion of NTM in the RF algorithm decreased sensitivity (0.886) and NPV (0.988), while specificity (0.975) and precision (0.943) increased. Highest TB diagnostic accuracies came from TKTμ and TKT1 CV (0.912), combination of three epitopes yielded the best DT (0.955) and RF (0.973). These results outperform current TB diagnostics in sensitivity, specificity, PPV, and accuracy.

Tuberculosis (TB) remains a serious global health threat with 10 million new cases and 1.7 million deaths each year (Nahid et al., *Am J Respir Crit Care Med* 184(8): 972-9, 2011; World Health Organization. *Global Tuberculosis Report* 2021: Supp. mat. 2022 (ISBN: 978-92-4-003702-1)). One third of the world's population is infected with TB but are not ill and are considered to have latent infections (Nahid et al., *Am J Respir Crit Care Med* 184(8): 972-979, 2011). The diagnosis of TB can be challenging, especially in the early stages, due to the variability in presentation and nonspecific signs and symptoms. A major obstacle to global control of TB remains inadequate case detection (Wallis et al., *Lancet* 375(9729): 1920-37, 2010). The existing TB diagnostic pipeline still does not have a simple, rapid, inexpensive point-of-care test (Id.). Currently, there are limited tools available to diagnose active TB, predict treatment efficacy and cure of active tuberculosis, assay the induction of protective immune responses through vaccination and to differentiate Nontuberculous mycobacteria (NTM) from TB. Active pulmonary TB is contagious and can be lethal, whereas NTM infections are not communicable, but may lead to significant morbidity and mortality in subjects with chronic lung disease, children, and immunocompromised subjects, including HIV patients and organ transplant recipients (Kendall & Winthrop, *Semin Respir Crit Care Med.* 87-94, 2013*; Lawn & Zumla, Lancet* 378 (9785): 57-72, 2011; Miguez-Burbano et al., *Inter J Infect Dis.* 10(1): 47-55, 2006; López-Varela et al., *Lancet Respir Med.* 3(3): 244-s56, 2015). NTM are microorganisms with considerable clinical relevance that are ubiquitously present in the environment and are commonly found in natural drinking water or soil (Adjemian et al., *Emerg Infect Dis.* 23(3): 439, 2017; Covert et al., *Appl Environ Microbiol.* 65(6): 2492-2496, 1999). The incidence of mycobacterial diseases caused by NTM infections has steadily increased globally over the last 60 years (Brode et al., *Int J Tuberc Lung Dis.* 18(11): 1370-1377, 2014) and causes a significant amount of morbidity, mortality, and financial health burden in certain regions of the world, including the United States (Brode et al., *Int J Tuberc Lung Dis.* 18(11): 1370-1377, 2014). The calculated age adjusted mortality rate in the US for TB was 3.3 per million person years and for NTM was 2.3 per million person years and this incidence is rising annually in individuals not living with HIV (Vinnard et al., *Ann Am Thorac Soc.* 13(11): 1951-1955, 2016). The inverse trend between mycobacterial infections are reflected globally (Ratnatunga et al., *Front Immunol.* 11:303, eCollection 2020). The NTM infection rates are increasing across 75% of geographic areas, whereas TB incidence decreased by 81% (Brode et al., *Int J Tuberc Lung Dis.* 18(11): 1370-1377, 2014). The increased incidence of NTM is attributed to climate change, as well as an increased number of immunocompromised subjects (Adjemian et al., *Emerg Infect Dis.* 23(3): 439, 2017; Adjemian et al., *Am J Respir Critical Care Med.* 185(8): 881-886, 2012; Dahl et al., *Int J Infect Dis.* 125:120-131, 2022; Falkinham, *Semin Respir Crit Car Med.* 95-102, 2013; Thomson et al., *Sci Total Environ.* 740:139796, 2020). NTM, comprising over 170 different species, is an emerging global health concern (Strollo et al., *Ann Am Thorac Soc.* 12(10): 1458-1464, 2015). Predominant NTM species causing significant pulmonary disease include *Mycobacterium avium* complex (MAC), *M. kansasii* and *M. abscessus* (Vinnard et al., *Ann Am Thorac Soc.* 13(11): 1951-1955, 2016). There are remarkable similarities in clinical features between TB and NTM infections, such as cough, low grade fever, weight loss and fatigue (Baldwin et al., *PLOS Negl Trop Dis.* 13(2): e0007083, 2019). These similarities result in misdiagnosis. Correct diagnosis and especially the treatment of NTM are difficult (Saleeb & Olivier, *Curr Infect Dis Rep.* 12(3): 198-203, 2010). Unfortunately, these patients are misdiagnosed as having active multidrug resistance TB infections and are usually given unnecessary treatments for MDR-TB (American Thoracic Society. *Am J Respir Crit Care Med* 152(6 Pt 1): 2185-2198, 1995 (doi.org/10.1164/ajrccm.152.6.8520796)).

Over the last decades, several research groups attempted to develop serological testing to detect active TB in endemic regions or differentiate active TB from LTBI. These attempts include utilizing several candidate TB antigens, such as LAM, 16 kDa, CFP-10, Rv3425, and antigen 60 (AG60) antibody detection tests (Wang et al., *Int J Infect Dis.* 70:1-9, 2018; Julián et al., *Clin Vaccine Immunol.* 11(1): 70-76, 2004). However, the diagnostic accuracy of these serological tests varies widely in performance and exhibit high inconsistency on their sensitivity and specificity depending on the population being tested. Currently, none of the commercial tests have performed well enough to replace sputum smear microscopy and the WHO does not indorse routine usage of these serological tests over sputum microscopy (World Health Organization. WHO operational handbook on tuberculosis: module 3: diagnosis: tests for tuberculosis infection. 2022 (ISBN: 978-92-4-005834-7)).

Recently, it was shown that an IgG based assay against TKT epitopes, including TKTμ and M.tb TKT1, M.tb TKT3 peptides is specific and sensitive to detect M.tb infection from other conditions (Talreja et al., *Microbiol Spectr.* 11(1): e03377-22, doi: 10.1128/spectrum.03377-22. Epub 2023 Jan. 18). It was hypothesized that TKT-epitopes specific IgGs also can differentiate TB from NTM infection. In the current study, the performance of IgG based immunoreactivity against TKT epitopes was assessed by including subjects with NTM infection. Three classification models, ROC by 10-fold cross validation, DT, and random forest, were applied to assess the performance of IgG specific antibodies against TKT-epitopes for correct TB diagnosis in a mixed population with various positive (diseased groups) and negative controls.

Materials and Methods

Chemicals and antibodies: ELISA plates were purchased from R&D systems (Minneapolis, MN), Goat anti-human IgG HRP-linked antibody was purchased from Abcam (Cambridge, MA), blocking buffer was purchased from Bio-Rad (Hercules, CA).

Patient Selection: This study was approved by the institutional review board at Wayne State University, and the Detroit Medical Center. All methods were performed in accordance with the human investigation guidelines and regulations by the IRB (protocol No=055208MP4E), at Wayne State University. All experiments were performed in accordance with guidelines and regulations of investigation of human subjects. Sera were collected from 6 groups: (1) healthy volunteers (n=122); (2) sarcoidosis subjects (n=98); (3) pulmonary TB patients (n=148), (4) latent TB (n=50), (5) NTM patients (n=62) and (6) lung cancer (LC) patients (n=30). All study subjects signed a written informed consent. Sera from patients with active and latent tuberculosis were obtained from the Foundation for Innovative New Diagnostics (FIND, Geneva, Switzerland). All TB patients from FIND had smear positive sputum. TB patients from Detroit were sputum smear negative but culture positive. Latent tuberculous infection (LTBI) subjects had negative smear and culture, but positive interferon gamma release assays (IRGs). NTM subjects had negative smear test for M.tb but positive for *M. avium* complex.

Sample size calculation and power analysis: Power and sample size were calculated using G power (Faul et al., *Behav Res Methods.* 39(2): 175-191, 2007). For the estimated effect size of 0.5-0.6 with a 90% power and a false discovery rate (FDR) of 1-5%, the required sample size for TB was n=48 and non-infected individuals (healthy controls) n=50. To reach higher power to near 100% and be able to validate the results on an independent set, the sample size was increased and disease controls of sarcoidosis subjects (n=98), LTBI (n=50), NTM (n=62), LC (n=30) and healthy controls (n=122) were included, while also increasing the TB subjects (n=148).

TKT peptide ELISA: TKT peptide ELISAs were performed according to a lab standardized ELISA (Talreja et al., *Microbiol Spectr.* 11(1): e03377-22, doi: 10.1128/spectrum.03377-22. Epub 2023 Jan. 18). Briefly, micro plates were coated with TKT peptide at the concentration of 500 ng/ml for overnight at room temperature (RT). The following day plates were washed 3× with washing buffer and were blocked at RT for 1 h with blocking buffer. After blocking, the plates were washed 3× with washing buffer, and serum samples (1:500) in duplicates were added onto wells and incubated at RT for 2 h. After 2 h, the plates were washed 3× and then incubated with goat anti-human IgG HRP linked secondary antibody at RT for 90 min. Plates were washed 4×, and TMB substrate mixture was added for 20 min at RT and the reaction was stopped by adding 50 ul of 2N $H_2SO_4$ to each well. The optical density (OD) was measured at 450 nm using a microplate reader (Biotek). Anti-TKTμ IgG was used to make the standard curve and the values of TKTμ IgG (μg/mL) in sera were calculated according to the standard curve.

Statistical analyses: The analyses of the ELISA data were performed in programming language R. A two-tailed Mann-Whitney test was applied to determine significant differences between groups. Subsequently, the significant scores p values were corrected for multiple comparisons using the false discovery rate method (FDR) (Benjamini & Hochberg, *J R Stat Soc Series B Stat Methodol.* 57(1): 289-300, 1995). The values of specific IgGs against TKTμ, TKT1, and TKT3 were utilized to develop classification models and receiver Operating Characteristic (ROC) curves to predict TB. The models were developed following 10-fold cross validation (CV). The data was split into 10 sets and each set was given an opportunity to be the test set. The ability to correctly identify TB among healthy controls, and various respiratory diseases, including LTBI, NTM, and sarcoidosis, was assessed. For each model, sensitivity, specificity, positive predictive value (PPV), negative predictive value (NPV), and accuracy were calculated by 10-fold cross validation (CV). The model is defined as the optimal cut point on the ROC obtained from the training set closest to the (1.0) point. The optimality criterion took the maximum of the sum of specificities and sensitivities, or Youden's J statistic. A sample was classified as TB infection if its serum IgG antibodies' ODs against specific TKTμ, TKT1, and TKT3 was greater than the OD threshold corresponding to this cut point. The ability to correctly identify TB and non-TB samples in the test set of each model based on the sensitivity, specificity, positive predictive value (precision or PPV), negative predictive value (NPV), and accuracy when applying the model on the test set was assessed.

ROC performance of combination of markers: After modeling TB vs. healthy control and other respiratory diseased subjects with individual TKT antibodies, models with combination TKT-antibodies were brought forward. The goal was to assess the classification performance by evaluating the sensitivity, specificity, accuracy, PPV, and NPV. TKT combinations included TKT1+TKT3, TKT1+TKTμ, TKTμ+TKT3, and TKTμ+TKT1+TKT3.

Performance of marker based on decision tree and random forest: Additionally, Decision Tree Classification (DT) was employed for the 7 models, derived from combinations of TKT's, with data excluding and including NTM. The goal was to depict how TB prediction will be altered by inclusion of NTM data sets to the model. The inclusion of NTM and how the model performances differed was crucial to conveying its similarity to TB and the need to be able to accurately predict these two diseases apart. To build these models, a DT was first trained with 75% of the data and then pruned based on misclassification or deviance. The penalty parameter, k, was selected from its corresponding lowest deviance and the size of the tree was also selected in the same fashion. Having pruned the training tree, the model that had a higher accuracy and/or predicted TB and NTM was selected. The performance parameters were based on the test set.

Taking DT classification one step further, Random Forest (RF) methods were applied to combinations of TKT antibodies including just one, two, or all three markers. RF allowed for a more robust approach, where the training set was randomized 500 times, with replacement, with randomly selected predictors, and then averaged out. The number of predictors used is the square root of the number of total predictors in the given model. Models for RF where one of the listed epitopes could be randomly selected for each of the 500 trees were: TKTμ, TKTμ+TKT1, TKTμ+TKT3, and TKTμ+TKT1+TKT3. For example, with all three predictors, for each of the 500 trees generated, one of the three epitopes could have been selected to build each tree from the training set. After performing RF on a training set of 75% of the data, the performance metrics were derived by running the test set.

Results

Serum IgGs against TKT u, TKT1 and TKT3 epitopes differentially discriminate TB from NTM infection. Recently, it was reported that IgG specific antibodies against TKTμ and M.tb specific TKT epitopes (TKT1 and TKT3) have a high specificity and sensitivity to distinguish active TB patients from healthy controls, sarcoidosis and LTBI. NTM infections are caused by non-tuberculous mycobacteria species belonging to same phylogenetic tree as M.tb (van Ingen et al., *J Bacteriol.* 191(18): 5865-5867, 2009). We asked if TKT specific antibodies can differentiate active TB in a mixed population that also comprises NTM samples. 510 samples that comprised of TB (n=148), healthy controls (n=122), sarcoidosis (n=98), lung cancer (LC) (n=30), LTBI (n=50), and NTM (n=62) were tested. The characteristics of the study groups are shown in Table 9.

TABLE 9

| Subjects demographics | | | | | | |
|---|---|---|---|---|---|---|
| Characteristic/Subjects | Control n = 122 | Sarcoidosis n = 98 | LTBI n = 50 | Lung cancer n = 30 | TB n = 148 | NTM n = 62 |
| Age (Mean ± SEM[a]) | 40 ± 8 | 31 ± 12 | 62 ± 12 | 62 ± 11 | 35 ± 12 | 34 ± 12 |
| Sex N(%) | | | | | | |
| Male | 42 (34) | 59 (60) | 24 (48) | 12(40) | 102 (69) | 40 (65) |
| Female | 80 (66) | 39 (40) | 26 (52) | 18 (60) | 46 (31) | 22 (35) |
| Race, N(%) | | | | | | |
| African American | 57 (47) | 91 (93) | 0 (0) | 10 (0) | 9 (6) | 0 (0) |
| African | 0 (0) | 0 (0) | 0 (0) | 0 (0) | 17 (11) | 12(19) |
| Caucasian | 63 (52) | 5 (5) | 0 (0) | 20 (100) | 5 (3) | 0 (0) |
| Asians | 2 (2) | 2 (2) | 50 (100) | 0 (0) | 117 (80) | 50 (81) |
| IRG[c] | N/A | negative | positive | N/A | N/A | N/A |
| TB smear[d] | N/A | N/A | N/A | N/A | 127 | negative |
| TB culture[e] | N/A | N/A | N/A | N/A | 148 | negative |
| MAC culture[f] | N/A | N/A | N/A | N/A | N/A | positive |

Figure 11A:
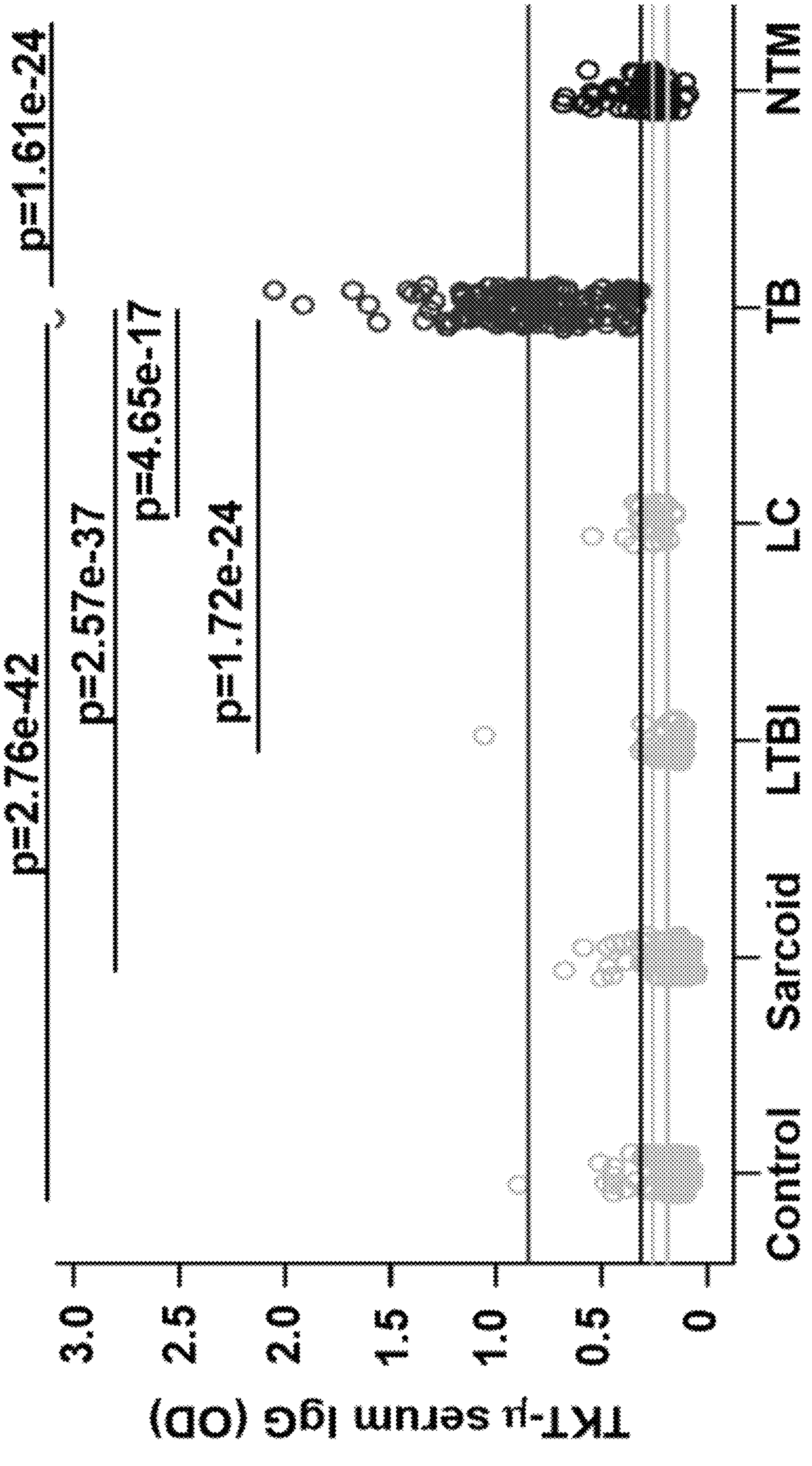
FIGS. 11A-11D: Detection and quantification of TKTμ, TKT1 and TKT3 specific IgGs.
Figure 11B:
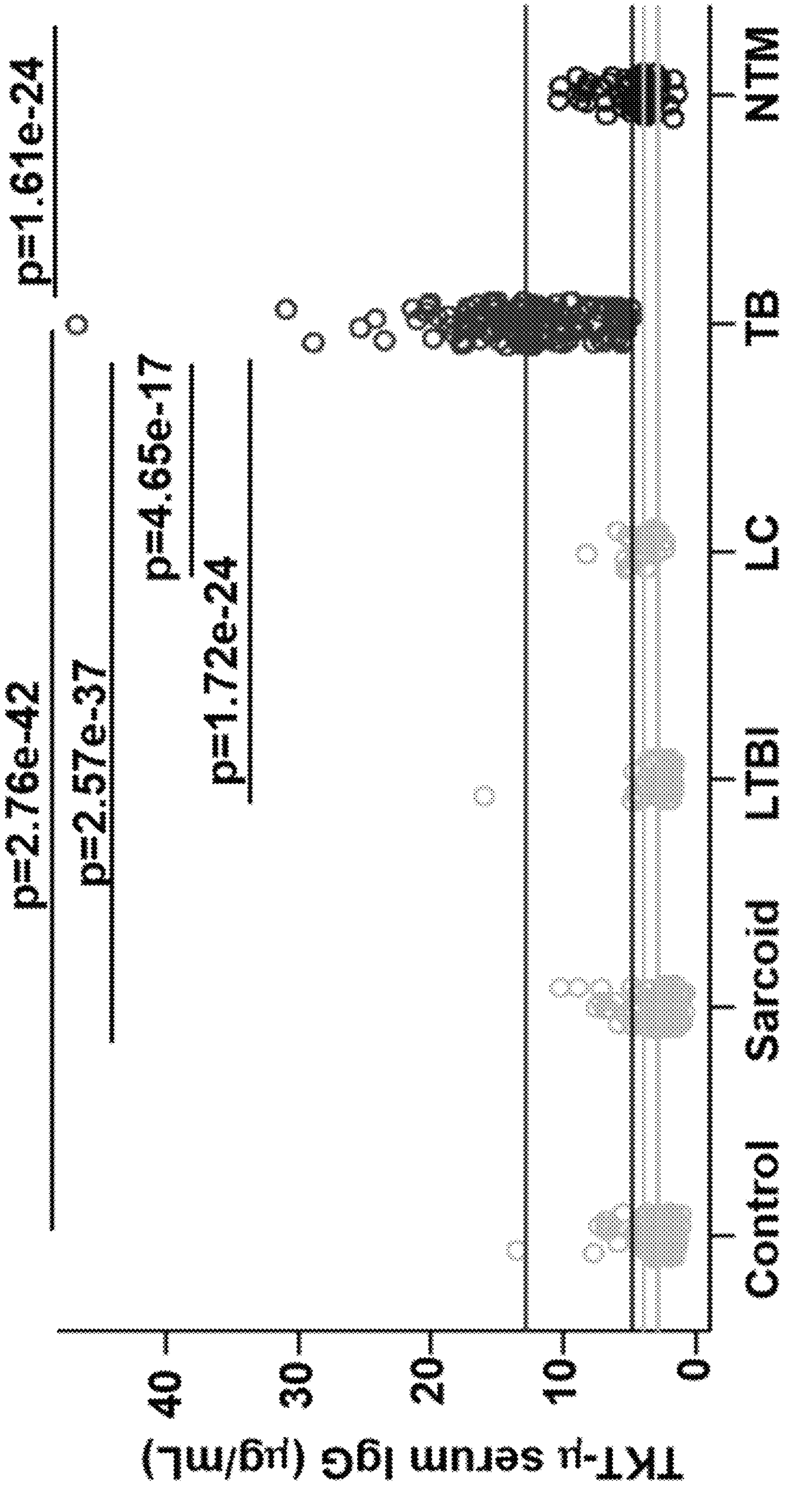
Figure 11C:
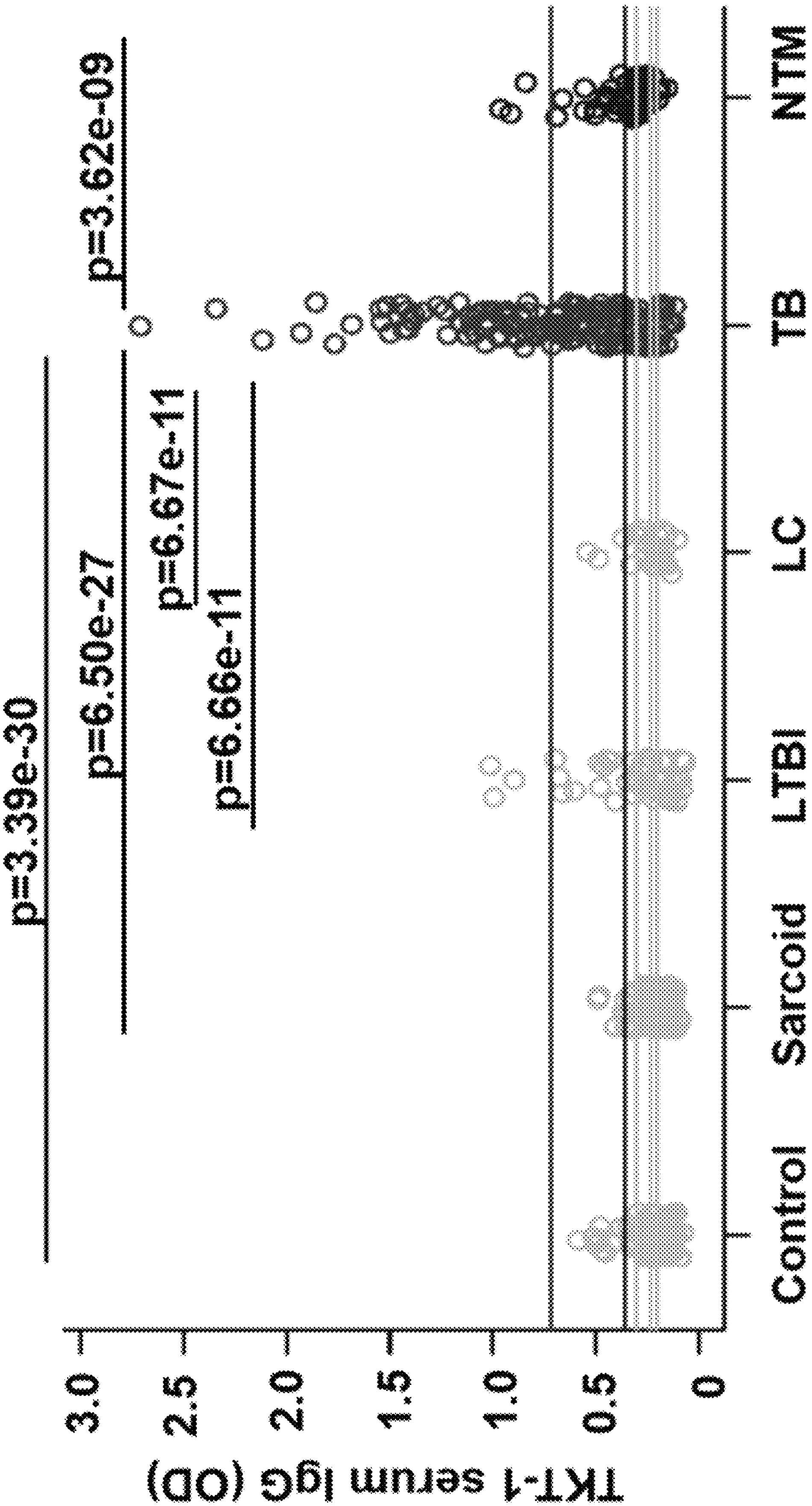
Figure 11D:
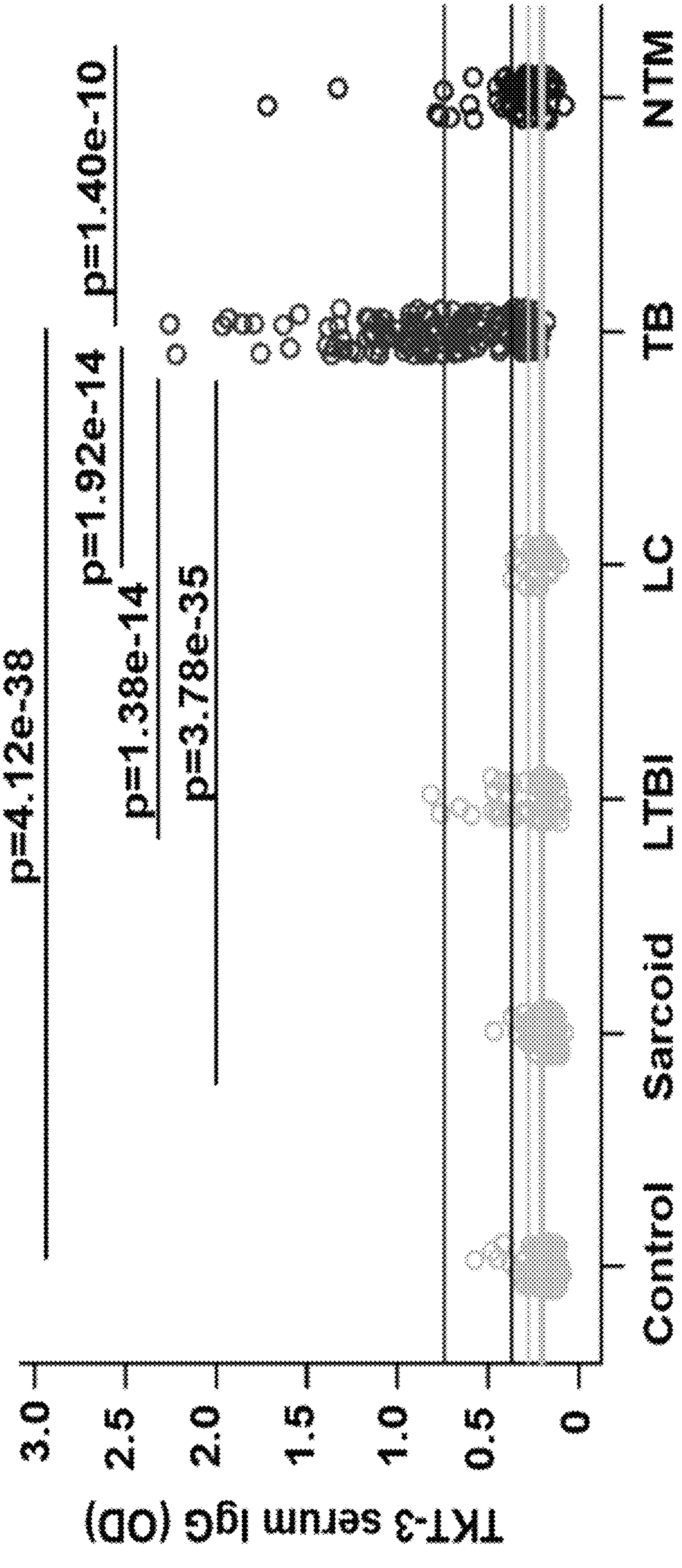

[a]Standard error of mean,
[b]Not applicable,
[c]Interferon γ release assay,
[d]TB Smear (AFB positive sputum),
[e]TB culture (AFB culture positive),
[f]*Mycobacterium avium* complex Previously, a TKT-peptide ELISA was standardized. Utilizing established direct ELISA methods, the reactivity of IgGs to TKT epitopes in the study group was measured (Talreja et al., *Microbiol Spectr.* 11(1): e03377-22, doi: 10.1128/spectrum.03377-22. Epub 2023 Jan. 18). The immunoreactivity to TKTμ epitope is presented as OD (FIG. 11A). As shown, the OD mean value ±standard deviation (SD) in NTM (0.32±0.14) was significantly different (adjusted p value=1.61e-24) compared to OD values of active TB (0.85±0.37). The mean OD values were significantly highest in TB as compared to LC (adjusted p value=4.65e-17), LTBI (adjusted p value=1.72e-24), sarcoidosis (adjusted p value=2.57e-37), and healthy controls (adjusted p value=2.76e-42). The standard curve to determine the actual concentration of specific IgGs against TKTμ epitope as described earlier was used (Talreja et al., *Microbiol Spectr.* 11(1): e03377-22, doi: 10.1128/spectrum.03377-22. Epub 2023 Jan. 18). The mean serum concentration of anti-TKTμ specific IgGs in TB sera, ±SD, was 12.84±5.65 μg/mL, in NTM 4.77±2.07 μg/mL, in healthy controls 2.78±1.65 μg/mL, LTBI 2.93±2.05 μg/mL and in sarcoidosis patients 2.82±1.77 μg/mL (FIG. 11B). Similarly, TKT1 and TKT3 specific IgGs in all study subjects were detected via ELISA. TB patients also exhibited highest mean OD values for M.tb TKT1 (0.72±0.48), which was significantly different compared to OD values of NTM (adjusted p value=3.63e-09), LC (adjusted p value=6.68e-11), LTBI (adjusted p value=6.66e-11), sarcoidosis (adjusted p value=6.50e-27) and healthy controls (adjusted p value=3.39e-30) (FIG. 11C). The OD mean values against M.tb TKT3 in active TB were 0.74±0.45, which was significantly different compared to OD values of NTM (adjusted p value=1.40e-10), LC (adjusted p value=1.93e-14), LTBI (adjusted p value=1.38e-14), sarcoidosis (adjusted p value=3.79e-35) and healthy controls (adjusted p value=4.13e-38) (FIG. 11D). These data indicate that TB patients' sera exhibit significantly higher and specific TKTμ and M.tb TKT1 and TKT3 IgGs compared to NTM and all other groups.

Figure 12A:
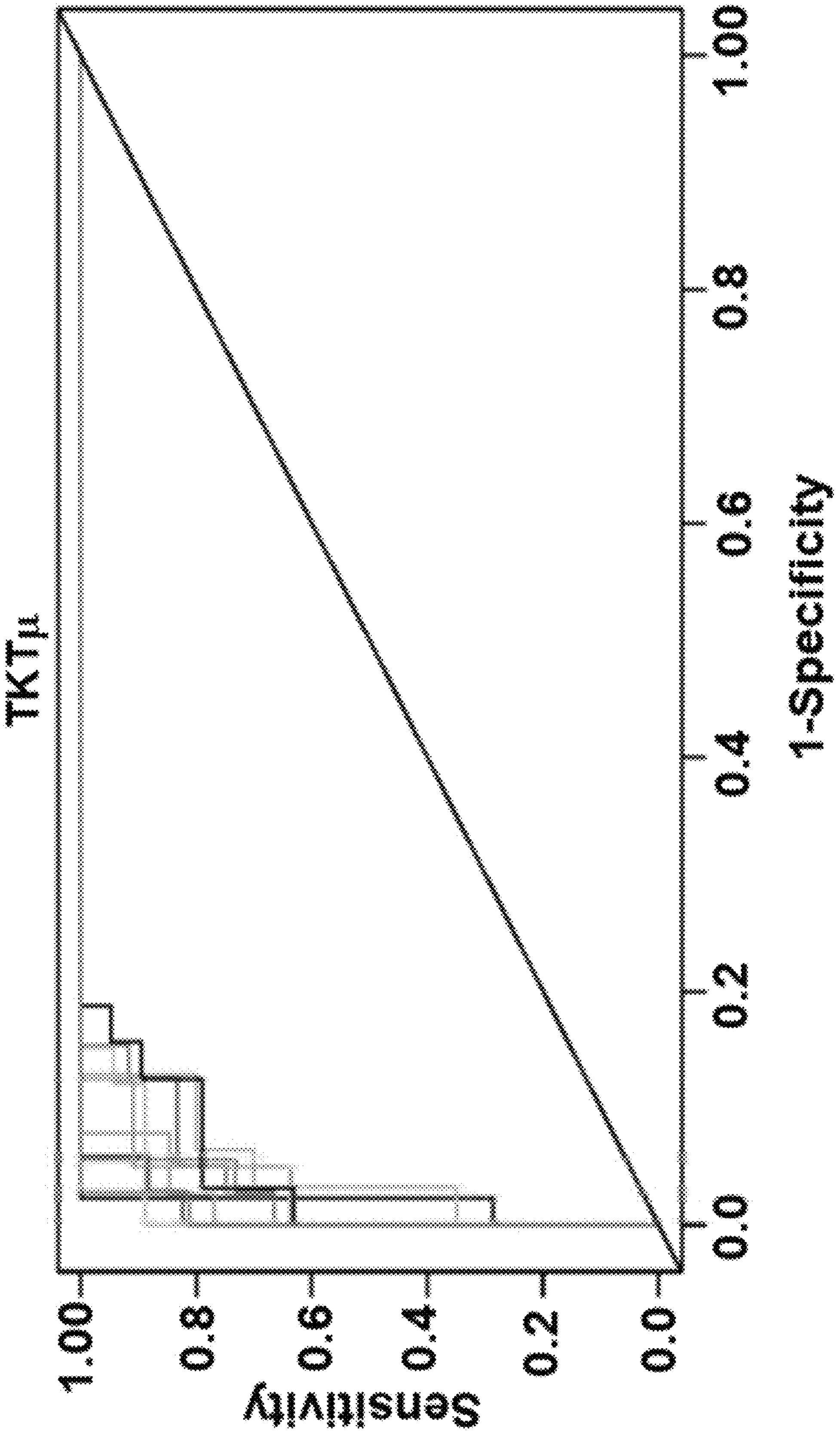
FIGS. 12A-12E: Receiver operating characteristic curve and decision trees of TKTμ.
Figure 12B:
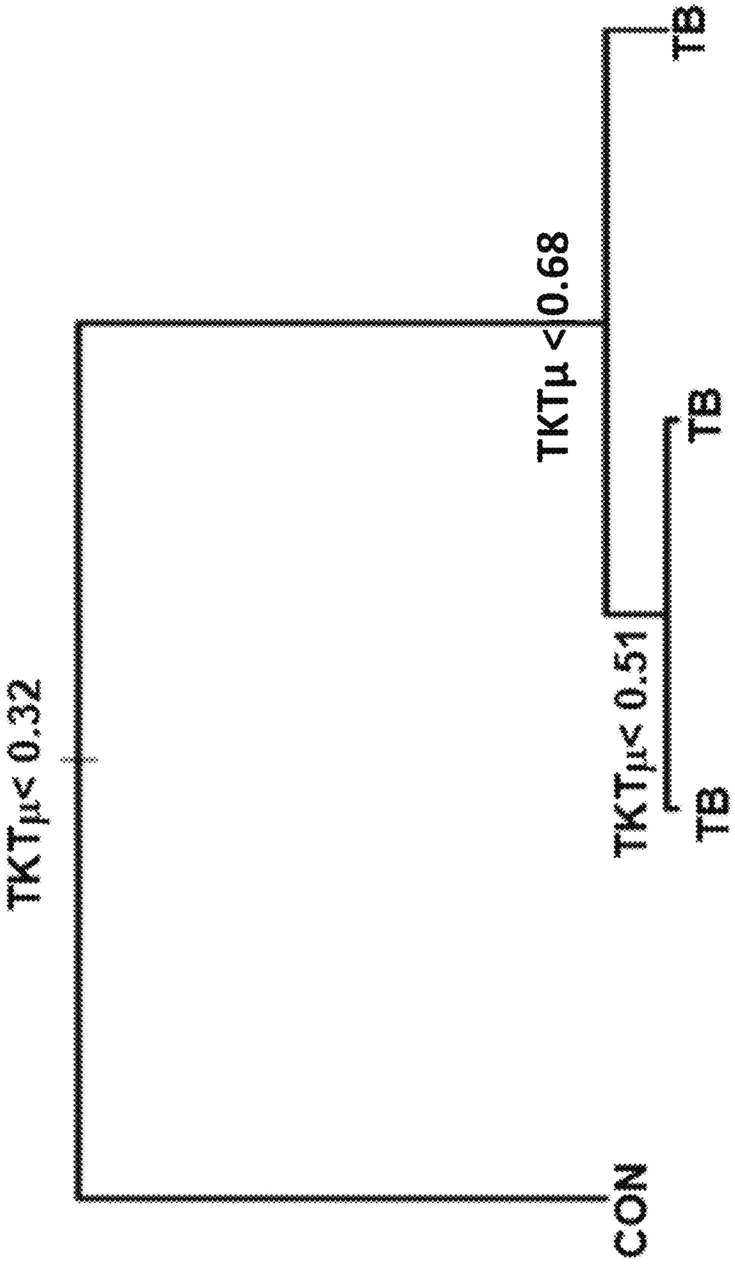
Figure 12C:
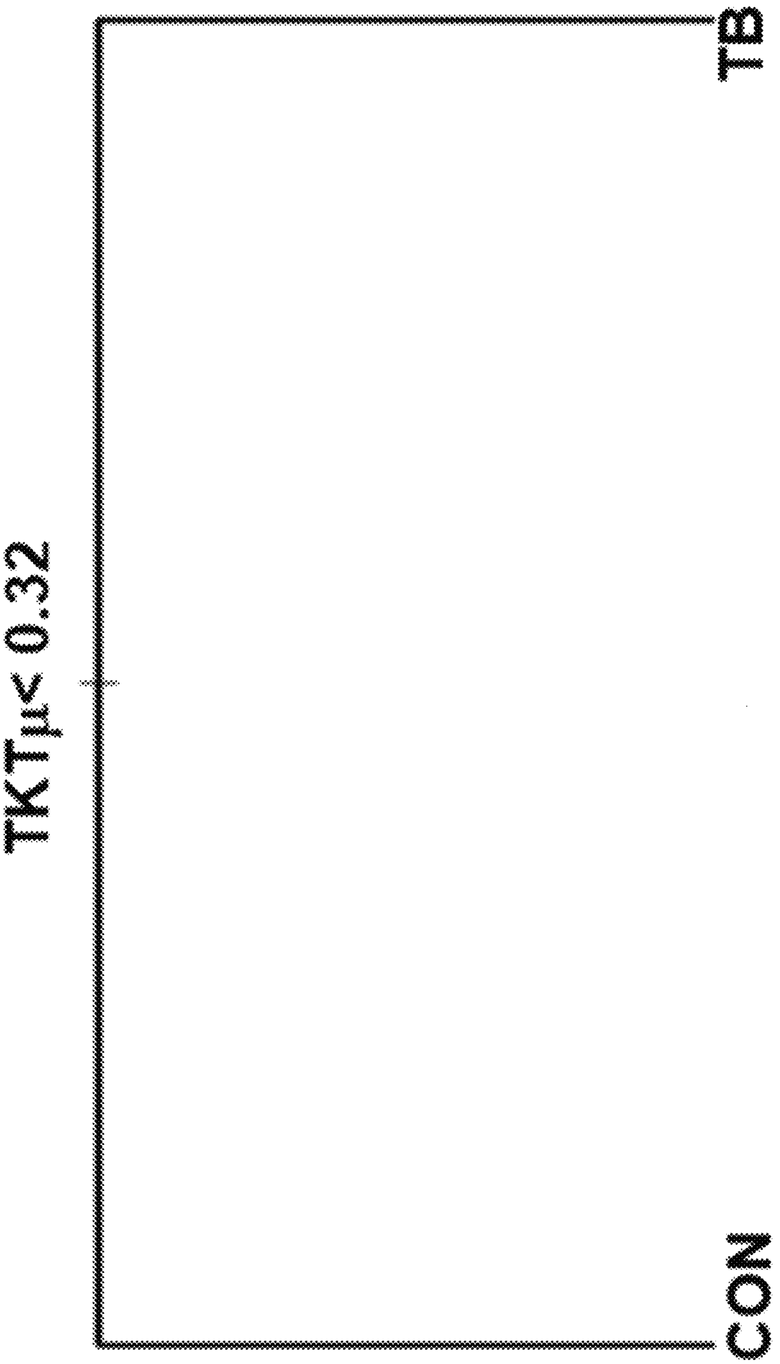
Figure 12D:
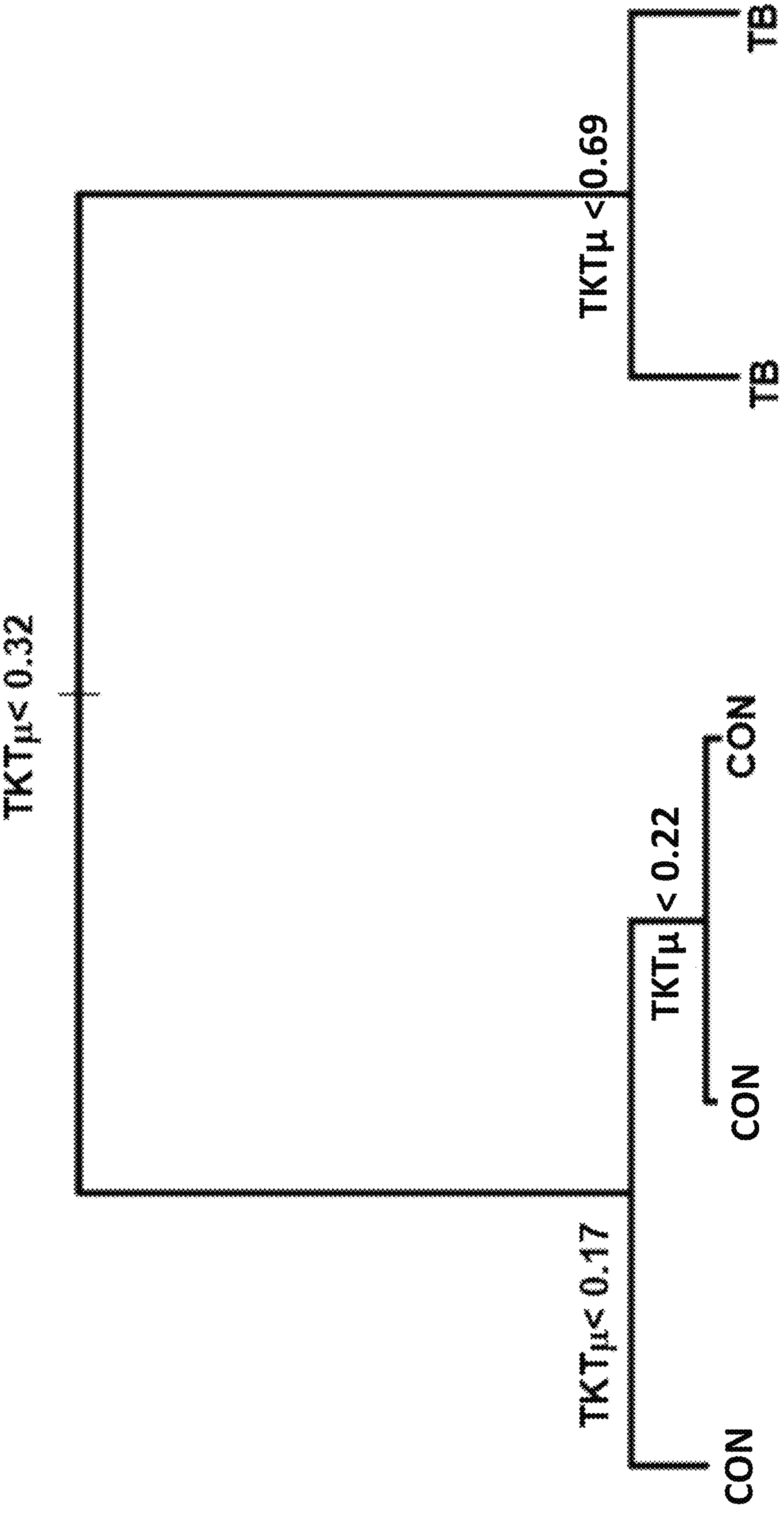
Figure 12E:
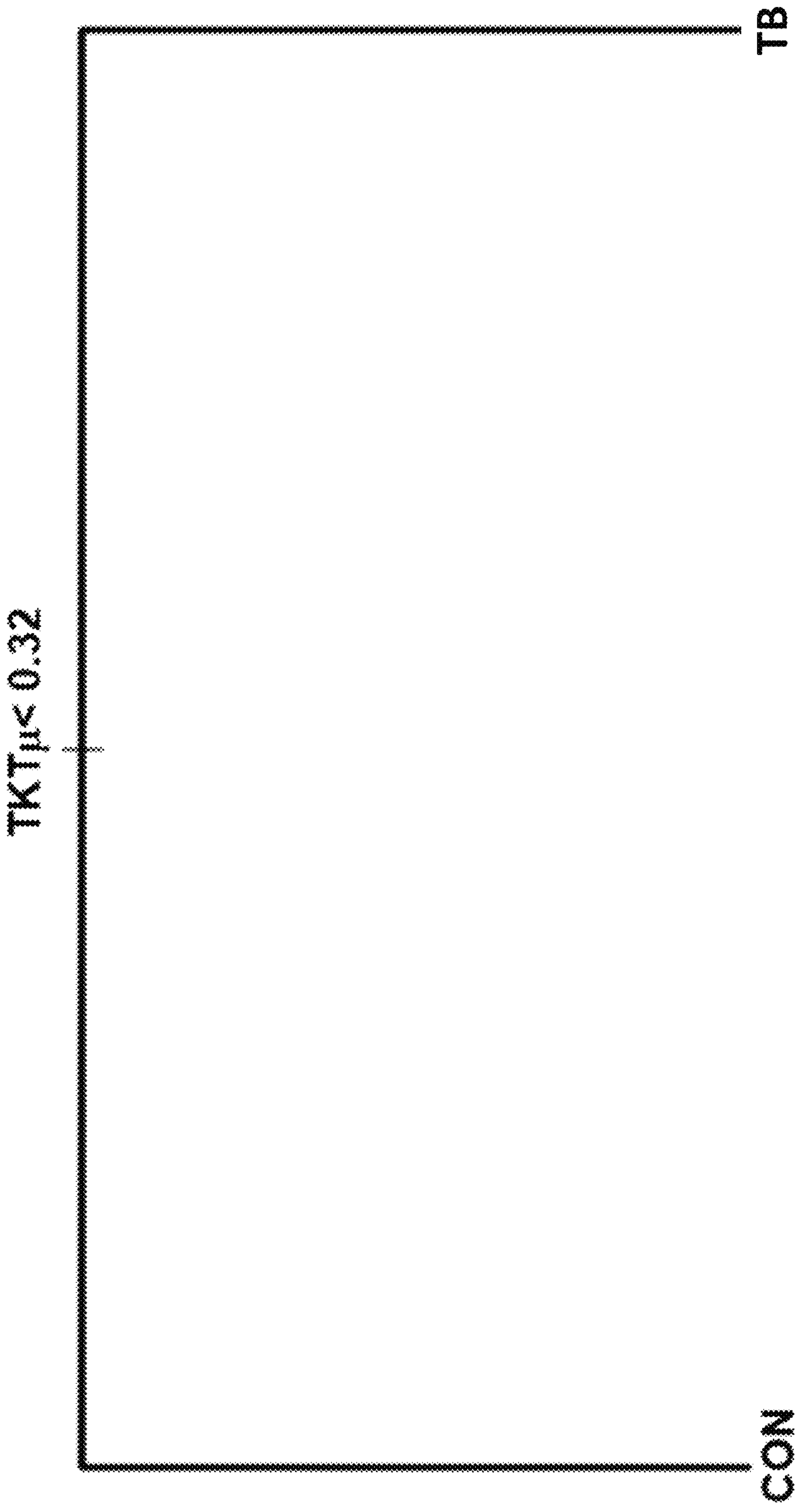

TKTμ antibody-based ROC and decision tree classifications. To develop a model to predict active TB from non-TB subjects by considering NTM and LTBI as non-TB, ROC curves utilizing the values of TKTμ-specific IgG were generated and 10-fold cross validation (CV) was performed on the entire dataset. The TKTμ ROC curve yielded mean±standard error (SE) area under the curve (AUC) of 0.98±0.00 (FIG. 12A). The 10-fold CV with TKTμ yielded a mean sensitivity of 0.99±0.01, specificity of 0.88±0.02, accuracy of 0.91±0.01, NPV of 0.99±0.00 and PPV of 0.76±0.04 (Table 10).

TABLE 10

| TB v | 10-Fold Cross Validation Performance Parameters (Mean ± SEM[a]) | | | | | |
|---|---|---|---|---|---|---|
| Non-TB | AUC | Sensitivity | Specificity | PPV | NPV | Accuracy |
| TKTμ | **0.979 ± 0.004** | 0.988 ± 0.008 | 0.879 ± 0.018 | 0.763 ± 0.039 | 0.993 ± 0.004 | 0.910 ± 0.014 |
| TKT1 | 0.864 ± 0.021 | 0.834 ± 0.038 | 0.754 ± 0.026 | 0.576 ± 0.043 | 0.919 ± 0.021 | 0.775 ± 0.019 |
| TKT3 | 0.918 ± 0.011 | 0.891 ± 0.018 | 0.757 ± 0.028 | 0.599 ± 0.053 | 0.945 ± 0.010 | 0.792 ± 0.024 |
| TKTμ + TKT1 | 0.978 ± 0.004 | 0.988 ± 0.008 | **0.881 ± 0.018** | **0.767 ± 0.039** | 0.993 ± 0.004 | **0.912 ± 0.013** |

TABLE 10-continued

| TB v Non-TB | 10-Fold Cross Validation Performance Parameters (Mean ± SEM[a]) AUC | Sensitivity | Specificity | PPV | NPV | Accuracy |
|---|---|---|---|---|---|---|
| TKTμ + TKT3 | 0.978 ± 0.003 | **0.993 ± 0.007** | 0.873 ± 0.014 | 0.752 ± 0.032 | **0.997 ± 0.003** | 0.908 ± 0.009 |
| TKT1 + TKT3 | 0.921 ± 0.013 | 0.848 ± 0.033 | 0.794 ± 0.024 | 0.622 ± 0.052 | 0.926 ± 0.020 | 0.806 ± 0.023 |
| TKTμ + TKT1 + TKT3 | 0.977 ± 0.004 | 0.981 ± 0.014 | 0.873 ± 0.015 | 0.751 ± 0.033 | 0.991 ± 0.006 | 0.904 ± 0.011 |

[a]Standard error of mean,
bold fill indicates largest performance parameter

Decision Tree (DT) based classification was performed for the TKTμ data, first by excluding NTM and second by including NTM samples, to determine the performance of peptide-specific IgG, the impact of inclusion of NTM and to select the TB group from the non-TB group. FIGS. 2B & 2C depict DTs for TKTμ while excluding NTM data. The DT for TKTμ based on misclassification or deviance. The DT with NTM group yielded a precision value of 0.82 for active TB and 0.89 for non-TB groups. The TKTμ DT model achieved TB diagnostic performance of a sensitivity of 1.0, specificity of 0.88, accuracy of 0.92, NPV of 1.0 and PPV of 0.82 (FIG. 2E and Table 11).

TABLE 11

| TB v Non-TB v (NTM) | With NTM | Decision Tree Classification TB Performance Parameters[a] Sensitivity | Specificity | PPV | NPV | Accuracy |
|---|---|---|---|---|---|---|
| TKTμ | No | **1** | 0.886 | 0.840 | **1** | 0.929 |
| | | **(1, 1)** | (0.811, 0.960) | (0.738, 0.942) | **(1, 1)** | (0.881, 0.977) |
| | Yes | *1* | 0.880 | 0.815 | *1* | 0.921 |
| | | *(1, 1)* | (0.809, 0.950) | (0.711, 0.918) | *(1, 1)* | (0.874, 0.968) |
| TKT1 | No | 0.548 | **0.957** | 0.885 | 0.779 | 0.804 |
| | | (0.397, 0.698) | **(0.910, 1)** | (0.762, 1) | (0.691, 0.867) | (0.730, 0.877) |
| | Yes | 0.545 | 0.964 | 0.889 | 0.800 | 0.819 |
| | | (0.398, 0.693) | (0.924, 1) | (0.770, 1) | (0.722, 0.878) | (0.752, 0.886) |
| TKT3 | No | 0.881 | 0.814 | 0.740 | 0.919 | 0.839 |
| | | (0.783, 0.979) | (0.723, 0.906) | (0.618, 0.862) | (0.852, 0.987) | (0.771, 0.907) |
| | Yes | 0.545 | *0.988* | *0.960* | 0.804 | 0.835 |
| | | (0.398, 0.693) | *(0.964, 1)* | *(0.883, 1)* | (0.727, 0.881) | (0.770, 0.899) |
| TKTμ + TKT1 | No | **1** | 0.886 | 0.840 | **1** | 0.929 |
| | | **(1, 1)** | (0.811, 0.960) | (0.738, 0.942) | **(1, 1)** | (0.881, 0.977) |
| | Yes | *1* | 0.880 | 0.815 | *1* | 0.921 |
| | | *(1, 1)* | (0.809, 0.950) | (0.711, 0.918) | *(1, 1)* | (0.874, 0.968) |
| TKTμ + TKT3 | No | 0.976 | 0.943 | **0.911** | 0.985 | **0.955** |
| | | (0.930, 1) | (0.888, 0.997) | **(0.828, 0.994)** | (0.956, 1) | **(0.917, 0.993)** |
| | Yes | *1* | 0.916 | 0.863 | *1* | *0.945* |
| | | *(1, 1)* | (0.856, 0.975) | (0.768, 0.957) | *(1, 1)* | *(0.905, 0.985)* |
| TKT1 + TKT3 | No | 0.833 | 0.900 | 0.833 | 0.900 | 0.875 |
| | | (0.721, 0.946) | (0.830, 0.970) | (0.721, 0.946) | (0.830, 0.970) | (0.814, 0.936) |
| | Yes | 0.545 | *0.988* | *0.960* | 0.804 | 0.835 |
| | | (0.398, 0.693) | *(0.964, 1)* | *(0.883, 1)* | (0.727, 0.881) | (0.770, 0.899) |
| TKTμ + TKT1 + TKT3 | No | 0.976 | 0.943 | **0.911** | 0.985 | **0.955** |
| | | (0.930, 1) | (0.888, 0.997) | **(0.828, 0.994)** | (0.956, 1) | **(0.917, 0.993)** |
| | Yes | 0.977 | 0.928 | 0.878 | 0.987 | *0.945* |
| | | (0.933, 1) | (0.872, 0.983) | (0.786, 0.969) | (0.962, 1) | *(0.905, 0.985)* |

Bold indicates the best parameter of "With NTM" = No,
Italics indicates the best parameter of "With NTM" = Yes
[a]Parameter & Confidence Interval: 95%, assumed normal, parameter ± 1.96*SE, SE is standard error of proportion was first trained with 75% of the data (FIG. 2B) and then pruning of DT (FIG. 2C) was performed for TKTμ based on misclassification or deviance. The best model that had a higher accuracy to predict TB and NTM was selected. DT without NTM group yielded a precision value (PPV) of 0.84 for TB and 1.0 for non-TB groups. This model yielded a sensitivity of 1.0, specificity of 0.89, and accuracy of 0.93, and a NPV of 1.0 (Table 11). Next, the NTM data set was included to assess the stability of the diagnostic accuracy of TB based on TKTμ specific IgG antibodies by performing DTs algorithm (FIGS. 2D & 2E). The DT was first trained with 75% of the data (FIG. 2D) and then pruned (FIG. 2E)

Figure 13A:
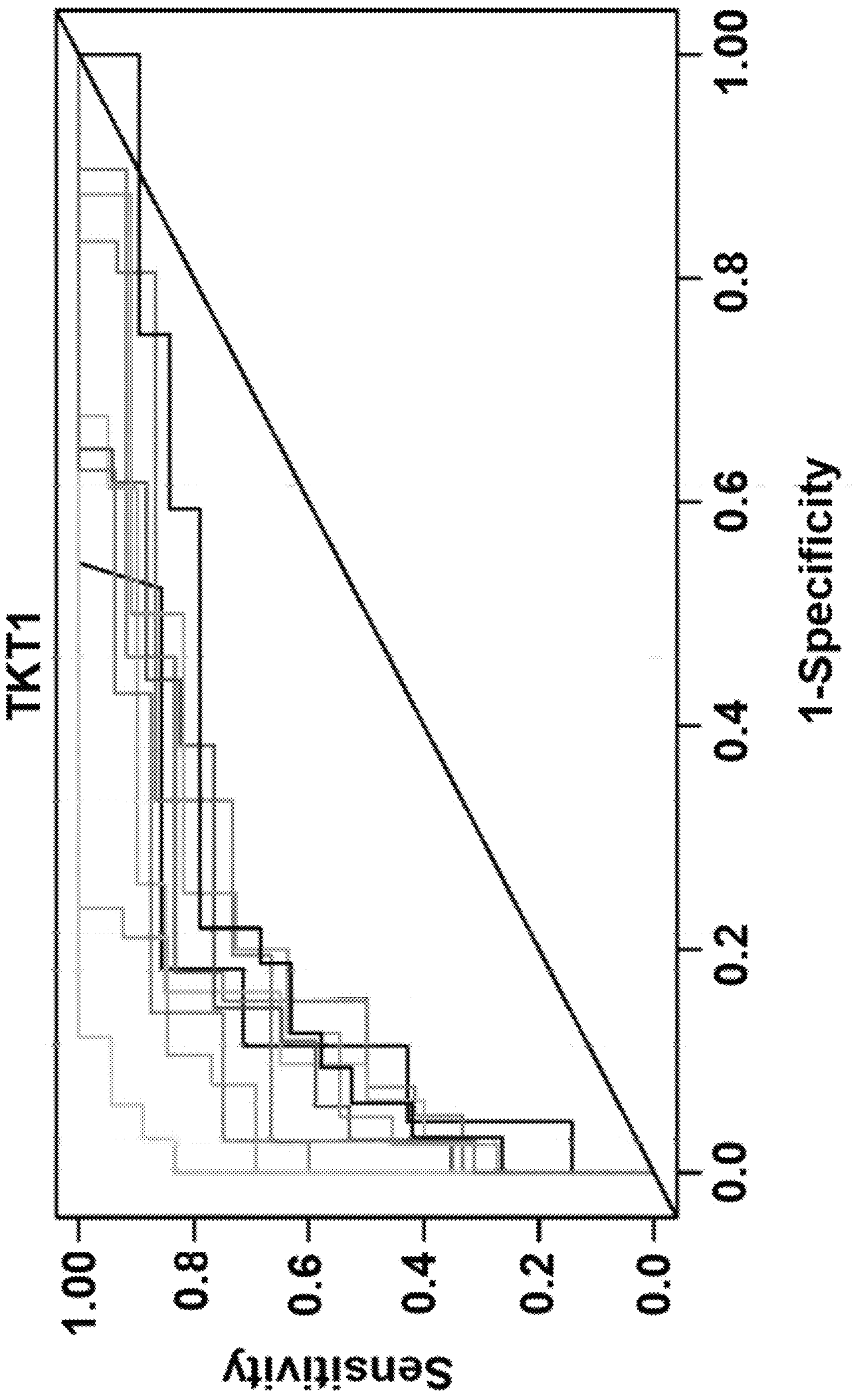
FIGS. 13A-13E: Receiver operating characteristic curve and decision trees of TKT1.
Figure 13B:
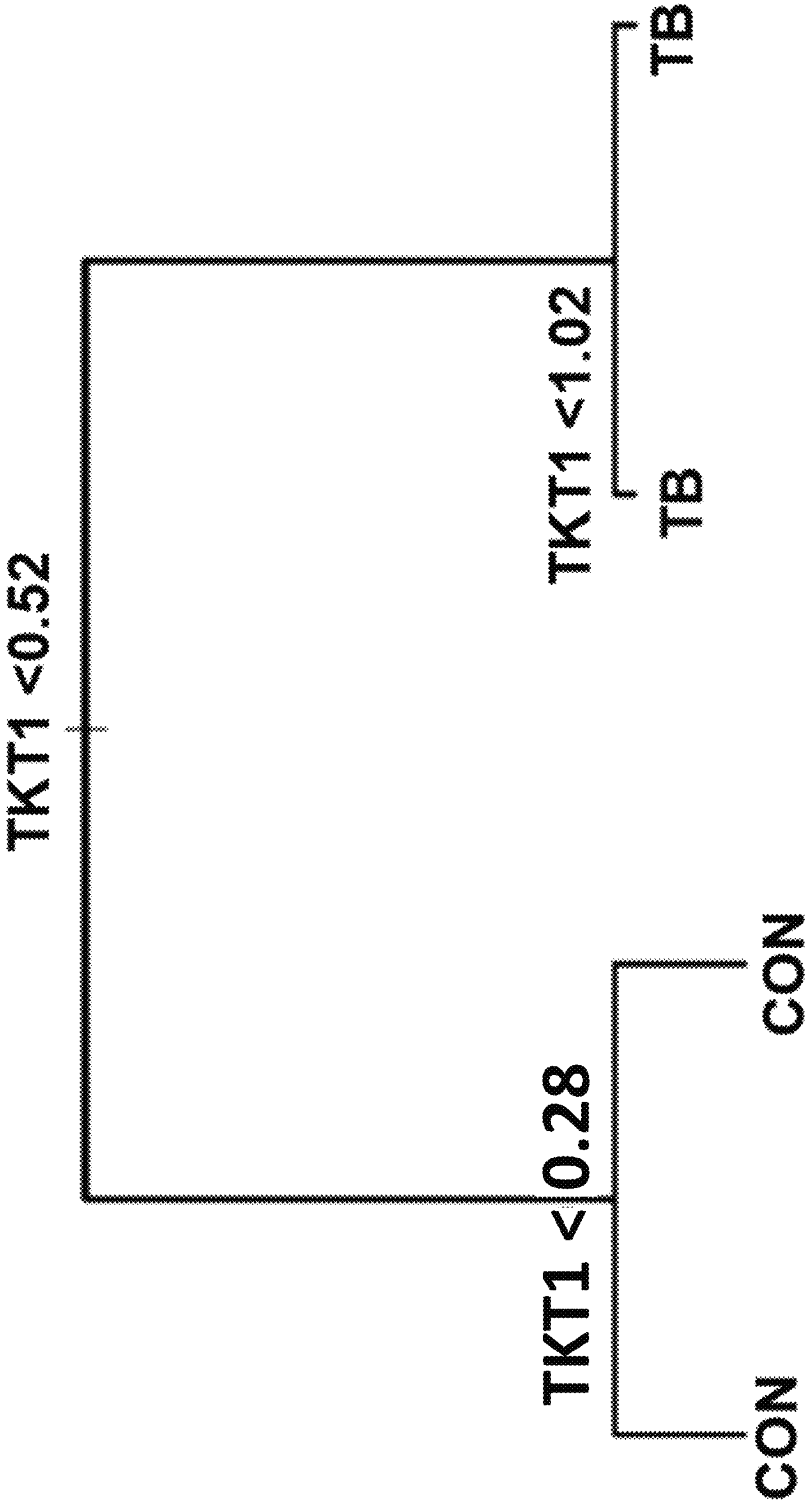
Figure 13C:
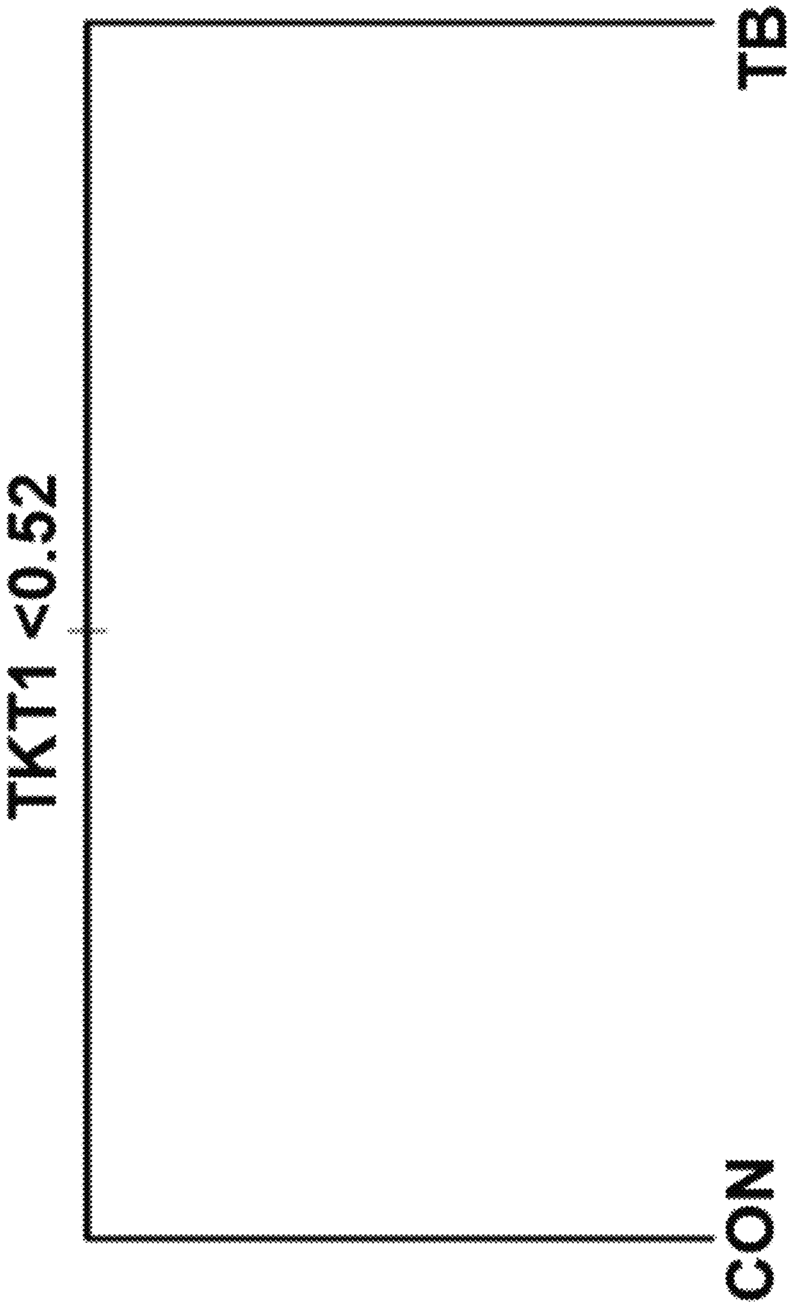
Figure 13D:
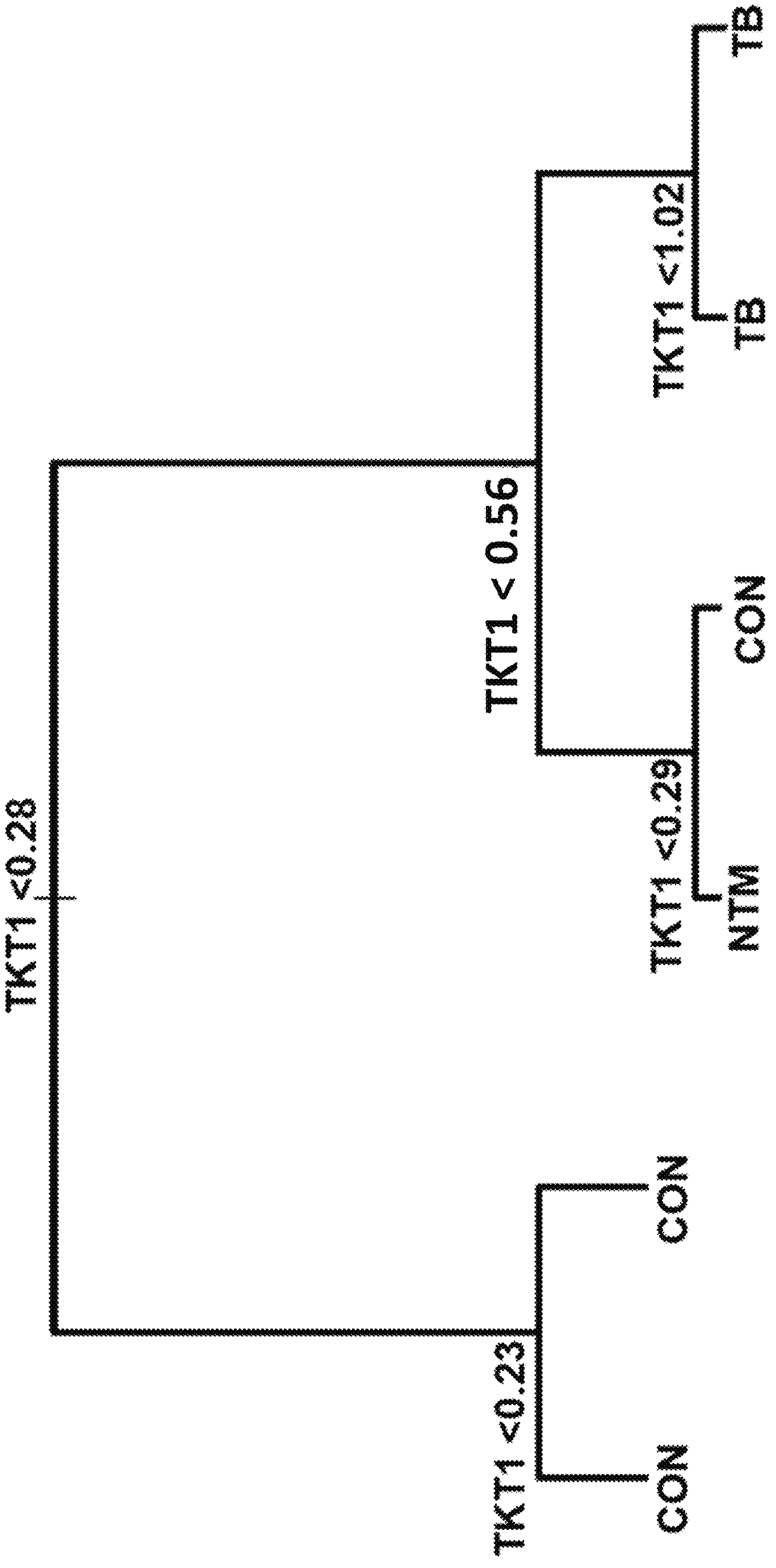
Figure 13E:
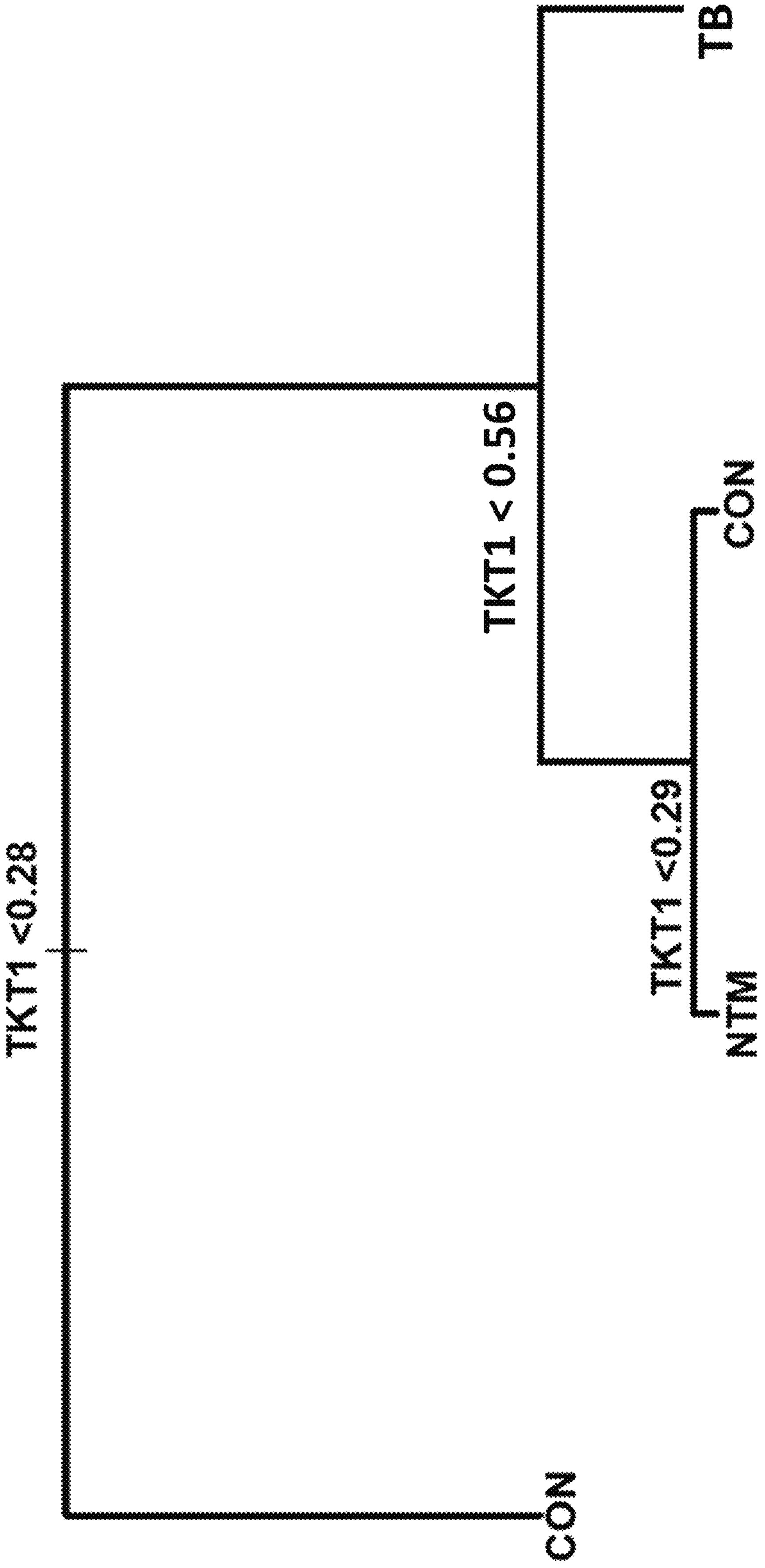

TKT1 antibody-based ROC curve and decision tree classifications. ROC curves utilizing the OD values of TKT1-specific IgG were generated and 10-fold cross validation (CV) was performed on the entire dataset. The TKT1 ROC curve yielded a mean±SE area under the curve (AUC) of 0.86±0.02 (FIG. 13A). The 10-fold CV with TKT1 yielded a mean sensitivity of 0.83±0.04, specificity of 0.75±0.03, accuracy of 0.78±0.02, NPV of 0.92±0.02 and PPV of 0.58±0.04 (Table 10). The DT modeling was performed for TKT1 antibody while excluding and including NTM data set. FIGS. 13B, 13C and Table 11 depict the DTs for ODs of TKT1 epitope while excluding NTM. The DT was first trained with 75% of the data (FIG. 13B) and then pruning of DT (FIG. 13C) was performed for TKT1 based on misclassification or deviance. The best model that had the highest accuracy to predict TB and NTM was selected. DT without NTM group yielded the precision value of 0.89 for TB and 0.78 for non-TB group. DTs for TKT1 antibody while including NTM data were then computed (FIGS. 13D & 13E). The DT was first trained with 75% of the data (FIG. 13D) and pruned (FIG. 13E) for TKT1 based on misclassification or deviance. DT while including NTM group yielded the precision value of 0.89 for active TB, 0.70 for non-TB group and 0.0 for NTM with a sensitivity of 0.55, specificity of 0.96, accuracy of 0.82, and NPV of 0.80 (FIG. 13E). These results indicate that while TKT1 is a valuable marker to distinguish active TB from other groups, including NTM, it has lack of value to differentiate NTM from others.

Figure 14A:
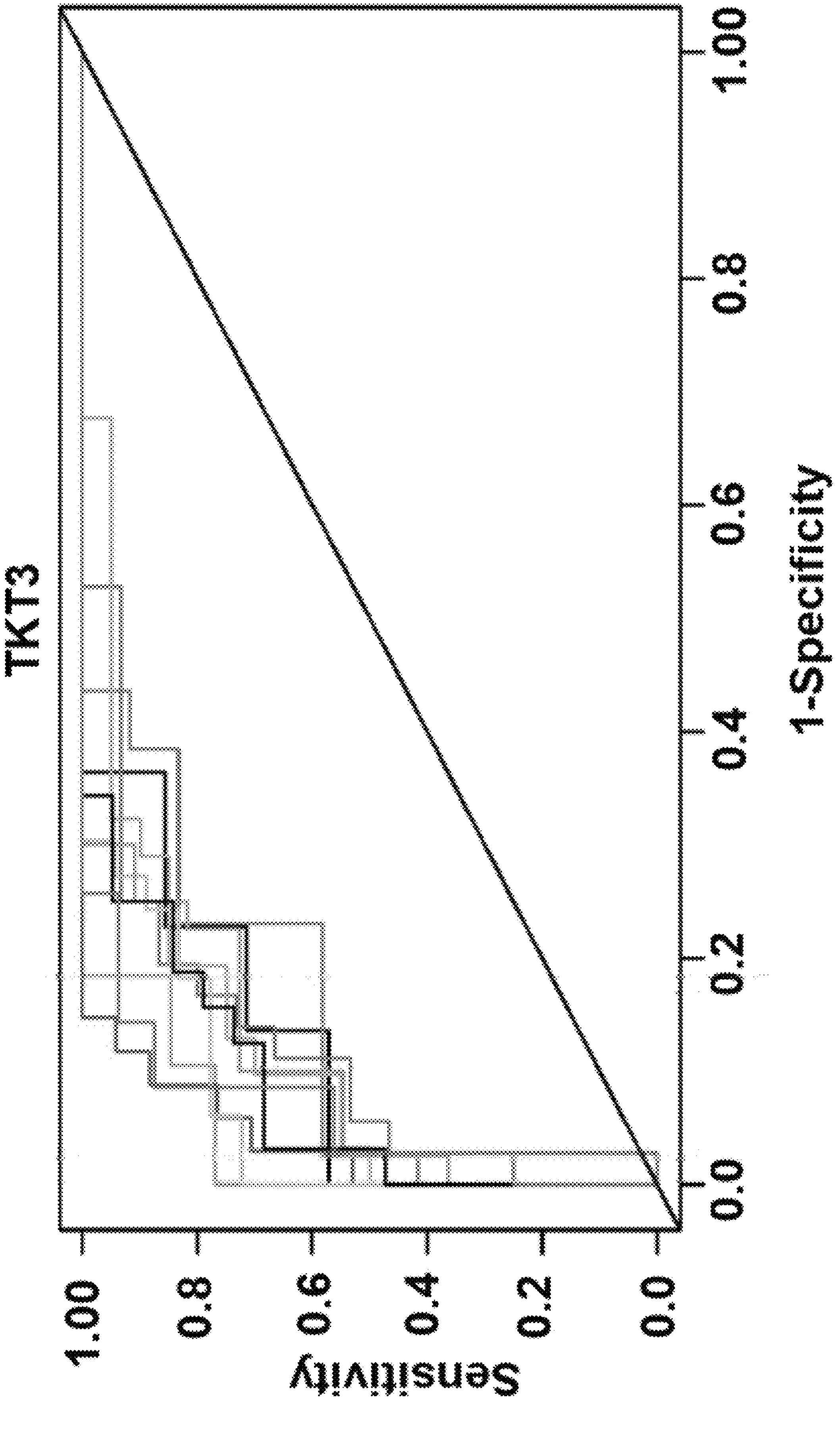
FIGS. 14A-14E: Receiver operating characteristic curve and decision trees of TKT3.
Figure 14B:
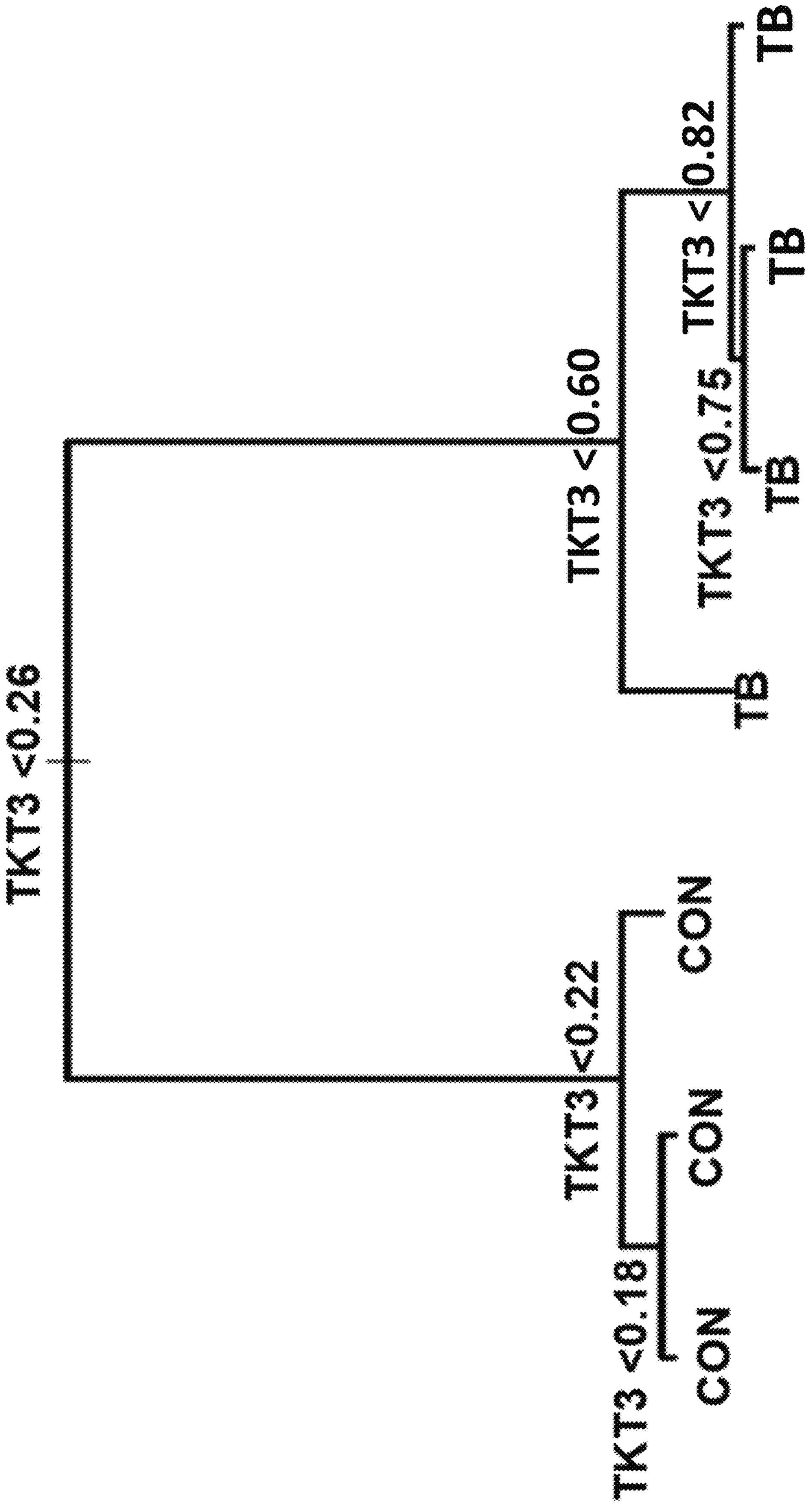
Figure 14C:
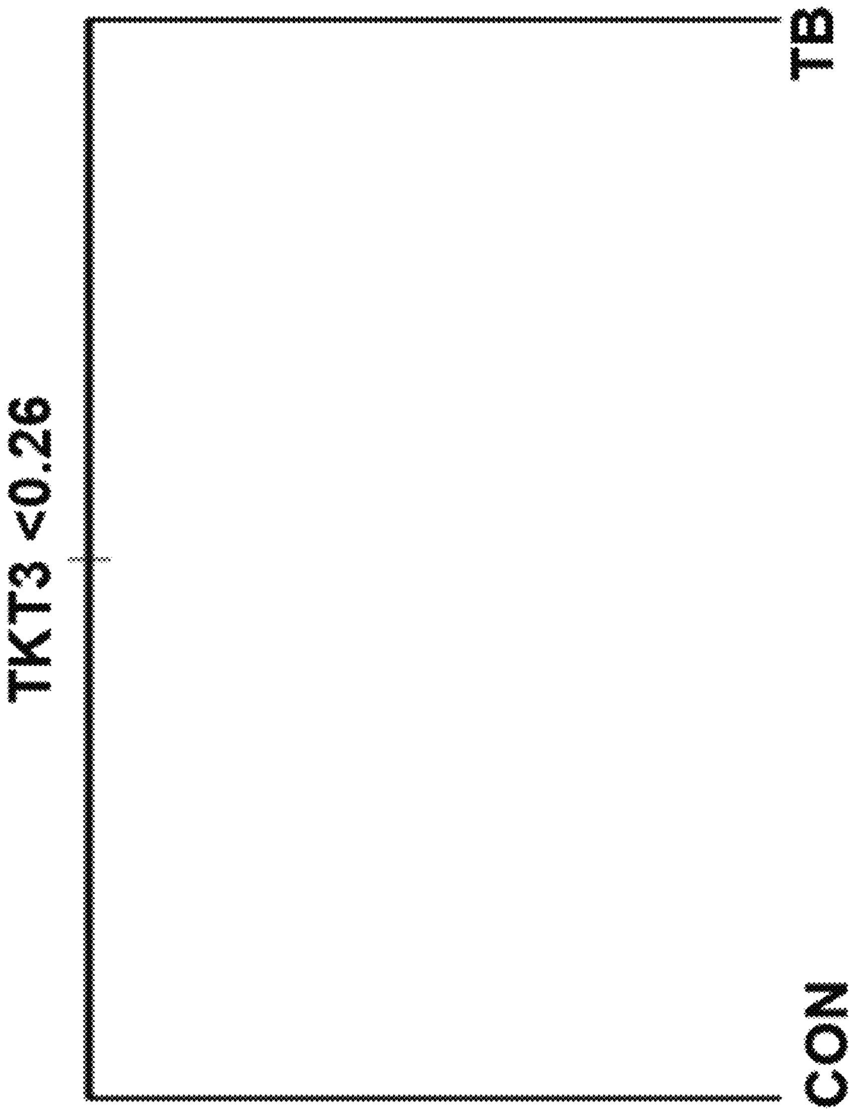
Figure 14D:
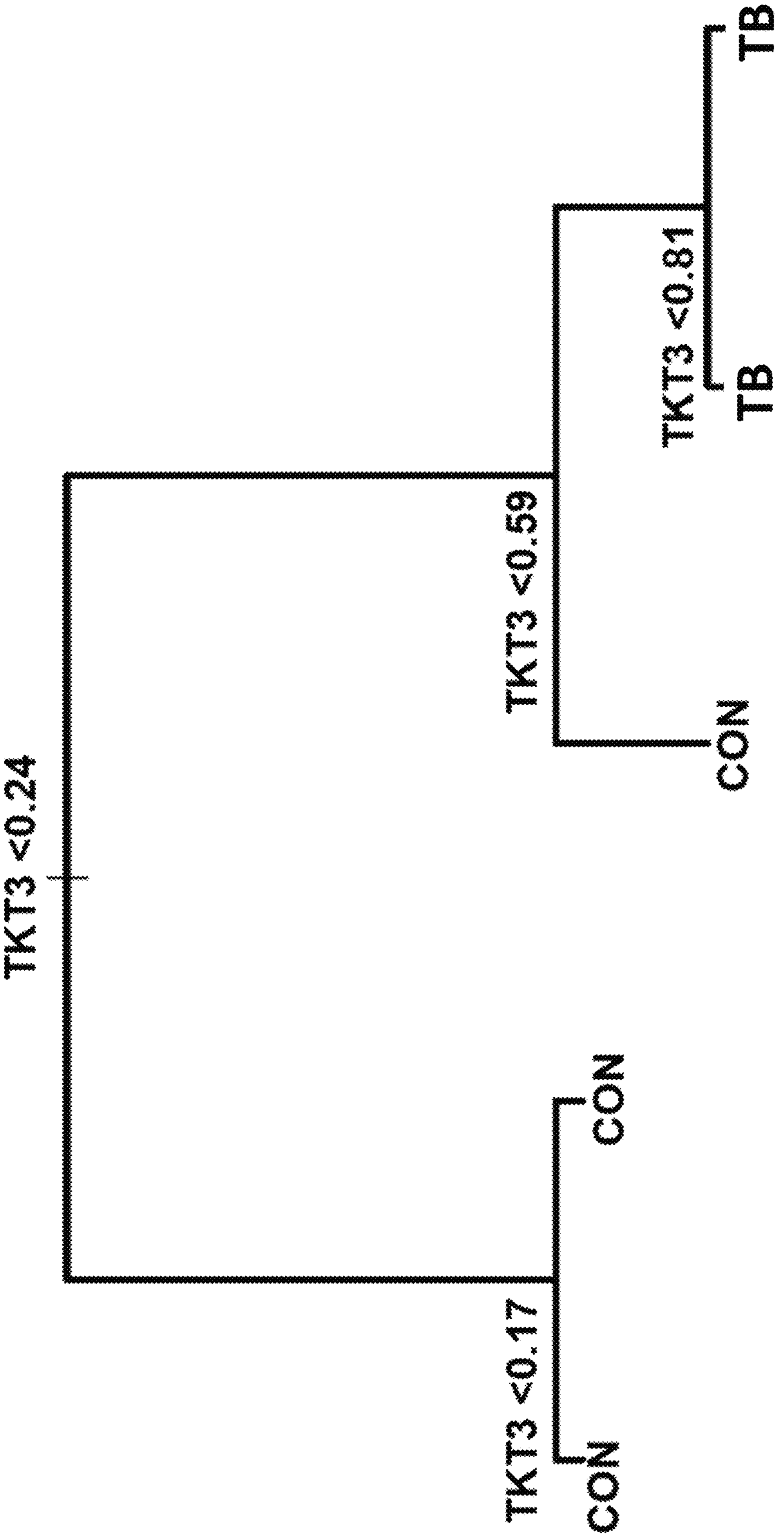
Figure 14E:
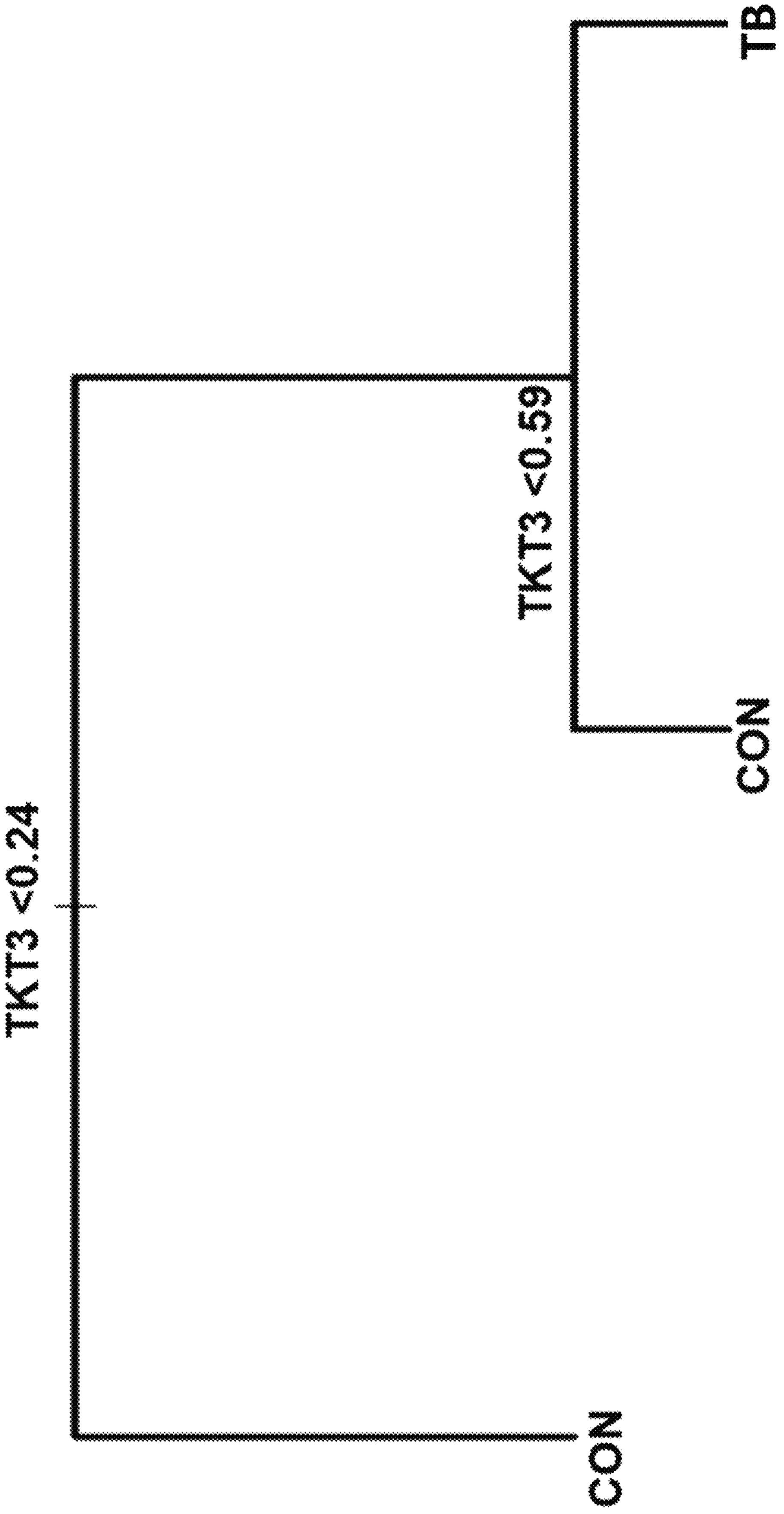

TKT3 antibody-based ROC curve and decision tree classifications. ROC curves utilizing the OD values of TKT3-specific IgGs were generated and 10-fold cross validation (CV) was performed on the entire dataset. The TKT3 ROC curve yielded a mean±SE area under the curve (AUC) of 0.92±0.01 (FIG. 14A). The 10-fold CV with TKT3 yielded a mean sensitivity of 0.89±0.02, specificity of 0.76±0.03, accuracy of 0.79±0.02, NPV of 0.95±0.01 and PPV of 0.60±0.05 (FIG. 14A and Table 10). DT classification was performed for TKT3, with data excluding and including NTM, to determine the performance of the peptide to select the TB group from the non-TB groups. FIG. 14B shows the trained DT for TKT3 data while excluding NTM group. Pruned DT for TKT3 based on misclassification or deviance is shown in FIG. 14C. DT without NTM group yielded the precision value of 0.74 for TB and 0.92 for non-TB groups with a sensitivity of 0.88, specificity of 0.81, accuracy of 0.84, and NPV of 0.92 (FIG. 14C and Table 11). FIG. 14D depicts the trained DT for TKT3 results while including NTM data in the model. Pruned DT for TKT3 based on misclassification or deviance is shown in FIG. 14E. DT with NTM group yielded a precision value of 0.96 for active TB and 0.72 for non-TB group and achieved a sensitivity of 0.55, specificity of 0.99, accuracy of 0.84, and NPV of 0.80 (FIG. 14E and Table 11).

Figure 15A:
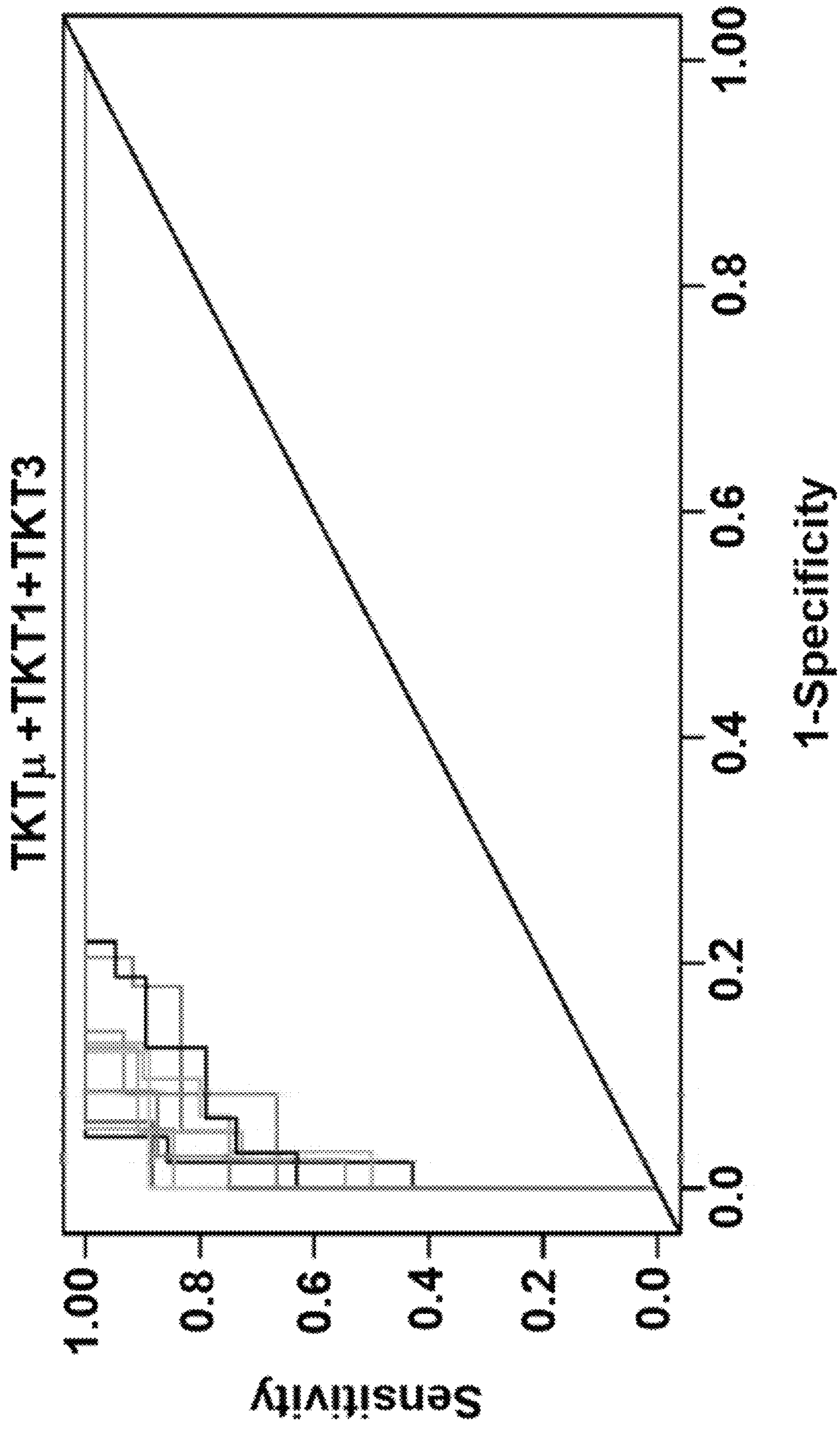
FIGS. 15A-15E: Receiver operating characteristic curve and decision trees of combined markers TKTμ+TKT1+TKT3.
Figure 15B:
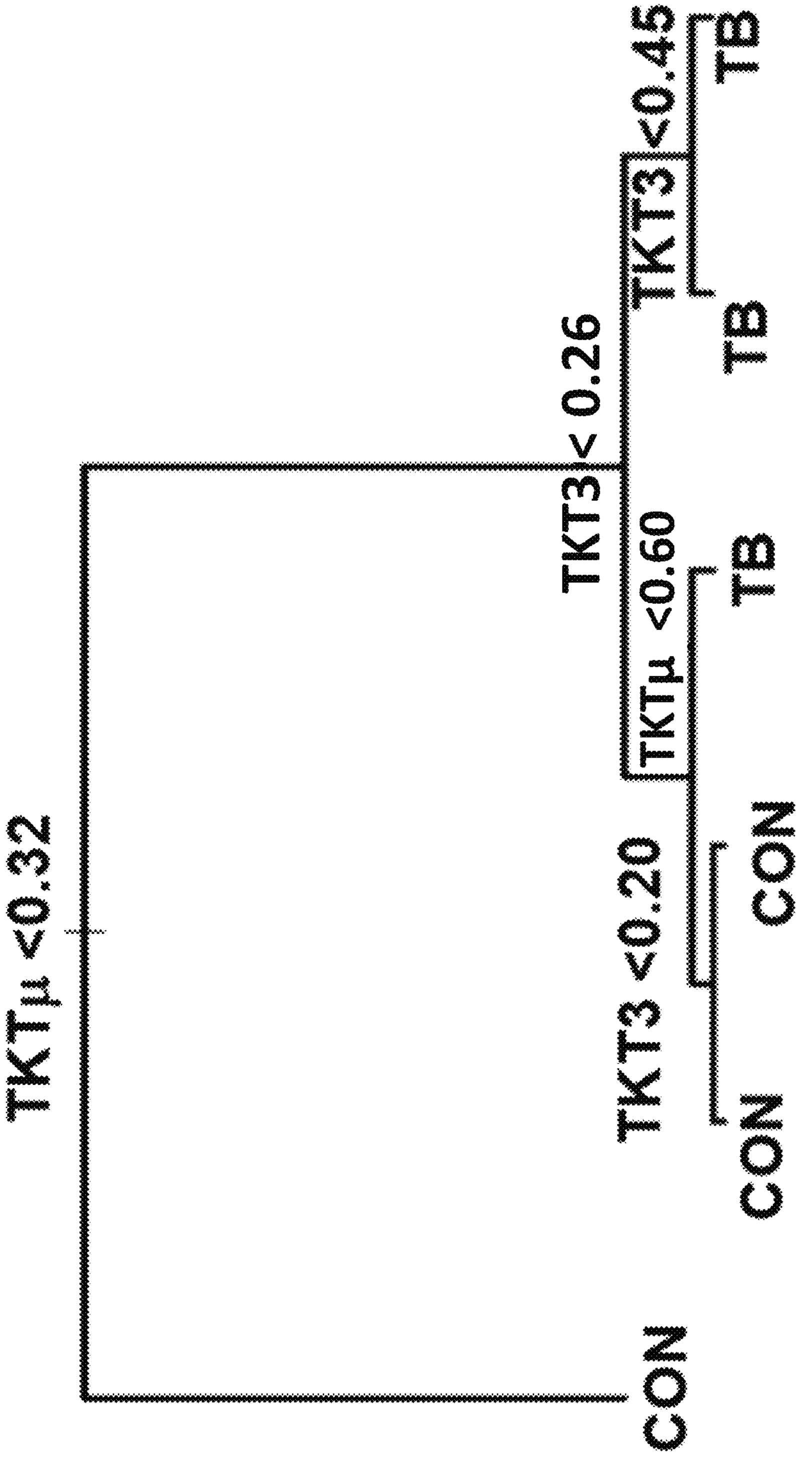
Figure 15C:
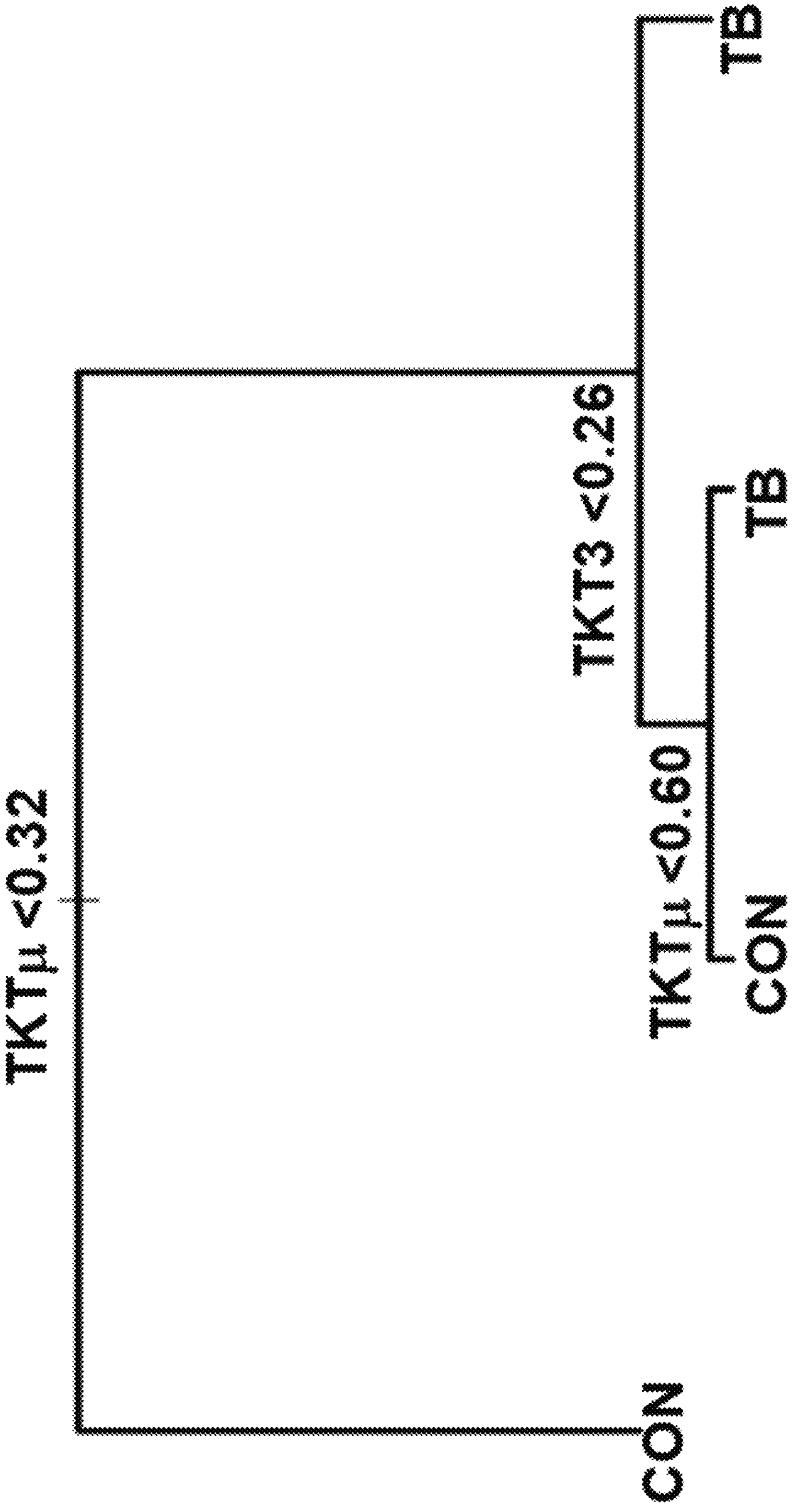
Figure 15D:
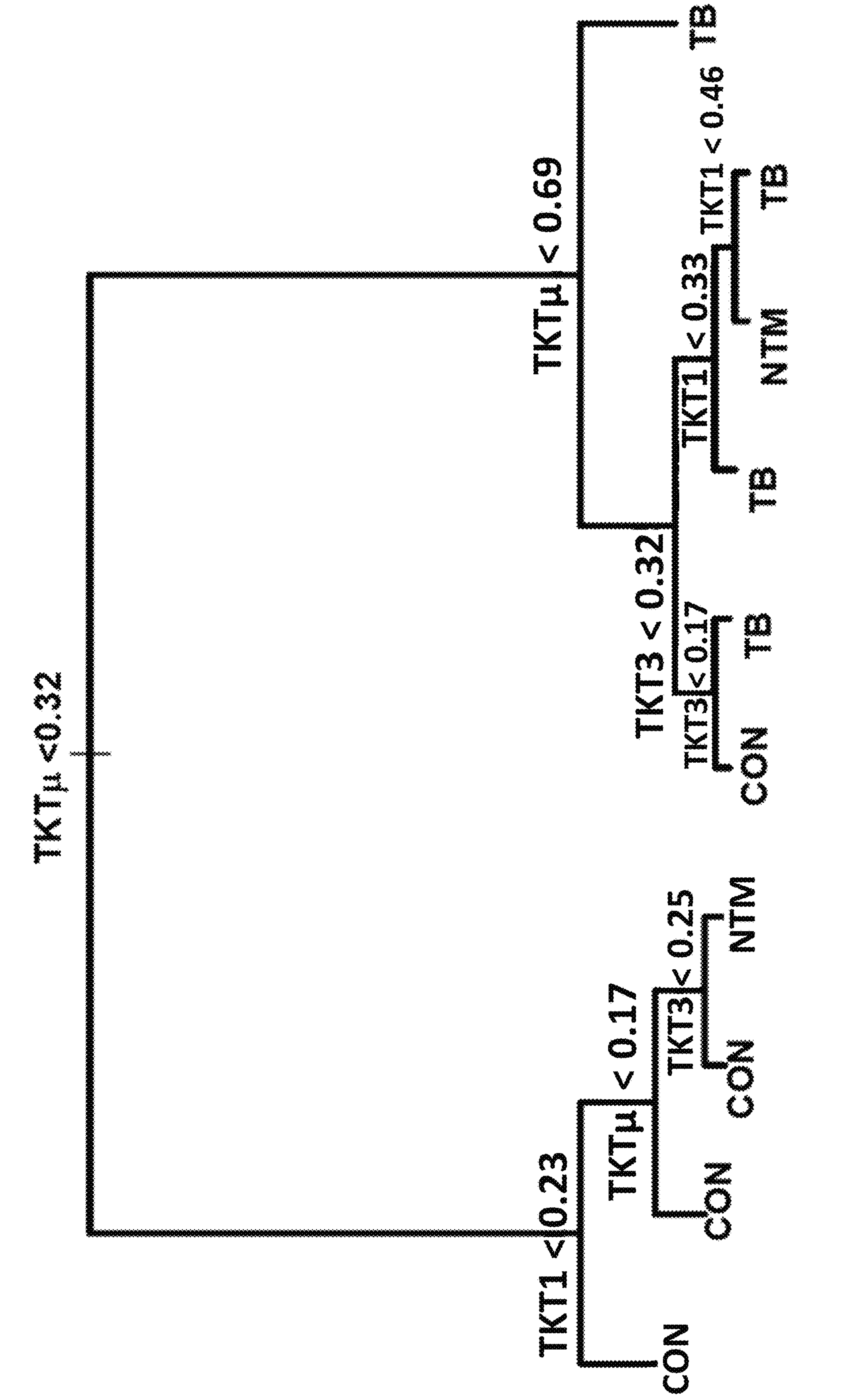
Figure 15E:
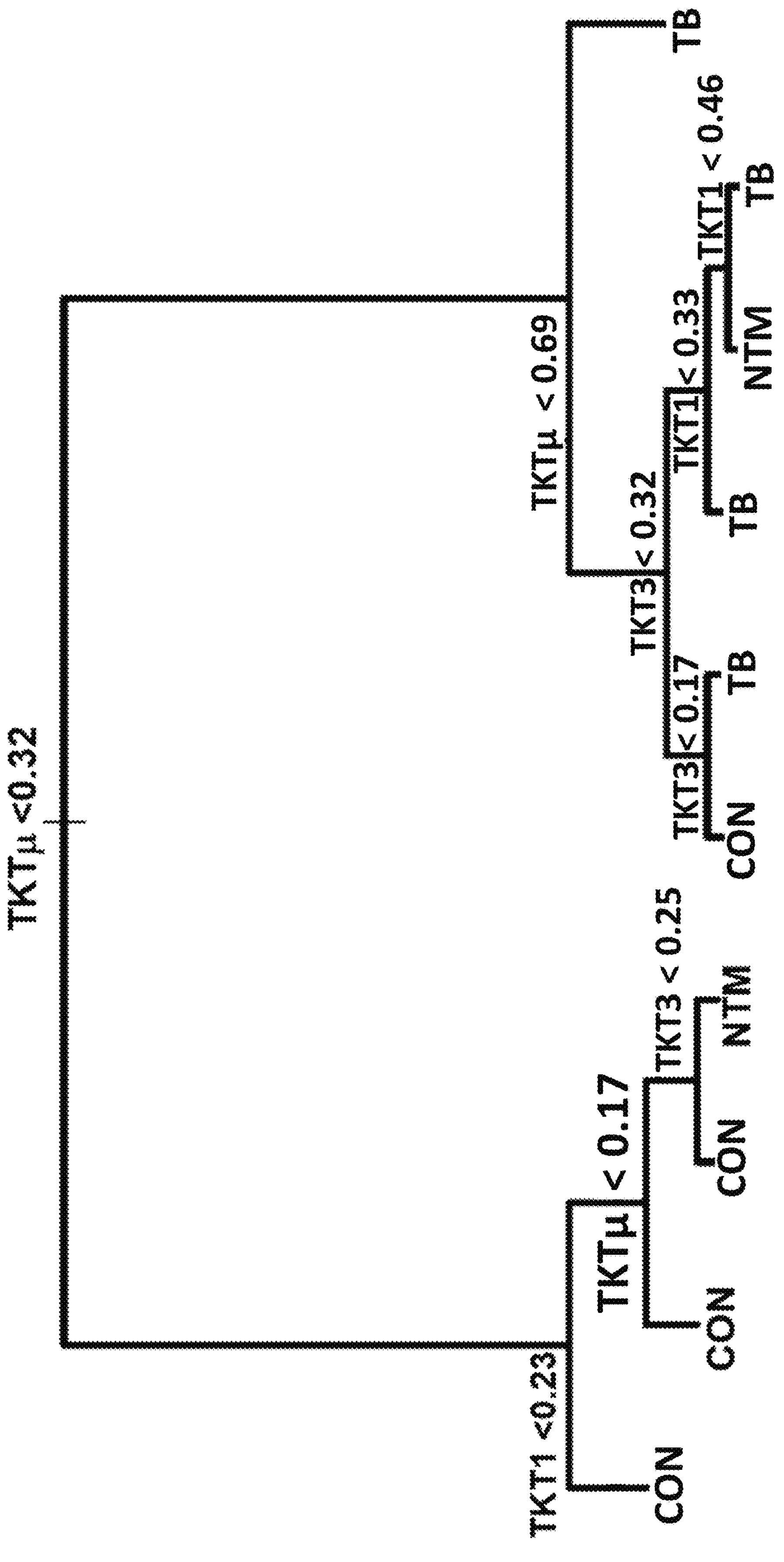

Performance of combination of TKT based immunodiagnostic. To determine if the combination of three epitope specific antibodies will increase the diagnostic accuracy of TKT immunoassay, the ROC curves of combined epitopes were generated using the entire dataset. The combination of all three TKT markers (TKTμ+TKT1+TKT3) yielded a mean±SE AUC of 0.98±0.0 (FIG. 15A and Table 11). The 10-fold CV yielded a mean sensitivity of 0.98±0.01, specificity of 0.87±0.02, accuracy of 0.90±0.03, NPV of 0.99±0.01 and PPV of 0.75±0.03. This model performed similarly to model TKTμ, which overall performed better than both TKT1 and TKT3 models. The DT modeling was performed for combined TKT epitope specific antibodies data sets while excluding and including NTM data. The trained DT for TKTμ+TKT1+TKT3 data while excluding NTM results are shown in FIG. 15B. FIG. 15C depicts the pruned DT for TKTμ+TKT1+TKT3 based on misclassification or deviance. The DT without NTM group yielded the precision value of 0.91 for TB and 0.99 for non-TB group with a sensitivity of 0.98, specificity of 0.94, accuracy of 0.96, and NPV of 0.99 (FIG. 15B). Trained DT for combined markers with data including NTM is shown in FIG. 15D. FIG. 15E depicts the pruned DT for TKTμ+TKT1+TKT3 antibodies based on misclassification or deviance. The DT with the NTM group contained the best accuracy of the DT's tied with TKTμ+TKT3, and yielded precision values of 0.89 for active TB, 0.93 for non-TB group, and 0.57 for NTM with a sensitivity of 0.98, specificity of 0.93, accuracy of 0.95, and NPV of 0.99 based on TB (FIG. 15E).

The combined markers of TKTμ and either TKT1 or TKT3 produced the best 10-fold CV results (Table 10). TKTμ and M.tb TKT3 yielded a mean±SE AUC of 0.98±0.0. The 10-fold CV yielded a mean sensitivity of 0.99±0.01, specificity of 0.87±0.01, accuracy of 0.91±0.01, NPV of 1.0±0.0 and PPV of 0.75±0.03. The combined markers, TKTμ and M.tb TKT1 yielded a mean AUC of 0.98±0.0. The 10-fold CV yielded a mean sensitivity of 0.99±0.01, specificity of 0.88±0.02, accuracy of 0.91±0.01, NPV of 0.99±0.0 and PPV of 0.77±0.04. Table 11 depicts the performance of combined markers versus each independent in DT.

Random Forest. One unbiased and stable methodology applied in biomarker discovery is Random Forest (RF), a decision tree based statistical machine learning method (Breiman, Machine Learning 45:5-32, 2001). Table 12 depicts the performance of RF after randomly selecting one of two markers for each of the 500 trees, one of three markers, or just TKTμ (also known as bagging), and then averaging the results before applying the test set. The application of RF as an unbiased machine learning approach proved beneficial. Starting with the highest performance antibody against TKTμ, TKT1 or TKT3 results were added sequentially into the model to assess the overall performance parameters. The combination of TKTμ and TKT3 data yielded a better performance than TKTμ epitope antibody alone or a combination of TKTμ with TKT1 (Table 12).

TABLE 12

| TB v Non-TB v (NTM) | With NTM | Random Forest TB Performance Parameters[a] | | | | |
|---|---|---|---|---|---|---|
| | | Sensitivity | Specificity | PPV | NPV | Accuracy |
| TKTμ | No | 0.929 (0.851, 1) | 0.914 (0.849, 0.980) | 0.867 (0.768, 0.966) | 0.955 (0.905, 1) | 0.920 (0.869, 0.970) |
| | Yes | 0.818 (0.704, 0.932) | 0.940 (0.889, 0.991) | 0.878 (0.818, 0.938) | 0.907 (0.846, 0.968) | 0.898 (0.845, 0.950) |
| TKTμ + TKT1 | No | 0.929 (0.851, 1) | 0.943 (0.888, 0.997) | 0.907 (0.820, 0.994) | 0.957 (0.908, 1) | 0.938 (0.893, 0.982) |
| | Yes | 0.795 (0.676, 0.915) | 0.952 (0.906, 0.998) | 0.897 (0.802, 0.993) | 0.898 (0.834, 0.961) | 0.898 (0.845, 0.950) |
| TKTμ + TKT3 | No | **1** **(1, 1)** | 0.929 (0.868, 0.989) | 0.894 (0.805, 0.982) | **1** **(1, 1)** | 0.955 (0.917, 0.994) |
| | Yes | 0.864 (0.762, 0.965) | 0.976 (0.943, 1) | 0.950 (0.882, 1) | 0.931 (0.878, 0.984) | 0.937 (0.895, 0.979) |

TABLE 12-continued

| TB v Non-TB v (NTM) | With NTM | Random Forest TB Performance Parameters[a] Sensitivity | Specificity | PPV | NPV | Accuracy |
|---|---|---|---|---|---|---|
| TKTμ + TKT1 + TKT3 | No | **1** **(1, 1)** | **0.957** **(0.910, 1)** | **0.933** **(0.860, 1)** | **1** **(1, 1)** | **0.973** **(0.943, 1)** |
| | Yes | *0.886* *(0.793, 0.980)* | *0.988* *(0.964, 1)* | *0.975* *(0.927, 1)* | *0.943* *(0.894, 0.991)* | *0.953* *(0.916, 0.990)* |

Bold indicates the best parameter of "With NTM" = No,
Italics indicates the best parameter of "With NTM" = Yes
[a]Parameter & Confidence Interval: 95%, assumed normal, parameter ± 1.96*SE, SE is standard error of proportion Without NTM, the best Random Forest model, drawing from all three markers, produced a precision (PPV) of 0.93 for the prediction of TB. The TB performance parameters consisted of sensitivity of 1.0, specificity of 0.96, accuracy of 0.97, and NPV of 1.0. Including NTM, TB performances data saw an increased PPV of 0.98 and a higher specificity (0.99) but had a lower sensitivity of 0.89 and a slightly lower accuracy of 0.95, and lower NPV of 0.94. Overall, the combination model of TKTμ and TKT3 antibodies led to an improvement from just including TKTμ alone which had lower performances in all parameters, with and without NTM. Combining all three-epitope specific IgGs and applying RF algorithm when excluding NTM data sets improved the TB performance with a sensitivity of 1, specificity of 0.957, PPV of 0.993, NPV of 1 and accuracy of 0.73. Inclusion of NTM data sets in the same model decreased the sensitivity to 0.886, NPV of 0.943 and accuracy of 0.953, but improved specificity of 0.988 and PPV of 0.975 (Table 12).

These results clearly show that ELISA based detection of serum IgG against all the TKT peptides has great sensitivity, specificity, and accuracy to distinguish between active TB and non-TB subjects, even NTM, and the combination of three markers will improve the diagnostic precision for active pulmonary TB.

Discussion

Despite advances in molecular TB diagnostics, there is an unmet need for a point-of-care non-sputum-based TB test (Wallis et al., *Lancet* 375(9729): 1920-37, 2010; World Health Organization. *WHO operational handbook on tuberculosis: module* 3*: diagnosis: tests for tuberculosis infection.* 2022 (ISBN: 978-92-4-005834-7); Hong et al., *Sci Transl Med.* 14(639): eabj4124, 2022). Through immunoscreening of a novel T7 phage library, classifiers that specifically bind to IgGs present in sera from patients with active pulmonary TB were identified. It was discovered that one of these classifier clones is aligned with M.tb transketolase (TKT). Three TKT epitopes (TKTμ, TKT1, and TKT3) were designed to detect TKT-specific IgGs in sera of patients with TB (Talreja et al., *Microbiol Spectr.* 11(1): e03377-22, doi: 10.1128/spectrum.03377-22. Epub 2023 Jan. 18). That research (at least a portion of which is described in the above examples) showed that IgGs of TB sera differentially bind to all three epitopes and can distinguish TB from LTBI, controls and sarcoidosis (Id.).

In the current study, utilizing TKT peptides, IgG specific TKT epitopes were measured via direct ELISA and 510 subjects including TB, NTM, LTBI, sarcoidosis, lung cancer and healthy controls, were tested. To predict TB diagnostic performances of TKT-based specific IgGs, rigorous statistical analyses were performed by constructing three classification models (ROC CV, DT and RF). All three models confirmed excellent performance of IgG specific antibodies against TKT epitopes, and best performance was observed by combining the antibodies against TKTμ and TKT3 and/or TKT1 with greatest sensitivity, specificity, and accuracy to distinguish active TB subjects from other groups, including NTM and LTBI. The best and most reliable prediction model was achieved through RF by ensemble modeling of 500 trees and assessing the performances of IgG based TKT to predict active pulmonary TB from other study groups. Despite inclusion of the NTM data set the TB diagnostic precision achieved 98% with a sensitivity of 89% and specificity of 99%. Previous data was validated in an independent cohorts and additionally assayed samples of NTM subjects as well as smear negative culture positive TB subjects. Inclusion of NTM samples reduced the sensitivity, but improved the specificity, and positive predictive values. Although TKT of *Mycobacterium avium* has 87% homology to the M.tb TKT core sequence, the current study shows that TKT specific IgGs are differentially expressed in TB versus MAC infected individuals. Studies have shown that variations in only one or two AAs might change the immunogenicity, virulence, or drug resistance (Bhattacharyya et al., *BMC Microbiol.* 20(1): 1-14, 2020, Advani et al., *Front Microbiol.* 10:309, 2019). In the NTM study group, some subjects with elevated IgG antibodies against TKT1 and TKT3 peptides that can be due to cross antibody reactivity or coinfection were found. Recently, NTM-TB coinfections among patients with pulmonary TB have been reported and this coinfection rate varies (between 2.8-8%) depending on the geographic area, yet the true incidence is not known (Lin et al., *Medicine* 99(52), 2020; Sharma et al., *Indian J Med Res.* 150(5): 458, 2019). Although the TKT specific antibodies differentiate TB from various conditions including LTBI and NTM, the TKT specific antibodies have low sensitivity and specificity in discriminating NTM from other conditions.

The growing incidence of NTM infection combined with misdiagnosis and common treatment failure represent an expanding unmet medical need (Somoskovi et al., *Clin Chest Med.* 23(3): 585-597, 2002). Several molecular tests such as the WHO-recommended Xpert® MTB/RIF (Cepheid) and Xpert® MTB/RIF Ultra assays have provided a rapid alternative to sputum smear for detection of M.tb (Anand & Biswas, *EBioMedicine* 71, 2021; World Health Organization. "Use of Xpert® MTB/RIF and Xpert® MTB/RIF Ultra on GeneXpert 10-colour instruments: WHO policy statement." (27 pages) 2021 (ISBN: 9789240040106)), yet there are limitations of these tests in smear negative TB, children, HIV infected subjects and in some cases, it cannot differentiate M.tb and infection with NTM species (Horne et al., *Cochrane Database Syst Rev.* (6) 2019; Kay et al., *Cochrane Database of Syst Rev.* (9) 2022).

Although several previous studies have demonstrated that the Xpert® assay showed excellent performance in distinguishing M.tb from NTM in smear-positive or negative clinical specimens, the misdiagnosis of MTB by the Xpert® assay was recently reported for several NTM species, including, MAC, *M. abscessus, M. marinum* (Somoskovi et al., *Clin Chest Med.* 23(3): 585-597, 2002; Anand & Biswas, *EBioMedicine* 71, 2021; Pang et al., *Infection* 45(5): 677-681, 2017). Culture of slowly growing mycobacteria, such as MAC can take up to 4 to 6 weeks, and in 10-20% of cases the *bacillus* is not successfully cultivated. To decrease morbidity and mortality, accurate and affordable diagnostic point-of-care (POC) tests are urgently needed. The existing TB diagnostics pipeline still does not have a simple, rapid, inexpensive POC test (World Health Organization. Global Tuberculosis Report 2021: Supp. mat. 2022 (ISBN: 978-92-4-003702-1)). The WHO has defined high-priority target product profiles for tuberculosis diagnostics (Hong et al., *Sci Transl Med.* 14(639): eabj4124, 2022; Denkinger et al., *J Infect Dis.* 220(Suppl 3): S91-S8, 2019). These priorities include a sputum-based POC smear replacement test, a non-sputum-based POC TB test, a POC triage test, and a rapid drug-susceptibility test (DST) (Breiman, Machine Learning 45:5-32, 2001). The appropriate POC tests could ensure timely and appropriate initiation of tuberculosis treatment in vulnerable subjects including children or other high-risk groups to prevent rapid clinical deterioration (Winston & Menzies, Pediatrics 130(6): e1425-e32, 2012). Target product profiles (TPPs) issued by the WHO defining non-sputum-based rapid biomarkers performance as a triage test recommended to have a sensitivity >95%; and a specificity >80% to screen patients with suspected TB disease and to reduce the population that requires confirmatory tests (Hong et al., *Sci Transl Med.* 14(639): eabj4124, 2022; Melkie et al., *Eur Respir Rev.* 31(163), 2022). The most common NTM lung pathogen, *Mycobacterium avium* complex (MAC) requires complex and long-term antibiotic treatment regimens causing adherence issues (Haworth et al., *Thorax* 72(Suppl 2): ii1-ii64, 2017). Rigorous statistical analyses utilizing various statistical modeling and machine learning, including DT and RF showed that the best model with highest accuracy, PPV and NPV is when all three markers were combined and the best ROC model when TKTμ is combined with TKT1 or TKT3 (Tables 11 & 12). These results clearly show that performance of IgG based immunoreactivities against TKT specific epitopes outperforms current TB diagnostic tests in terms of sensitivity, specificity, positive predictive value, and accuracy and this method fulfills the WHO criteria as a triage test.

Among three epitopes, the TKTμ performance surpassed the performance of antibodies against TKT1 and TKT3 epitopes. M.tb TKT1 has 26% homology with the novel TKTμ peptide, while the M.tb TKT3 has only 20% homology with TKTμ epitopes. Despite significant similarity between TKT1 and TKT3, TKT3 performed better for TB diagnostic. This could imply that either these epitopes are conformational epitopes created by protein folding that are recognized by antibodies and B cells of active TB patients (Irving et al., *Curr Opin Chem Biol.* 5(3): 314-324, 2001). Of note, the TKTμ was discovered through immunoscreening of a custom-made T7 phage display library and comparison of immunoreactivity among TB, sarcoidosis, and healthy subjects, while TKT1 and TKT3 was designed based on the silico analyses and antigen prediction (Talreja et al., *Microbiol Spectr.* 11(1): e03377-22, doi: 10.1128/spectrum.03377-22. Epub 2023 Jan. 18). These results suggest that immunoscreening of the T7 phage display library has a potential to identify specific epitopes distinguishing NTM from TB and other respiratory diseases if immunoscreened with NTM and TB sera concomitantly to identify the specific classifier clones for each condition.

The identification of epitopes reactant to IgG present in TB or NTM sera is a major milestone and constitutes a strong beginning for understanding the role of antibodies in mycobacterial immunity.

Example 4: TKT Epitopes of M.tb, *M. avium, M. intracellulare*, and *M. abscessus*

The amino acid sequence of TB-specific novel epitopes TKTμ, M.tb TKT1 and TKT3 are shown in Table 13. M.tb TKT1 has 26% homology with the herein described peptide TKTμ, and M.tb TKT3 has 20% homology with TKTμ. *M. avium* TKT epitopes, Mav1, Mav2, and Mav3 were designed to detect TKT specific IgGs in NTM sera. Mav1 has 22% homology with TKTμ, 40% homology with TKT1, 36% homology with TKT3. THQPI (SEQ ID NO: 1) is the core common sequence in all these epitopes. Two AAs (A and K, shown in bold in Table 13) in Mav1, 2 and 3 are different from those in M.tb TKT. An antigenicity prediction tool showed that Mav1 and 3 are predicted to be antigenic, but Mav2 is not. Mav1 TKT peptide ELISA was developed to differentiate NTM from TB and healthy controls.

These steps include evaluation of each classifiers clones for its antigenicity, sequence alignments with M.tb reference (NCBI) and with important pathogenic NTM, including MAC (*M. avium, M. intracellulare*, and *M. abscessus*). Having reviewed the challenge of discovery of antigenic epitopes that can distinguish between M.tb and NTM, sequence alignments were performed and examined the homology of M.tb TKT with several non-tuberculous mycobacteria, including *M. smegmatis, M. abscesses* and *M. avium*. The sequence homology between M.tb and *M. smegmatis* TKT is 27%. *M. smegmatis* does not have THQPI sequence. The sequence homology between M.tb and *M. abscesses* is 77%. There is a difference in one AA for the seq THQPI (M.tb; SEQ ID NO: 1) and *M. abscesses*, which contains a Valine in place of the terminal Isoleucine of SEQ ID NO: 1. The sequence homology between M.tb and *M. avium* is 87%. Regarding TKT3 peptide from M.tb (SEQ ID NO: 5), there is a difference in two AA between M.tb and *M. abscesses* (SEQ ID NO: 17). There is one AA difference between M.tb and *M. avium* for TKT3 peptide (SEQ ID NO: 5).

Although TKT of MAC has 87% homology to M.tb TKT core sequence, our current study shows that TKT specific IgGs differentially expressed in TB versus MAC infected individuals. Studies showed that variations in only one or two AAs might change the immunogenicity, virulence, or drug resistance. This is most likely due to protein folding and three-dimensional structure of peptide in fluid phase.

TABLE 13

Exemplary TKT epitopes

| Name | Sequence (Aligned) | Sequence ID |
|---|---|---|
| M.tb TKT1: | GEDGP*THQPI*EHLSA | SEQ ID NO: 3 |
| M.tb TKT3: | HDSIGLGEDGP*THQPI*EHLS | SEQ ID NO: 5 |

TABLE 13-continued

Exemplary TKT epitopes

| Name | Sequence (Aligned) | Sequence ID |
|---|---|---|
| TKTμ: | DLSSEVA*THQPI*IACLP | SEQ ID NO: 12 |
| Mav1: | *THQPI*EHLAALRAIPKLSVVRP | SEQ ID NO: 13 |
| Mav2: | GEDGP*THQPI*EHLAALRAIPKLSVVRP | SEQ ID NO: 14 |
| Mav3: | HDSIGLGEDGP*THQPI*EHLAALRAIPKLSVVRP | SEQ ID NO: 15 |
| | HLAALRAIPKLSVVRP | SEQ ID NO: 16 |
| *M. abscesses* | HDSIGLGEDGPTHQPVEHLA | SEQ ID NO: 17 |

Because of the high predicted antigenicity of MAV1 (SEQ ID NO: 13), sequences corresponding to MAV1 were designed, including SEQ ID NO: 16. The same algorithm as in earlier Examples was then followed to develop an ELISA based assay employing these sequences. The same samples of healthy controls, TB, and NTM were assessed. The immunoreactivity of all samples regardless of infectious status was low and MAV1-based ELISA was not able to differentiate between TB, NTM, or healthy controls.

These data indicated that the core THQPI (SEQ ID NO: 1) sequence is important to be within (and generally near the middle of) an amino acid sequence used in the herein-described ELISAs. Altering this sequence, including moving its position within the peptide, possibly due to changes in peptide folding, results in the peptide not binding to human IgG.

(X) CLOSING PARAGRAPHS

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles, other written text, and web site content throughout this specification (referenced materials herein). Each of the referenced materials are individually incorporated herein by reference in their entirety for their referenced teaching(s), as of the filing date of the first application in the priority chain in which the specific reference was included. For instance, with regard to chemical compounds, nucleic acid, and amino acids sequences referenced herein that are available in a public database, the information in the database entry is incorporated herein by reference as of the date of an application in the priority chain in which the database identifier for that compound or sequence was first included in the text.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 11th Edition or a dictionary known to those of ordinary skill in the art, such as the Oxford Dictionary of Biochemistry and Molecular Biology, 2nd Edition (Ed. Anthony Smith, Oxford University Press, Oxford, 2006), and/or A Dictionary of Chemistry, 8th Edition (Ed. J. Law & R. Rennie, Oxford University Press, 2020).

What is claimed is:

1. A method of detecting antibodies that specifically bind a *Mycobacterium tuberculosis* (M.tb) peptide in a sample of a subject suspected of having an M.tb infection, comprising detecting in the sample a presence of an antibody that reacts with a peptide consisting of the sequence of SEQ ID NO: 3 (TKT1; GEDGPTHQPIEHLSA), or SEQ ID NO: 5 (TKT3; HDSIGLGEDGPTHQPIEHLS).

2. The method of claim 1, wherein the detecting comprises performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex particle-based suspension array assay, a mass spectrometry assay, or a particulate-based assay.

3. The method of claim 2, wherein the enzyme-linked immunoassay is an enzyme-linked immunosorbent assay (ELISA).

4. The method of claim 1, wherein the sample is serum, and the serum is diluted more than 1:50, 1:250 to 1:16000, 1:400-1:1000, or 1:500, serum to dilution agent.

5. An immunoassay kit for selectively detecting anti-transketolase antibody in a biological sample, the kit comprising:

as capture reagent, a peptide consisting of the sequence of SEQ ID NO: 3 or SEQ ID NO: 5 bound to a solid support, wherein the peptide forms a complex with an anti-transketolase antibody in the biological sample; and as detection reagent, a detectable anti-human IgG antibody, wherein the detectable anti-human IgG antibody binds to anti-transketolase antibody in the complex.

6. The kit of claim 5, wherein the capture reagent is coated on a microtiter plate.

7. The kit of claim 5, further comprising a means for detecting the detectable antibody.

8. The kit of claim 7, wherein the detection means is colorimetric.

9. The kit of claim 5, further comprising a fluorometric reagent, the fluorometric reagent configured to amplify a signal from the detectable antibody.

10. The kit of claim 5, further comprising 3,3',5,5'-tetramethyl benzidine, wherein the detectable antibody is HRP-conjugated.

11. The kit of claim 5, wherein the detectable antibody is a monoclonal antibody.

12. The kit of claim 11, wherein the detectable antibody is a goat monoclonal antibody.

13. The kit of claim 5, further comprising anti-transketolase antibody as an antibody standard.

* * * * *

SEQUENCE LISTING

```
Sequence total quantity: 20
SEQ ID NO: 1           moltype = AA  length = 5
FEATURE                Location/Qualifiers
source                 1..5
                       mol_type = protein
                       organism = Mycobacterium tuberculosis
SEQUENCE: 1
THQPI                                                       5

SEQ ID NO: 2           moltype = AA  length = 18
FEATURE                Location/Qualifiers
source                 1..18
                       mol_type = protein
                       organism = Mycobacterium tuberculosis
SEQUENCE: 2
THDSIGLGED GPTHQPIE                                         18

SEQ ID NO: 3           moltype = AA  length = 15
FEATURE                Location/Qualifiers
source                 1..15
                       mol_type = protein
                       organism = synthetic construct
SEQUENCE: 3
GEDGPTHQPI EHLSA                                            15

SEQ ID NO: 4           moltype = AA  length = 22
FEATURE                Location/Qualifiers
source                 1..22
                       mol_type = protein
                       organism = synthetic construct
SEQUENCE: 4
DGPTHQPIEH LSALRAIPRL SV                                    22

SEQ ID NO: 5           moltype = AA  length = 20
FEATURE                Location/Qualifiers
source                 1..20
                       mol_type = protein
                       organism = synthetic construct
SEQUENCE: 5
HDSIGLGEDG PTHQPIEHLS                                       20

SEQ ID NO: 6           moltype = AA  length = 457
FEATURE                Location/Qualifiers
source                 1..457
                       mol_type = protein
```

```
                         organism = Homo sapiens
SEQUENCE: 6
MAFASIYKLD NLVAILDINR LGQSDPAPLQ HQMDIYQKRC EAFGWHAIIV DGHSVEELCK  60
AFGQAKHQPT AIIAKTFKGR GITGVEDKES WHGKPLPKNM AEQIIQEIYS QIQSKKKILA  120
TPPQEDAPSV DIANIRMPSL PSYKVGDKIA TRKAYGQALA KLGHASDRII ALDGDTKNST  180
FSEIFKKEHP DRFIECYIAE QNMVSIAVGC ATRNRTVPFC STFAAFFTRA FDQIRMAAIS  240
ESNINLCGSH CGVSIGEDGP SQMALEDLAM FRSVPTSTVF YPSDGVATEK AVELAANTKG  300
ICFIRTSRPE NAIIYNNNED FQVGQAKVVL KSKDDQVTVI GAGVTLHEAL AAAELLKKEK  360
INIRVLDPFT IKPLDRKLIL DSARATKGRI LTVEDHYYEG GIGEAVSSAV VGEPGITVTH  420
LAVNRVPRSG KPAELLKMFG IDRDAIAQAV RGLITKA                          457

SEQ ID NO: 7             moltype = AA  length = 662
FEATURE                  Location/Qualifiers
source                   1..662
                         mol_type = protein
                         organism = Staphylococcus aureus
SEQUENCE: 7
MFNEKDQLAV DTLRALSIDT IEKANSGHPG LPMGAAPMAY TLWTRHLNFN PQSKDYFNRD  60
RFVLSAGHGS ALLYSLLHVS GSLELEELKQ FRQWGSKTPG HPEYRHTDGV EVTTGPLGQG  120
FAMSVGLALA EDHLAGKFNK EGYNVVDHYT YVLASDGDLM EGISHEAASF AGHNKLSKLV  180
VLYDSNDISL DGELNKAFSE NTKARFEAYG WNYLLVKDGN DLEEIDKAIT TAKSQEGPTI  240
IEVKTTIGFG SPNKAGTNGV HGAPLGEVER KLTFENYGLD PEKRFNVSEE VYEIFQNTML  300
KRANEDESQW NSLLEKYAET YPELAEEFKL AISGKLPKNY KDELPRFELG HNGASRADSG  360
TVIQAISKTV PSFFGGSADL AGSNKSNVND ATDYSSETPE GKNVWFGVRE FAMGAAVNGM  420
AAHGGLHPYG ATFFVFSDYL KPALRLSSIM GLNATFIFTH DSIAVGEDGP THEPIEQLAG  480
LRAIPNMNVI RPADGNETRV AWEVALESES TPTSLVLTRQ NLPVLDVPED VVEEGVRKGA  540
YTVYGSEETP EFLLLASGSE VSLAVEAAKD LEKQGKSVRV VSMPNWNAFE QQSEEYKESV  600
IPSSVTKRVA IEMASPLGWH KYVGTAGKVI AIDGFGASAP GDLVVEKYGF TKENILNQVM  660
SL                                                                662

SEQ ID NO: 8             moltype = AA  length = 700
FEATURE                  Location/Qualifiers
source                   1..700
                         mol_type = protein
                         organism = Mycobacterium tuberculosis
SEQUENCE: 8
MTTLEEISAL TRPRHPDYWT EIDSAAVDTI RVLAADAVQK VGNGHPGTAM SLAPLAYTLF  60
QRTMRHDPSD THWLGRDRFV LSAGHSSLTL YIQLYLGGFG LELSDIESLR TWGSKTPGHP  120
EFRHTPGVEI TTGPLGQGLA SAVGMAMASR YERGLFDPDA EPGASPFDHY IYVIASDGDI  180
EEGVTSEASS LAAVQQLGNL IVFYDRNQIS IEDDTNIALC EDTAARYRAY GWHVQEVEGG  240
ENVVGIEEAI ANAQAVTDRP SFIALRTVIG YPAPNLMDTG KAHGAALGDD EVAAVKKIVG  300
FDPDKTFQVR EDVLTHTRGL VARGKQAHER WQLEFDAWAR REPERKALLD RLLAQKLPDG  360
WDADLPHWEP GSKALATRAA SGAVLSALGP KLPELWGGSA DLAGSNNTTI KGADSFGPPS  420
ISTKEYTAHW YGRTLHFGVR EHAMGAILSG IVLHGPTRAY GGTFLQFSDY MRPAVRLAAL  480
MDIDTIYVWT HDSIGLGEDG PTHQPIEHLS ALRAIPRLSV VRPADANETA YAWRTILARR  540
NGSGPVGLIL TRQGVPVLDG TDAEGVARGG YVLSDAGGLQ PGEEPDVILI ATGSEVQLAV  600
AAQTLLADND ILARVVSMPC LEWFEAQPYE YRDAVLPPTV SARVAVEAGV AQCWHQLVGD  660
TGEIVSIEHY GESADHKTLF REYGFTAEAV AAAAERALDN                       700

SEQ ID NO: 9             moltype = AA  length = 48
FEATURE                  Location/Qualifiers
source                   1..48
                         mol_type = protein
                         organism = Homo sapiens
SEQUENCE: 9
HCGVSIGEDG PSQMALEDLA MFRSVPTSTV FYPSDGVATE KAVELAAN               48

SEQ ID NO: 10            moltype = AA  length = 48
FEATURE                  Location/Qualifiers
source                   1..48
                         mol_type = protein
                         organism = Staphylococcus aureus
SEQUENCE: 10
HDSIAVGEDG PTHEPIEQLA GLRAIPNMNV IRPADGNETR VAWEVALE               48

SEQ ID NO: 11            moltype = AA  length = 50
FEATURE                  Location/Qualifiers
source                   1..50
                         mol_type = protein
                         organism = Mycobacterium tuberculosis
SEQUENCE: 11
HDSIGLGEDG PTHQPIEHLS ALRAIPRLSV VRPADANETA YAWRTILARR             50

SEQ ID NO: 12            moltype = AA  length = 17
FEATURE                  Location/Qualifiers
source                   1..17
                         mol_type = protein
                         organism = synthetic construct
SEQUENCE: 12
```

```
DLSSEVATHQ PIIACLP                                                   17

SEQ ID NO: 13          moltype = AA  length = 22
FEATURE                Location/Qualifiers
source                 1..22
                       mol_type = protein
                       organism = synthetic construct
SEQUENCE: 13
THQPIEHLAA LRAIPKLSVV RP                                             22

SEQ ID NO: 14          moltype = AA  length = 27
FEATURE                Location/Qualifiers
source                 1..27
                       mol_type = protein
                       organism = synthetic construct
SEQUENCE: 14
GEDGPTHQPI EHLAALRAIP KLSVVRP                                        27

SEQ ID NO: 15          moltype = AA  length = 33
FEATURE                Location/Qualifiers
source                 1..33
                       mol_type = protein
                       organism = synthetic construct
SEQUENCE: 15
HDSIGLGEDG PTHQPIEHLA ALRAIPKLSV VRP                                 33

SEQ ID NO: 16          moltype = AA  length = 16
FEATURE                Location/Qualifiers
source                 1..16
                       mol_type = protein
                       organism = synthetic construct
SEQUENCE: 16
HLAALRAIPK LSVVRP                                                    16

SEQ ID NO: 17          moltype = AA  length = 20
FEATURE                Location/Qualifiers
source                 1..20
                       mol_type = protein
                       organism = Mycobacterium abscessus
SEQUENCE: 17
HDSIGLGEDG PTHQPVEHLA                                                20

SEQ ID NO: 18          moltype = AA  length = 699
FEATURE                Location/Qualifiers
source                 1..699
                       mol_type = protein
                       organism = Mycobacterium avium
SEQUENCE: 18
MTTLEEISAL TQPHLPDDWS ELDSAAVDTI RVLAADAVQK VGNGHPGTAM SLAPLAYTLF  60
QRVMRHDPSD THWLGRDRFV LSAGHSSLTL YLQLYLGGFG LELSDIESLR TWGSKTPGHP  120
EFRHTKGVEI TTGPLGQGLA SAVGMAMASR YERGLFDPDA AAGTSPFDHF IYVIASDGDI  180
EEGVTSEASS LAAVQQLGNL IVFYDHNQIS IEDDTNIALC EDTAARYEAY GWHVQRVEGG  240
ENVVAIEEAI AAAKAVTDRP SFIELRTIIG YPAPNAMNTG KAHGAALGEE EVAAVKKILG  300
FDPDKTFQVR DKVIAHTRKL VDRGREAHQK WQTDFDAWAQ REPERKALLE RLTAEKLPDG  360
WDADLPHWEP GSDAIATRKA SGAVLNAVAP KLPELWGGSA DLAESNLTTI NNADSFGPPS  420
ISTKEFTASW YGRVLHFGVR EHAMGAILSG IVLHGPTRAY GGTFLQFSDY MRPAVRLASL  480
MDIDTIYVWT HDSIGLGEDG PTHQPIEHLA ALRAIPKLSV VRPADANETA YAWRTILARG  540
NGSGPVGLVL TRQGLPVLEG TDADGVARGG YILGSDGEEA GQEPDVILIA TGSEVQLAVE  600
AQKLLADKDI VARVVSMPCV EWFESQPDDY RDSVLPPSVS ARVAVEAGVA QSWHKLVGDT  660
GKIISIEHYG ESADYKTLFR EFGFTAEAVA AAAEEVVDN                           699

SEQ ID NO: 19          moltype = AA  length = 644
FEATURE                Location/Qualifiers
source                 1..644
                       mol_type = protein
                       organism = Mycobacterium smegmatis
SEQUENCE: 19
MNESNDRIDT TLVGRLARQL RADAIRASTA AGSGHPTSSM SAADLTAVLL ARHLSYDWER  60
PDHPDNDHFI LSKGHASPLL YAAFKAVGVI TDTELMTGYR RFGSRLQGHP TPVLPWVDVA  120
SGSLGQGIAI GVGVALAGKF LDRSGFHVWT LCGDSEMAEG SVWEALDKAG YYGLSNFTVI  180
VDVNRLGQRG PTEFGWDLET YAKRVEAFGA RAISVDGHRL EAIDQALTAA RNTTQPTVIL  240
ARTVKGRGFS EVEDREGWHG KAFPPEMARR ALAELGEVEG LTVAGPKPAS RSGQSSAPGA  300
GNPDGFSDRP RYAPGEKVAT RAAYGAAVAA LGAVNRRVVA LDGEVSNSTG AAEFTEHHPE  360
RYFEMFIAEQ QLVASSVGLH VRHYIPFAST FAAFLTRAHD FIRMAAVSQA NICLIGSHAG  420
VEIGADGPSQ MALEDLAMMR SVHGATVLYP SDATSTVALV DLMADADGVR YLRTTRGAYP  480
VLYEPATVFT IGGSHTLRSS SADDVTLIGA GVTVHQCLAA AESLHRDGIA ARVIDVYSVK  540
PIDRDTLLEA VRDTGARLVI AEDHHPEGGL GSAVLEAISG AETPRLKLMH LAVRAMPGSG  600
TPAELLADAA IDAASIDKAA RHLLQADDGR SDDGRSDDDE TLTA                     644
```

-continued

```
SEQ ID NO: 20          moltype = AA  length = 709
FEATURE                Location/Qualifiers
source                 1..709
                       mol_type = protein
                       organism = Mycobacterium abscessus
SEQUENCE: 20
MTAISRELAE VPTDIPTLTR VDHPDDWTEL DSRAVDTVRV LAADAVQKVG NGHPGTAMSL  60
APVAYTLFQR QLRHDPSDTT WIGRDRFVLS CGHSSLTLYL QLYLGGFGLE LSDIEALRTW  120
GSLTPGHPEY HHTKGVEITT GPLGQGLASA VGMAMASRYE RGLFDPDAAP GTSPFDHFIY  180
VIASDGDIEE GVTSEASSLA GTQQLGNLIV IWDDNEISIE HDTKIALSED TPARYEAYGW  240
HVQTVVSGEN VTGLEEALAN ARAVTDRPSF IALRTIIGYP APTKMNTGGV HGSALGADEV  300
AATKKILGFD PDKSFEVAPE VIAHTRELVT RGKQAHAEWD KSFEAWAARE PERKALLDRL  360
QARALPQGWD AGLPSWEPGS KAVATRAASG DTLSALGAKL PELWGGSADL AGSNNTTIKG  420
ADSFGPTSIA TSDWNAQPYG RTLHFGIREH AMGSILSGIV LHGPTRAYGG TFLQFADYMR  480
PAVRLAALMN IDPIYVWTHD SIGLGEDGPT HQPVEHLAAL RAIPNLSVVR PGDANETAYA  540
WATVLERQSS TGPVGLALTR QGVPILEGTS REGVAKGGYV LEAASDNPAD APDVILIGTG  600
SELQLAVEAK KILAAKGIAA SVVSLPCVEW FESQPQEYRD SVLPPSVRAR VVVEAGIAQG  660
WYKFVGDAGQ IVSLEHFGAS ADDKTLFREF GFTPDAVAAA AERSIAAAQ             709
```